United States Patent
Sugino et al.

(10) Patent No.: US 10,468,610 B2
(45) Date of Patent: Nov. 5, 2019

(54) ISOMER-MIXTURE METAL COMPLEX COMPOSITION, ORGANIC ELECTROLUMINESCENT ELEMENT, ILLUMINATOR, AND DISPLAY DEVICE

(71) Applicant: Konica Minolta, Inc., Chiyoda-ku, Tokyo (JP)

(72) Inventors: Motoaki Sugino, Akishima (JP); Hiroshi Kita, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 557 days.

(21) Appl. No.: 14/780,253

(22) PCT Filed: Mar. 20, 2014

(86) PCT No.: PCT/JP2014/057676
§ 371 (c)(1),
(2) Date: Sep. 25, 2015

(87) PCT Pub. No.: WO2014/156922
PCT Pub. Date: Oct. 2, 2014

(65) Prior Publication Data
US 2016/0056396 A1 Feb. 25, 2016

(30) Foreign Application Priority Data
Mar. 29, 2013 (JP) .................. 2013-072072

(51) Int. Cl.
*H01L 51/54* (2006.01)
*C09K 11/06* (2006.01)
*H01L 51/00* (2006.01)
*C07F 15/00* (2006.01)
*C09K 11/02* (2006.01)
*H01L 27/32* (2006.01)
*H01L 51/50* (2006.01)

(52) U.S. Cl.
CPC ...... *H01L 51/0085* (2013.01); *C07F 15/0033* (2013.01); *C07F 15/0086* (2013.01); *C09K 11/025* (2013.01); *C09K 11/06* (2013.01); *H01L 27/3244* (2013.01); *H01L 51/0059* (2013.01); *H01L 51/0072* (2013.01); *H01L 51/0073* (2013.01); *H01L 51/0087* (2013.01); C09K 2211/1007 (2013.01); C09K 2211/1011 (2013.01); C09K 2211/1029 (2013.01); C09K 2211/1033 (2013.01); C09K 2211/1037 (2013.01); C09K 2211/1044 (2013.01); C09K 2211/1059 (2013.01); C09K 2211/1088 (2013.01); C09K 2211/1092 (2013.01); C09K 2211/185 (2013.01); H01L 51/0074 (2013.01); H01L 51/5012 (2013.01); H01L 51/5016 (2013.01)

(58) Field of Classification Search
None
See application file for complete search history.

(56) References Cited

U.S. PATENT DOCUMENTS

| 6,097,147 A | 8/2000 | Baldo et al. | |
|---|---|---|---|
| 2007/0184301 A1* | 8/2007 | Oshiyama et al. | C07F 15/0086 428/690 |
| 2010/0141125 A1 | 6/2010 | Otsu et al. | |
| 2010/0264405 A1* | 10/2010 | Molt et al. | C07F 15/0033 257/40 |
| 2011/0057559 A1 | 3/2011 | Xia et al. | |

FOREIGN PATENT DOCUMENTS

| JP | 2011500644 A | 1/2011 |
|---|---|---|
| JP | 2012164731 A | 8/2012 |
| JP | 5403179 B1 | 1/2014 |
| KR | 20130110934 A | 10/2013 |
| WO | 2007097149 A1 | 8/2007 |
| WO | 2012170463 A1 | 12/2012 |

OTHER PUBLICATIONS

Machine translation of JP 2012-164731 (Aug. 2012).*
Extended European Search Report corresponding to Application No. 14776548.1-1555/2980094 PCT/JP2014/057676; dated Sep. 26, 2016.
European Office Action for corresponding EP Application No. 14776548.1-1552; dated Sep. 7, 2017.
International Search Report corresponding to Application No. PCT/JP2014/057676; dated Jun. 24, 2014, with English translation.
M.A. Baldo et al., "High Efficiency Fluorescent Organic Light-Emitting Devices Using a Phosphorescent Sensitizer", Nature 403, 750-753 (Feb. 17, 2000) | doi:10.1038/35001541.
Written Opinion of the International Searching Authority corresponding to Application No. PCT/JP2014/057676; dated Jun. 24, 2014.
International Preliminary Search Report on Patentabilty corresponding to Application No. PCT/JP2014/057676; dated Sep. 29, 2015, with English translation.

(Continued)

*Primary Examiner* — Marie R. Yamnitzky
(74) *Attorney, Agent, or Firm* — Cantor Colburn LLP

(57) ABSTRACT

An isomer-mixture metal complex composition that includes a plurality of atropisomers is described. This isomer-mixture metal complex composition is a metal complex composition which is a mixture of isomers each comprising a metal atom and a plurality of ligands, and is characterized by containing a plurality of atropisomers because at least one of the ligands has an aromatic ring as a substituent and the free rotation of the axis of the bonding between the aromatic ring and the ligand is inhibited by the formation of a complex of the metal atom with other ligand(s). An organic EL element using the isomer-mixture metal complex composition as a material for organic EL element is also described. Further, an illuminator and a display device which are obtained using the organic EL element are described.

10 Claims, 15 Drawing Sheets

(56) References Cited

OTHER PUBLICATIONS

CN Notification of Reasons for Rejection corresponding to Application No. JP2015-508394; dated May 23, 2017.
Korean Intellectual Property Office Notice of Preliminary Rejection corresponding to Application No. 10-2015-7025711; dated May 2, 2017.
Korean Intellectual Property Office Notice of Final Rejection corresponding to Application No. 10-2015-7025711; dated Jan. 25, 2018.

* cited by examiner

LIGHT

LIGHT mirror mirror

Scheme 1

Scheme 2

Scheme 3 trans isomer cis isomer fac isomer mer isomer

Λ (lambda) enantiomer         Δ (delta) enantiomer

Scheme 4 mirror

Scheme 5 bond to complex skeleton no symmetrical axis bond to complex skeleton symmetrical axis

ISOMER-MIXTURE METAL COMPLEX COMPOSITION, ORGANIC ELECTROLUMINESCENT ELEMENT, ILLUMINATOR, AND DISPLAY DEVICE

CROSS REFERENCE TO RELATED APPLICATIONS

This is the U.S. national stage of application No. PCT/JP2014/057676, filed on Mar. 20, 2014. Priority under 35 U.S.C. § 119(a) and 35 U.S.C. § 365(b) is claimed from Japanese Application No. 2013-072072, filed Mar. 29, 2013, the disclosure of which is also incorporated herein by reference.

TECHNICAL FIELD

The present invention relates to mixed isomeric metal complex compositions, organic electroluminescent metal complex compositions, organic electroluminescent elements, illuminators, and displays.

BACKGROUND ART

A typical organic electroluminescent element (hereinafter also referred to as "organic EL element") is composed of a cathode, an anode, and a luminous layer disposed therebetween and containing a luminous compound. Such an organic EL element can emit light by the following mechanism: An electric field applied to the organic EL element recombines holes injected from the anode with electrons injected from the cathode in the luminous layer to generate excitons, which are deactivated with luminescence (fluorescence and/or phosphorescence). The organic EL element is a completely solid element that includes submicron films disposed between the electrodes and composed of organic materials, and can emit light under an applied voltage of several volts to several tens of volts. Based on these advantages, it is expected that the organic EL elements will be applied to flat displays and lighting in the next generation.

Since Princeton University reported an organic EL element by phosphorescence from the excited triplet (for example, see Non-Patent Document 1), phosphorescent materials at room temperature have been extensively studied (for example, see Patent Document 1 and Non-Patent Document 1) to develop organic EL elements for practical use.

It has been already found that such phosphorescent compounds or complexes emit light beams of different color tones for various uses, that is, light beams of blue (B), green (G), and red (R) by varying their chemical structures, such as trisphenylpyridine iridium complexes described in J. Am. Chem. Soc., vol. 107, p. 1431 (1985), tris(phenylisoquinoline) iridium complexes described in J. Am. Chem. Soc., vol. 125, p. 12971 (2003), and tris(phenyltriazole) complexes described in Chem. Mater., vol. 18, p. 5119 (2006).

These phosphorescent complexes have their own emission spectra according to a difference in chemical structure. Unfortunately, original luminous colors unique to the respective chemical structures of the complexes are often not achieved due to agglomeration and/or crystallization of the complexes, which shifts the spectra to longer regions with broader distributions. To avoid such agglomeration and/or crystallization, the phosphorescent complexes are often dispersed in binders, or are used in combination with host compounds. These countermeasures, however, are not sufficiently effective, and still cause remarkable changes in color tone in the phosphorescent complexes during long-term use or at high temperatures.

The agglomeration and/or crystallization of the phosphorescent complex is fundamentally caused by the intensity of the interaction energy of the phosphorescent complex. The interaction balance with a co-existing host compound determines the state of the phosphorescent complex in a film, and this state varies over time to change the intensity of the interaction energy of the phosphorescent complex.

Such a disadvantage can be solved by formation of a stable film. The state of the film can be stabilized by a large negative Gibbs free energy of the film.

The Gibbs free energy is determined by enthalpy and entropy according to the second law of thermodynamics. Enthalpy is largely determined by a chemical structure intrinsic to a complex molecule, and cannot be readily varied. Entropy is determined by the number and distribution of components, and can be used as a universal technical variable factor.

This is rationally described from an entropy effect.

The entropy effect will be described with reference to the diagrams. FIG. 1A and FIG. 1B are a schematic view explaining an increase in entropy by mixing of two components. FIG. 1A illustrates a model of mixing of components A with components B. FIG. 1B is a model of mixing of components A with components A.

A reaction at constant pressure and low temperature has the following relationship among a change in Gibbs free energy ($\Delta G$), a change in enthalpy ($\Delta H$), and a change in entropy ($\Delta S$), which is represented by following Expression (1) where T represents absolute temperature.

$$\Delta G = \Delta H - T\Delta S \qquad \text{Expression (1):}$$

For example, assume that 2n phosphorescent organic metal complex molecules (component A) are present in a film. Assume that the film originally has a half of the 2n complex molecules (i.e., n complexes), and the other n complex molecules (component A) of the same type are added in the film so that the total number is 2n and the volume is doubled. At this time, the entropy change is zero because the complex added is the same as that originally present in the film (FIG. 1B). In contrast, if n complex molecules of a different type (component B) are added, the entropy of the complex originally present in the film (component A) increases because of the added complex molecules (component B) (FIG. 1A). This increase in entropy refers to an entropy effect. The increase in entropy causes the Gibbs free energy in the film to be more negative for stabilization, attaining a stable film over time. The entropy effect acts on such a basic principle.

This entropy effect caused by the "complex molecules of a different type" can attain both the stability of the film and interactive deactivation of it-planes to effectively prevent agglomeration over time of the complex mixture.

This phenomenon is found not only in the films but also in solutions of complexes. Namely, the schematic view in the right of FIG. 1A is also considered to illustrate a mixed solution of isomeric complexes, the isomeric complexes being completely dissolved or separately dispersed in a solvent. The Gibbs free energy of the solution or the thin film is negatively larger than that of a solution or powder composed of a single complex (corresponding to the right diagram in FIG. 1B), and changes caused by disturbance is reduced. In other words, agglomeration and/or recrystallization of the complexes is prevented.

This entropy effect attains dispersion of the complex during film formation by application of the solution of the mixed complexes to prevent changes in films over time and after electrical conduction. The entropy effect also enables the sublimation of the complex during sublimation purification or deposition, and sublimation of the complex in the form of a single molecule, enabling formation of films having a complex almost ideally dispersed (or nearly separately dispersed) therein.

An increase in entropy as described above is effectively attained by co-existing several luminous complexes. In co-existing several luminous complexes having different electronic states, however, electrons and holes (collectively referred to as charge carriers) are injected in different ways according to the types of complex molecules, and are preferentially injected into complex molecules to be most readily filled with charge carries. Such injection of charge carriers reduces the opportunity of recombination of charge carriers and in turn luminescence efficiency. This also shortens the luminance of the light emission over time and in turn the emission lifetime of the organic EL element.

The solution of such a problem requires mixing of as many compounds as possible, the compounds having different structures and having substantially the same level of the highest occupied molecular orbital (HOMO) and the lowest occupied molecular orbital (LUMO), and very close emission spectra and physical properties.

Such a requirement is satisfied by a heteroleptic complex (for example, see Patent Document 2) in which part of several ligands forming a complex is replaced with a ligand having a different structure. The heteroleptic complex moderates the crystallinity derived from a symmetric structure of a homoleptic complex to reduce growth of coarse crystals in the organic EL element. The heteroleptic complex, however, is readily agglomerated because the heteroleptic complex often has x-planes, which assist interaction between complex molecules and are present in the outermost region of the complex molecules.

PRIOR ART DOCUMENT

Patent Document

Patent Document 1: U.S. Pat. No. 6,097,147
Patent Document 2: U.S. Patent Application No. 2011/0057559

Non-Patent Document

Non-Patent Document 1: M. A. Baldo et al., Nature, vol. 403, No. 17, pp. 750-753 (2000)

SUMMARY OF INVENTION

Problem to be Solved by the Invention

The present invention has been made in consideration of these problems and circumstances. An object of the present invention is to provide a mixed isomeric metal complex composition containing atropisomers having very close physical properties and energy levels. Another object of the present invention is to provide an organic electroluminescent element including a luminous layer composed of the mixed isomeric metal complex composition as an organic electroluminescent material to enhance long-term stability of organic metal complexes in a film and reduce changes in resistance of the luminous layer and half width of the emission spectrum. A further object of the present invention is to provide an illuminator and a display including the organic electroluminescent element.

Means for Solving the Problem

The present inventor, who has conducted extensive research on the causes of the problems to be solved, has found the following universal technique of stabilizing a thin film: Several organic metal complexes having substantially equal or very close energy levels co-existing in a single thin film increase the entropy effect and then the Gibbs free energy becomes more negative, so that changes in physical properties are reduced in the electrically energized thin film, and has verified that this technique is applicable to organic EL elements.

The present inventor has also found that if the organic metal complexes are atropisomer and diastereoisomer components, these components inevitably have close energy levels, and several isomer metal complexes can be prepared through a single operation, and has achieved the present invention.

The problems of the present invention are solved by the following means:

1. A mixed isomeric metal complex composition comprising atropisomers, where in
each of the atropisomers comprises a metal atom and multiple ligands,
at least one of the ligands has an aromatic ring as a substituent, and
the atropisomers are present due to hindered free rotation of a bond axis between the aromatic ring and the at least one ligand after formation of a complex with the metal atom and the ligands.

2. The mixed isomeric metal complex composition according to Item 1, wherein the atropisomers are present due to hindered free rotation of the bond axis between the aromatic ring and the at least one ligand by another ligand in the complex.

3. An organic electroluminescent metal complex composition comprising the mixed isomeric metal complex composition comprising atropisomers according to Item 1 or 2, wherein the mixed isomeric metal complex composition is a phosphorescent material for organic electroluminescent elements.

4. The organic electroluminescent metal complex composition according to Item 3, the atropisomers being represented by Formula (1):

[Formula 1]

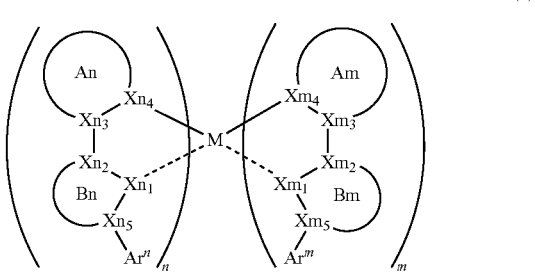

Formula (1)

where rings Am, An, Bm, and Bn each represent a 6-membered aromatic hydrocarbon ring or a 5-membered or 6-membered aromatic heterocycle, and optionally have a substituent; $Xm_1$, $Xm_2$, $Xm_3$, $Xm_4$, $Xm_5$, $Xn_1$, $Xn_2$, $Xn_3$, $Xn_4$, and $Xn_5$ in the rings Am, Bm, An, and Bn each represent a carbon atom or a nitrogen atom;

if $Xm_1$ and M and $Xn_1$ and M form coordination bonds, $Xm_4$ and M and $Xn_4$ and M form covalent bonds;

if $Xm_1$ and M and $Xn_1$ and M form covalent bonds, $Xm_4$ and M and $Xn_4$ and M form coordination bonds; and $Ar'''$ and $Ar''$ each represent an aromatic hydrocarbon ring or an aromatic heterocyclic group having no symmetrical axis in a bond axis to the ring Bm or Bn, and optionally have a substituent; M represents iridium or platinum; m and n each represent an integer of 0 to 3; m+n represents 2 or 3.

5. The organic electroluminescent metal complex composition according to Item 4, wherein the ring Bm, Bn, Am, or An in Formula (1) represents an imidazole or pyrazole ring.

6. The organic electroluminescent metal complex composition according to Item 4 or 5, wherein a ligand formed through bonding of the rings An and Bn or a ligand formed through the rings Am and Bm in Formula (1) is represented by Formula (2), (3), (5), or (6):

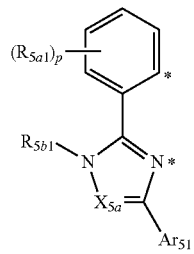

Formula (2)

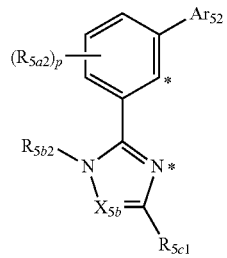

Formula (3)

where $R_{5a1}$ and $R_{5a2}$ each independently represent a halogen atom, a cyano group, an alkyl group, an alkenyl group, an alkynyl group, an alkoxy group, an amino group, a silyl group, an arylalkyl group, an aromatic hydrocarbon ring, an aromatic heterocyclic group, a non-aromatic hydrocarbon ring, or a non-aromatic heterocyclic group, and optionally have a substituent; p represents an integer of 0 to 4;

$R_{5b1}$, $R_{5b2}$, and $R_{5c1}$ represent an alkyl group, an aromatic hydrocarbon ring, an aromatic heterocyclic group, a non-aromatic hydrocarbon ring, or a non-aromatic heterocyclic group, and optionally have a substituent; $X_{5a}$ and $X_{5b}$ each independently represent $=C(R_{5e})-$ or $=N-$; $R_{5e}$ represents an alkyl group, an aromatic hydrocarbon ring, an aromatic heterocyclic group, a non-aromatic hydrocarbon ring, or a non-aromatic heterocyclic group;

$Ar_{51}$ and $Ar_{52}$ each independently represent an aromatic hydrocarbon ring represented by Formula (4):

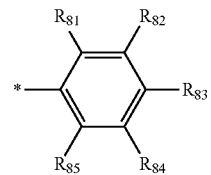

Formula (4)

where $R_{81}$ to $R_{85}$ each independently represent a hydrogen atom, a halogen atom, a cyano group, an alkyl group, an alkenyl group, an alkynyl group, an alkoxy group, an amino group, a silyl group, an arylalkyl group, an aryl group, a heteroaryl group, a non-aromatic hydrocarbon ring, or a non-aromatic heterocyclic group, and optionally have a substituent; two adjacent groups of $R_{81}$ to $R_{85}$ may bond to each other to form a ring; $R_{51}=R_{85}$ is incompatible with $R_{82}=R_{84}$;

* represents a bonding site to a metal atom;

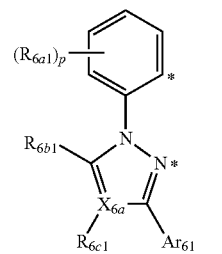

Formula (5)

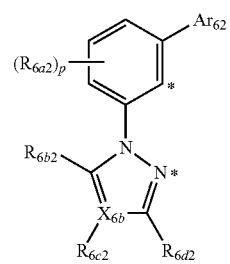

Formula (6)

where $R_{6a1}$ and $R_{6a2}$ each independently represent a halogen atom, a cyano group, an alkyl group, an alkenyl group, an alkynyl group, an alkoxy group, an amino group, a silyl group, an arylalkyl group, an aromatic hydrocarbon ring, an aromatic heterocyclic group, a non-aromatic hydrocarbon ring, or a non-aromatic heterocyclic group, and optionally have a substituent; q represents an integer of 0 to 4;

$R_{6b1}$, $R_{6c1}$, $R_{6b2}$, $R_{6c2}$, and $R_{6d2}$ each independently represent a hydrogen atom, an alkyl group, an aromatic hydrocarbon ring, an aromatic heterocyclic group, a non-aromatic hydrocarbon ring, or a non-aromatic heterocyclic group, and optionally have a substituent; $X_{6a}$ and $X_{6b}$ each independently represent $=C(R_{6e})-$ or $=N-$; $R_{6e}$ represents an alkyl group, an aromatic hydrocarbon ring, an aromatic heterocyclic group, a non-aromatic hydrocarbon ring, or a non-aromatic heterocyclic group;

$Ar_{61}$ and $Ar_{62}$ are the same as $Ar_{51}$ and $Ar_{52}$ in Formulae (2) and (3), and each represent an aromatic hydrocarbon group represented by Formula (4); and

* represents a bonding site to a metal atom.

7. The organic electroluminescent metal complex composition according to any one of Items 4 to 6, wherein M represents an iridium atom.

8. An organic electroluminescent element including a pair of electrodes, and one or more organic layers disposed between the pair of electrodes, wherein one of the organic layers contains the organic electroluminescent metal complex composition according to any one of Items 3 to 7.

9. The organic electroluminescent element according to Item 8, wherein the one organic layer contains a mixture of the organic electroluminescent metal complex composition and a host compound having a freely rotating biaryl structure.

10. The organic electroluminescent element according to Item 9, wherein the host compound having a freely rotating biaryl structure has a dibenzofuran structure.

11. The organic electroluminescent element according to Item 9, wherein the host compound having a freely rotating biaryl structure has a carbazole structure.

12. The organic electroluminescent element according to Item 9, wherein the host compound having a freely rotating biaryl structure has an unsubstituted phenyl group.

13. An illuminator including the organic electroluminescent element according to any one of Items 8 to 12.

14. A display including the organic electroluminescent element according to any one of Items 8 to 12.

Effects of Invention

The present invention provides a mixed isomeric metal complex composition comprising atropisomers having very close physical properties and energy levels. The present invention also provides an organic electroluminescent element including a luminous layer composed of the mixed isomeric metal complex composition as an organic electroluminescent material to enhance long-term stability of organic metal complexes in a film and reduce changes in resistance of the luminous layer and half width of an emission spectrum. The present invention further provides an illuminator and a display including the organic electroluminescent element.

Although mechanisms of advantageous effects and action of the present invention have not been clarified, the prevent inventor infers as follows.

In the present invention, a plurality of isomers having high similarities, derived from an atropisomeric axis, in physical properties, states of electrons in HOMO and LUMO, and emission spectra co-exist to attain the entropy effect. The entropy effect seems to reduce solubility in a solvent and interaction through n-planes of aromatic rings in complex molecules without a reduction in the emission lifetime, attaining more stable dispersion of complexes.

DESCRIPTION OF EMBODIMENTS

Figure 1A:
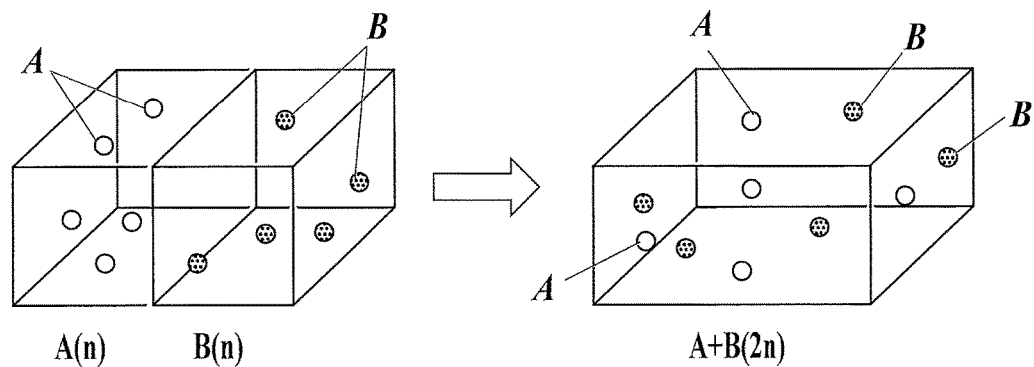
FIG. 1A is a schematic view for explaining an increase in entropy (model of mixing of components A with components B).
Figure 1B:
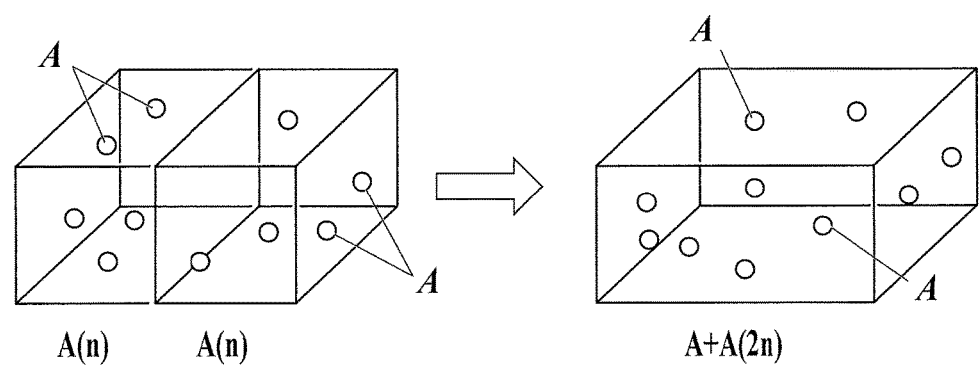
FIG. 1B is a schematic view for explaining an increase in entropy (model of mixing of components A with components A).

The mixed isomeric metal complex composition according to the present invention comprises atropisomers, wherein each of the atropisomers comprises a metal atom and multiple ligands, at least one of the ligands has an aromatic ring as a substituent, and the atropisomers are present due to hindered free rotation of a bond axis between the aromatic ring and the at least one ligand after formation of a complex with the metal atom and the ligands. These technical features are common to Items 1 to 14 in the invention.

In one embodiment of the mixed isomeric metal complex composition according to the present invention, the atropisomers are preferably present due to hindered free rotation of the bond axis between the at least one ligand and the aromatic ring by another ligand in the complex molecules to achieve the advantageous effects of the present invention. The mixed isomeric metal complex composition is preferably a phosphorescent material for organic EL elements.

In the present invention, the atropisomer is preferably represented by Formula (1). In Formula (1), rings Bm, Bn, Am, and An each preferably represent an imidazole or pyrazole ring.

In Formula (1), the ligand formed through bonding of the rings An and Bn or the ligand formed through bonding of the rings Am and Bm is preferably represented by Formula (2), (3), (5), or (6). M preferably represents an iridium atom, which allows a large number of atropisomers and/or diastereoisomers to co-exist in the organic electroluminescent metal complex composition.

An organic electroluminescent element includes a pair of electrodes, and one or more organic layers disposed between the pair of electrodes, wherein one of the organic layers preferably contains the organic electroluminescent metal complex composition.

One of the organic layers preferably contains a mixture of the organic electroluminescent metal complex composition and a host compound having a freely rotating biaryl structure. The host compound having a freely rotating biaryl structure preferably has a dibenzofuran structure, a carbazole structure, or an unsubstituted phenyl group.

The organic EL element according to the present invention is suitably included in illuminators and displays.

The present invention, components, and embodiments and aspects of the present invention will now be described in detail. Throughout the specification, the term "to" between numeric values indicates that the numeric values before and after the term are inclusive as the lower limit and the upper limit, respectively.

The present invention will now be described.

The enantiomer and the diastereoisomer will now be described in detail.

Typical examples of the chiral compounds include an asymmetric carbon compound (I) having a carbon atom (or an atom having unpaired electrons, such as nitrogen, sulfur, or phosphorus) with four different substituents; a so-called axially chiral compound (II) having a bulky substituent, such as a biaryl group, at its ortho-position through a bond axis (atropisomeric axis) to carry rotamerism; a planarly chiral compound (III) having aromatic rings with fixed or irrotational planes; a helical compound (IV) having specified directions of a twist, such as helicene; and a compound having isomers which are asymmetric mirror images generated after formation of a complex.

The enantiomers or mirror image isomers exhibit mirror images, such as human left and right hands. Isomers in such a mirror-image relationship are found not only in the asymmetric carbon compounds but also in compounds [II], [III], and [IV] and other chiral substances. These compounds can also be referred to as enantiomers.

Figure 9A:
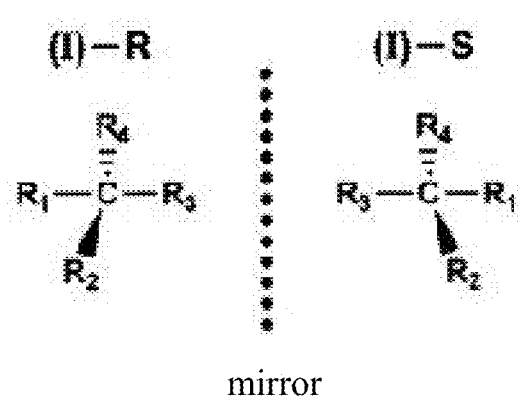
FIG. 9A and FIG. 9B are schematic views of two different compound enantiomers.
Figure 9B:
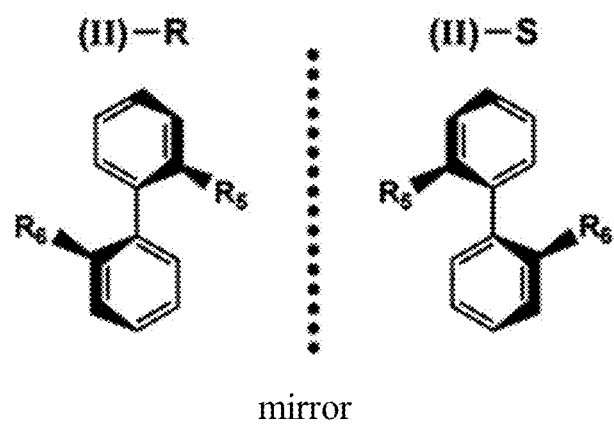

Examples of enantiomers are illustrated in FIG. 9A and FIG. 9B.

Figure 10:
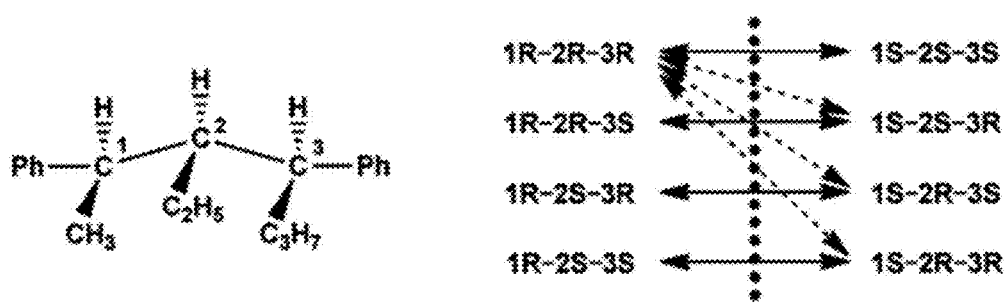
FIG. 10 is a schematic view of a diastereoisomer compound having three asymmetric carbons.

The diastereoisomers refer to molecules which have the same planar molecular formula but no mirror-image relationship and exhibit chirality if two or more chiral moieties are present. In other words, these molecules have a diastereoisomeric relationship. FIG. 10 is an example of a compound having three asymmetric carbons. The compound has eight isomers. Four pairs of isomers in a mirror-image relationship are enantiomes, and the other pairs are diastereoisomers. Each solid line with double-sided arrows indicates an enantiomeric relationship. Each dotted line with double-sided arrows indicates a diastereoisomeric relationship.

Figure 11:
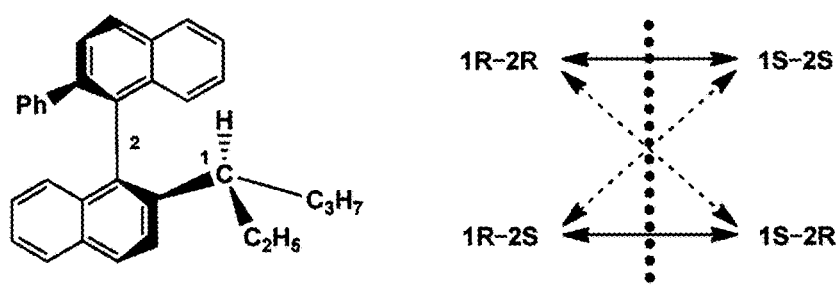
FIG. 11 is a schematic view of a compound having one chiral axis and one asymmetric carbon.

A specific example of a compound having one chiral axis and one asymmetric carbon is shown in FIG. 11. In fact, any type of chiralities can be used in combination. Each solid line with double-sided arrows indicates an enantiomeric relationship. Each dotted line with double-sided arrows indicates a diastereoisomeric relationship.

In a complex having several ligands, for example, a trivalent hexa-coordinated iridium complex, one chiral ligand generates several chiral complex molecules, and in turn diastereoisomers.

If n chiral moieties are present, $2^n$ isomers are usually present (n: integer). Any chiral moiety can be used. A compound having three chiral moieties has eight isomers, and a compound having four chiral moieties has sixteen isomers.

In the present invention, atropisomers refer to stereoisomers generated by hindered rotation of a ligand forming a metal complex, which is caused by steric hindrance or interaction between an aryl substituent group included in a ligand skeleton bonded to a metal of the metal complex and another ligand in the same complex molecule including the ligand skeleton.

This technical concept of the present invention will now be described.

Figure 12:
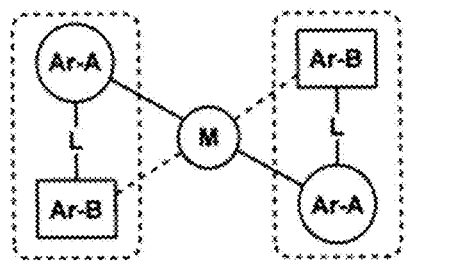
FIG. 12 is a schematic view of an ortho-metalated complex having a metal atom coordinated with two bidentate ligands.

Scheme 1 in FIG. 12 illustrates a schematic view of an ortho-metalated complex having a metal atom (coordination number: 4) coordinated with two bidentate ligands. In FIG. 12, M is a metal ion, L is a bond or linking group, Ar and Ar is an aromatic group. Each ligand is composed of two aromatic rings Ar-A and Ar—B bonded to each other directly or through a linking group (L).

Figure 13:
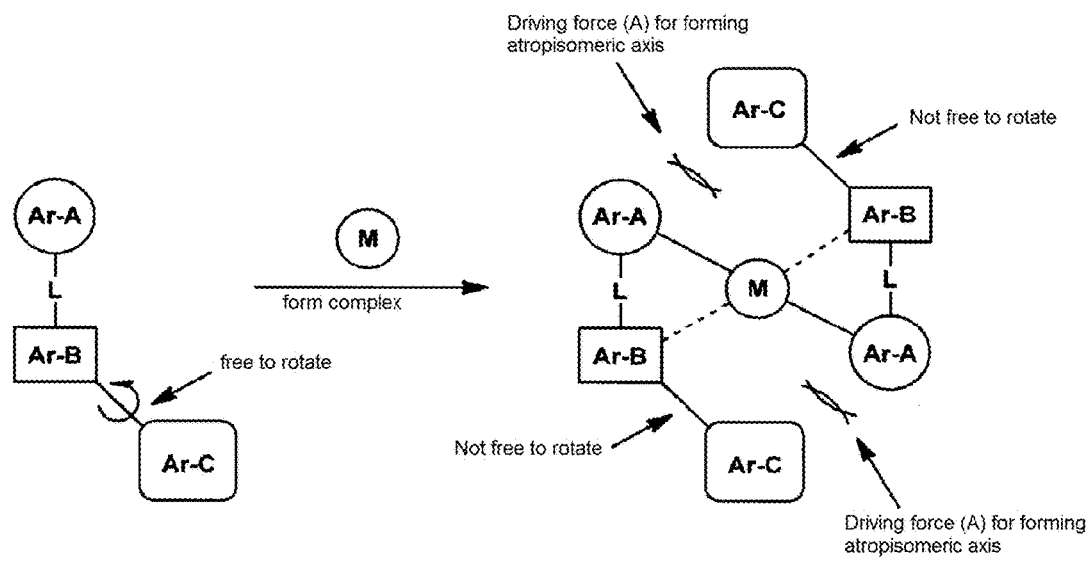
FIG. 13 is a schematic view of an example complex having atropisomers generated during formation of the mixed isomeric metal complex composition according to the present invention.

Scheme 2 in FIG. 13 is shown to describe an example complex having atropisomers generated during formation of the mixed isomeric metal complex composition according to the present invention (also referred to as complex according to the present invention). As shown in Scheme 2, a ligand before formation of a complex has a partial structure for forming a complex, i.e., aromatic rings Ar-A and Ar-B, and another aromatic ring Ar-C having a freely rotating single bond with the partial structure. After formation of a complex with a metal ion, this ligand is no longer free to rotate due to hindrance by another ligand of the complex molecule (Ar-A in the scheme) rather than the ligand itself, so that the single bond serves as an atropisomeric axis.

It has been found that the it-plane of the aromatic ring Ar-C in this complex is no longer free to rotate due to such a hindrance effect of the aromatic ring Ar-A in another ligand (stereoscopic shielding effect (repulsion) and/or n-n stacking or an association effect (attractive force) of dipoles) so that at least one x-plane can be interactively deactivated to effectively prevent agglomeration of the complex.

In Scheme 2 shown in FIG. 13, the bond between the aromatic rings Ar-B and Ar—C is no longer free to rotate after formation of the complex to produce a driving force (A), and serves as an atropisomeric axis. The present invention also includes complexes having an aromatic ring Ar-C bonded to an aromatic ring Ar-A, the bond between the aromatic rings Ar-B and Ar-C being no longer free to rotate after formation of the complex to serve as an atropisomeric axis.

Figure 14:
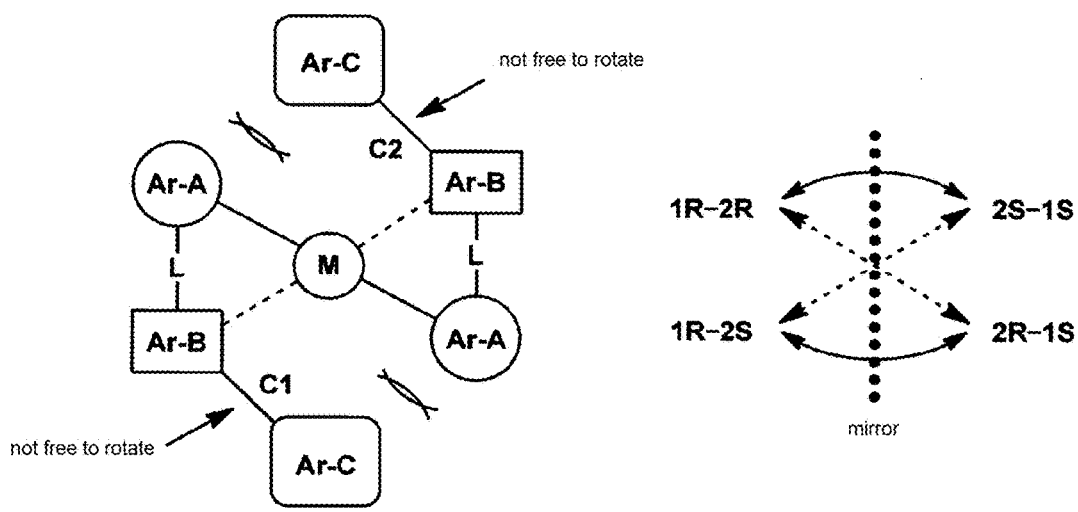
FIG. 14 is a schematic view of an exemplary complex according to the present invention having a tetra-coordinated metal in the center.

In Scheme 3 shown in FIG. 14, an exemplary complex according to the present invention having a tetra-coordinated metal in the center will be described. Specifically, in a complex composed of a tetra-coordinated metal, enantiomers and diastereoisomers generated by the atropisomeric axis will be described. As illustrated in Scheme 3, the complex according to the present invention has two enantiomers per ligand because the bond between the aromatic rings Ar-B and Ar—C is not free to rotate. These enantiomers are in a mirror-image relationship, and are not superimposable. Two enantiomers are generated due to the hindered rotation of the bond axis C1 of one ligand. These enantiomers are referred to as 1R and 1S. Two different enantiomers are generated due to the hindered rotation of the bond axis C2 of another ligand. These enantiomers are referred to as 2R and 2S. The ligands each have two enantiomers, and thus four stereoisomers (2×2=4) are present. Of the four stereoisomers, those having a mirror-image relationship and not superimposable are enantiomers, and those not having a mirror-image relationship and not superimposable are diastereoisomers. In Scheme 3, two enantiomers and two diastereoisomers are present. The solid line with double-sided arrows indicates an enantiomeric relationship. The dotted line with double-sided arrows indicates a diastereoisomeric relationship.

Figure 15A:
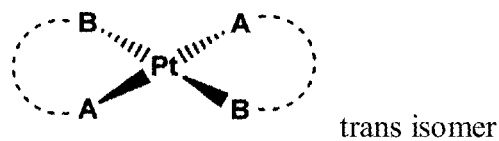
FIG. 15A is a schematic view of a trans isomer.
Figure 15B:
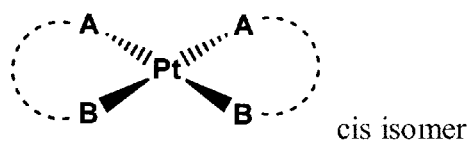
FIG. 15B is a schematic view of a cis isomer.

A square planar complex composed of a metal M (such as Pt(II)) having a coordination number of 4 and a bidentate ligand and represented by a general composition M(A-B)$_2$ (where A-B represents a bidentate ligand) has "cis/trans isomers":

FIG. 15A is an illustration of a trans isomer and FIG. 15B is an illustration of a cis isomer.

In a complex represented by a general composition M(A-B)$_2$, the cis isomerism indicates that two identical groups (i.e., groups A or B) are disposed on adjacent corners of a square, while the trans isomerism indicates that two identical groups (i.e., groups A or B) are diagonally disposed. The definition of the cis/trans isomers of a square planar metal complex is found in J. Huheey, E. Keiter, R. Keiter, Anorganische Chemie: Prinzipien von Struktur und Reaktivitaet, 2nd, newly revised edition, translated into German and expanded by Ralf Steudel, Berlin; New York: de Gruyter, 1995, pp. 557-559, for example.

In general, the cis/trans isomers often have different emission spectra, different physical properties, such as the stability of a compound, and different electronic states, and are excluded from the isomer specified in the mixed isomeric metal complex composition according to the present invention. The cis/trans isomers have different stabilities according to the type of ligands. Accordingly, it is presumed that the complex according to the present invention includes only one of the cis/trans isomers of the tetradentate square metal complex.

Figure 16A:
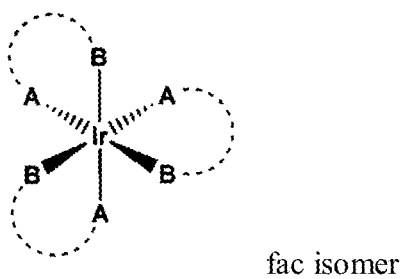
FIG. 16A is a schematic view of a fac isomer and FIG. 16B is an illustration of a mer isomer.
Figure 16B:
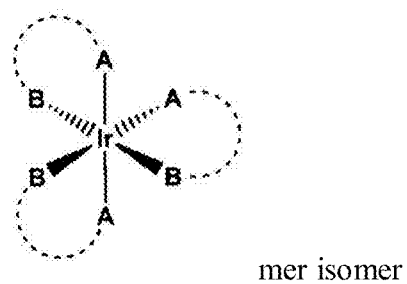

An exemplary complex according to the present invention composed of a hexa-coordinated metal in the center will now be described. A complex having a metal M with a coordination number of 6 (namely, octahedral complex), such as an Ir(III) complex, and represented by a general composition M(A-B)$_3$ (where AB represents a bidentate ligand) has a facial or fac isomer and a meridional or mer isomer:

FIG. 16A is a schematic view of a fac isomer and FIG. 16B is a schematic view a mer isomer.

The definitions of cis/trans isomers and fac/mer isomers in an octahedral metal complex are found in J. Huheey, E. Keiter, R. Keiter, Anorganische Chemie: Prinzipien von Structur und Reaktivitaet [Inorganic Chemistry: Principles of Structure and Reactivity], 2nd, newly revised edition, translated into German and expanded by Ralf Steudel, Berlin; New York: de Gruyter, 1995, pp. 575-576, for example.

In general, facial/meridional isomers often have different emission spectra, different physical properties, such as the stability of a compound, and different electronic states, and are excluded from the isomer specified in the mixed isomeric complex composition according to the present invention. The facial isomers are thermodynamically more stable than meridional isomers. Accordingly, it is presumed that facial isomers of hexadentate octahedral metal complexes are included in the present invention.

A regular octahedral complex coordinated with a bidentate ligand has a Δ (delta) enantiomer and a Λ (lambda) enantiomer (corresponding to a clockwise propeller and a counterclockwise propeller, respectively) in a mirror image relationship.

Figure 17:
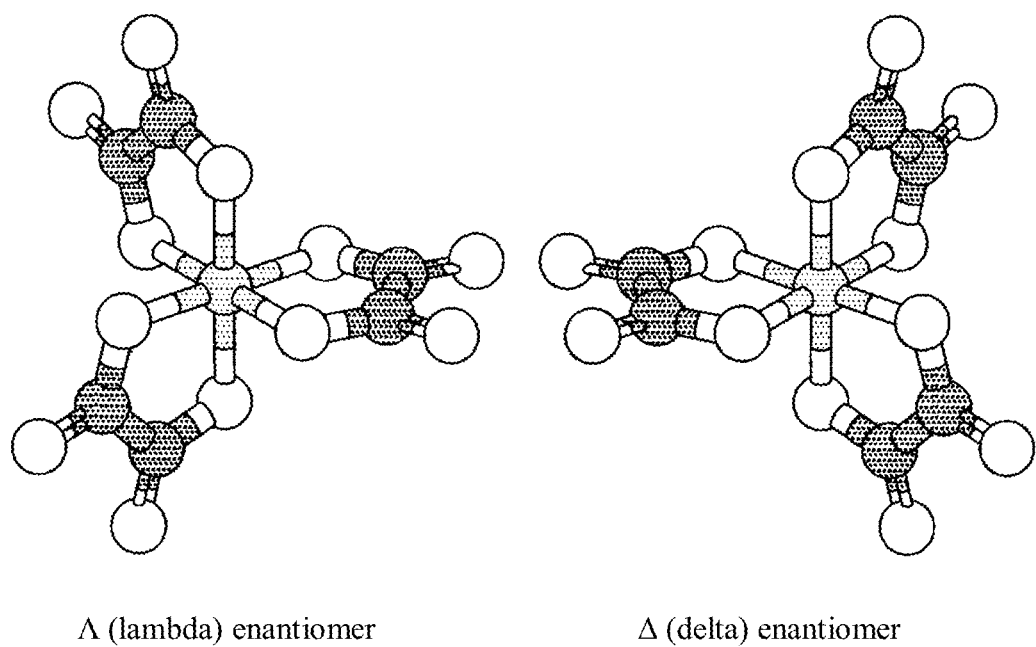
FIG. 17 is a schematic view of a Λ (lambda) enantiomer and Δ (delta) enantiomer.

FIG. 17 is a schematic view of a Λ (lambda) enantiomer and Δ (delta) enantiomer.

Figure 18:
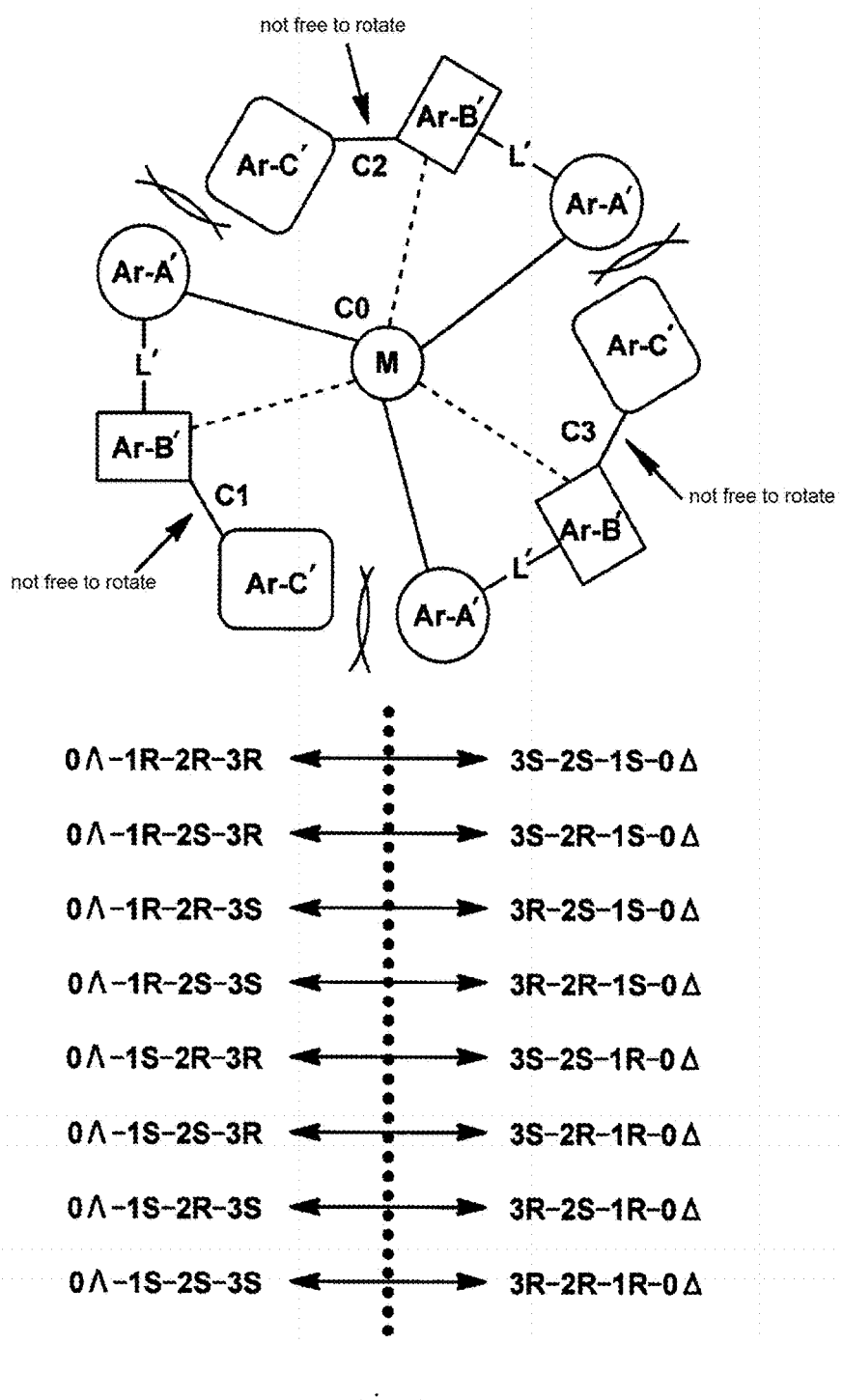
FIG. 18 is an exemplary complex according to the present invention having a hexa-coordinated metal in the center.

In Scheme 4 shown in FIG. 18, an exemplary complex according to the present invention having a hexa-coordinated metal in the center will now be described. A metal complex composed of a hexa-coordinated central metal has a stereoscopic structure composed of the metal disposed in the center of a regular octahedron and atoms coordinated with the metal at the respective vertices of the octahedron.

Although not clear in Scheme 4, the Ar-C' plane in one ligand is close to the Ar-B plane in another ligand in the same complex molecule to hinder the free rotation of the bond between the aromatic rings Ar-B' and Ar-C' after formation of the complex. As in a complex composed of a tetra-coordinated central metal, this complex composed of a hexa-coordinated central metal has two diastereoisomers due to hindered free rotation of one ligand. A complex composed of a coordinate central metal has three ligands, and then has eight (2×2×2=8) diastereoisomers and enantiomers.

A complex composed of a hexa-coordinated metal coordinated with a bidentate ligand further has two isomers, i.e., a Λ (lambda) isomer and a Δ (delta) isomer, and has 16 isomers in total. Such a complex has a larger effect of increasing entropy, that is, a larger effect of stabilizing the state of the film than that of the complex composed of a tetra-coordinated central metal. Accordingly, the complex according to the present invention is preferably composed of a central metal Ir. The solid line with arrows indicates an enantiomeric relationship.

According to the technical concept and the basic principle of the present invention, the entropy effect increases as the number of the atropisomeric axes increases. A larger entropy effect is readily attained in heteroleptic complexes with hexadentate coordination, such as iridium complexes, in which one of three ligands has a different chemical structure.

Figure 19:
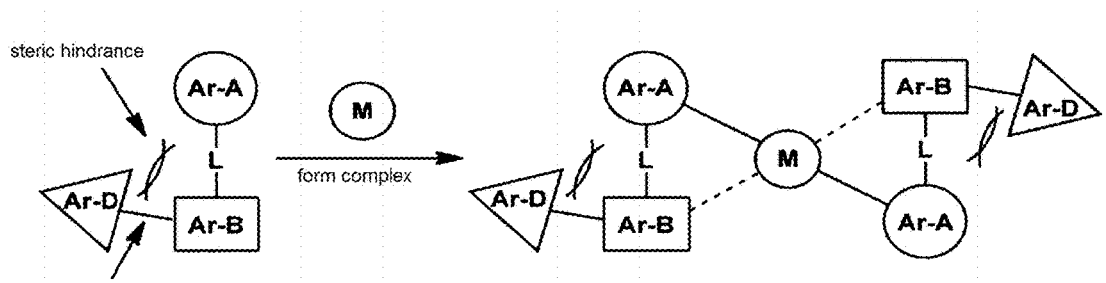
FIG. 19 is a schematic view of a complex composed of a ligand originally having an atropisomeric axis.

Complexes are known which are composed of a ligand originally having an atropisomeric axis, such as a ligand and a complex shown in Scheme 5 in FIG. 19. For example, WO 2007/097149 discloses Exemplified compound (170) composed of a ligand in which an imidazole ring corresponds to an aromatic ring Ar-B, a phenyl group at position 2 of the imidazole ring corresponds to an aromatic ring Ar-A in Scheme 5, and a 2-phenyl-6-methylphenyl group at position 1 of the imidazole ring corresponds to an aromatic Ar-D. This ligand has hindered rotation in a single bond between position 1 of the imidazole group and the phenyl group bonded to position 1 of the imidazole group, and then has atropisomers. In this case, however, free rotation of the aromatic ring Ar-D carrying atropisomerism is originally hindered due to an effect of steric hindrance between the aromatic rings Ar-B and Ar-D in the ligand rather than after formation of the complex. Accordingly, these complexes are excluded from the complex according to the present invention.

In such complexes, the Ar-D plane is outwardly projected from the center of the complex molecule, and can approach to another aromatic ring of the complex molecule. These complexes, however, insufficiently moderate the agglomeration of the complexes, and some of those having specific chemical structures may actively promote the interaction, i.e., agglomeration between the aromatic rings Ar-D, resulting in complexes having noticeable instability in the form of a film and significantly low solubility compared to those of the complex according to the present invention.

Figure 20:
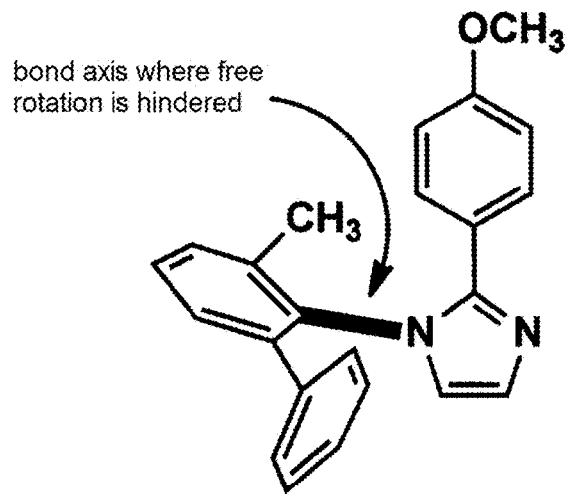
FIG. 20 is a schematic view of Exemplified compound (170) showing the bond axis where free rotation is hindered.

The ligand of Exemplified compound (170) described in WO 2007/097149 is shown in FIG. 20.

In contrast, the skeleton ligand in the complex according to the present invention is disposed close to the aryl substituent group to reduce interaction between the π-planes of aromatic rings of the complex molecules. The complex according to the present invention comprises a mixture of enantiomers and diastereoisomers to enhance the stability of the complex in a film and the solubility thereof.

Indeed, known patent documents and technical articles happen to describe complex structures which may satisfy the requirements of the present invention. For example, Japanese Unexamined Patent Application Publication (Tokuhyo) No. 2011-500644 describes a compound having a specific chemical structure. Although no specific description is found on their isomers, the chemical structure seems to suggest the existence of these isomers in view of two or more atropisomeric axes that are formed during formation of a complex. This specification, however, never describes intended use of a mixture of enantiomers and diastereoisomes of the compound, and has technical concept different from that of the present invention.

The contents disclosed in that patent document implies that single use of the compound written on the document can improve the emission lifetime and the color tones of an organic EL element, and apparently are different from that of the present invention.

Japanese Unexamined Patent Application Publication (Tokuhyo) No. 2008-525995 discloses an organic electronic device containing atropisomers generated due to hindered free rotation of a carbon-carbon bond. The compound generating atropisomers is a fluorescent material composed of a main skeleton of anthracene, pyrene, or chrysene. This patent document does not disclose the phosphorescent transition metal complex of the present invention, and uses excess amounts of preferred atropisomers selected from atropisomers having significantly different physical properties (referred to as syn- and anti-isomers in this document). Apparently, the technical concept is different from those of the present invention.

The skeleton of the complex according to the present invention should be bonded to an aromatic ring having no symmetrical axis.

The aromatic ring having no symmetrical axis refers to an aromatic ring having a shape not identical to the shape of the aromatic ring 180° rotated about the bond axis bonded to the complex skeleton. In other words, this aromatic ring has no twofold symmetrical axis.

Such an aromatic ring will be described by comparison between a 3-tolyl group and a 3,5-xylyl group. A 180° rotation about the bond axis bonded to the complex skeleton gives different shapes of a 3-tolyl group and identical shapes of a 3,5-xylyl group.

A partial structure composed of such an aromatic ring having no symmetrical axis is required to exhibit atropisomerism of the present invention due to hindered rotation of the bond axis after formation of a complex.

Figure 21A:
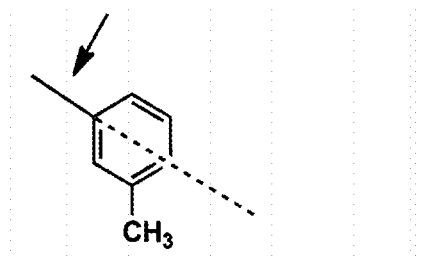
FIG. 21A shows a partial structure composed of an aromatic ring having no symmetrical axis.
Figure 21B:
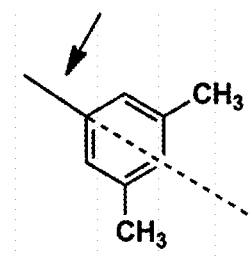
FIG. 21B shows a partial structure composed of an aromatic ring having a symmetrical axis.

FIG. 21A shows a partial structure composed of an aromatic ring having no symmetrical axis, and corresponds to $Ar^m$, $Ar^n$, $Ar^{m'}$ and $Ar^{n'}$ of the present invention. FIG. 21B shows a partial structure composed of an aromatic ring having a symmetrical axis, and does not correspond to $Ar^m$, $Ar^n$, $Ar^{m'}$ and $Ar^{n'}$ of the present invention.

The ortho-metalated complex according to the present invention to form an atropisomeric axis after formation of the complex (mixed isomeric metal complex composition) preferably has a structure represented by Formula (1):

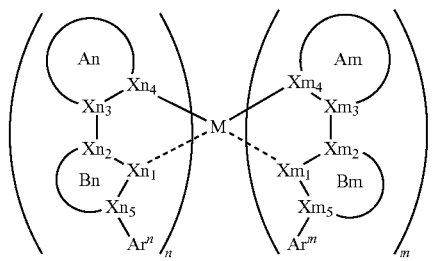

Formula (1)

where rings Am, An, Bm, and Bn each represent a 6-membered aromatic hydrocarbon ring or a 5-membered or 6-membered aromatic heterocycle, and optionally have a substituent; $Xm_1$, $Xm_2$, $Xm_3$, $Xm_4$, and $Xm_5$ in the rings Am and Bm each represent a carbon atom or a nitrogen atom; $Xn_1$, $Xn_2$, $Xn_3$, $Xn_4$, and $Xn_5$ in the rings An and Bn each represent a carbon atom or a nitrogen atom;

if $Xm_1$ and M and $Xn_1$ and M form coordination bonds, $Xm_4$ and M and $Xn_4$ and M form covalent bonds;

if $Xm_1$ and M and $Xn_1$ and M form covalent bonds, $Xm_4$ and M and $Xn_4$ and M form coordination bonds;

$Ar^m$ and $Ar^n$ each represent an aromatic hydrocarbon ring or an aromatic heterocyclic group having no symmetrical axis in a bond axis to the ring Bm or Bn, and optionally have a substituent; M represents Ir or Pt;

m and n each represent an integer of 0 to 3; m+n represents 2 or 3.

Examples of the 6-membered aromatic hydrocarbon ring or the 5-membered or 6-membered aromatic heterocycle represented by Am, An, Bm, and Bn in Formulae (1) and (2) include benzene, oxazole, oxadiazole, thiophene, thiazole, isothiazole, thiadiazole, furan, pyrrole, pyridine, pyridazin, pyrimidine, pyrazine, diazine, triazine, imidazole, pyrazole, triazole, and tetrazole rings.

Non-limiting examples of the 6-membered aromatic hydrocarbon rings or the 5-membered or 6-membered aromatic heterocycles represented by Am, An, Bm, and Bn are shown in Formulae A-1 to A-53 and B-1 to B-13:

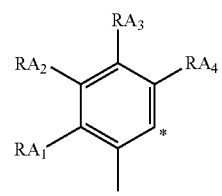

A-1

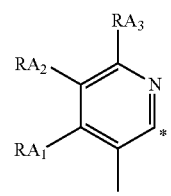

A-2

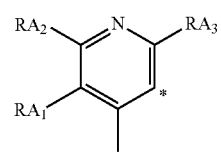

A-3

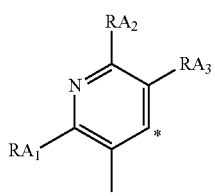 A-4
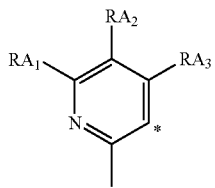 A-5
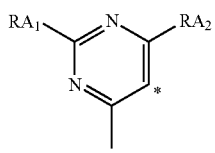 A-6
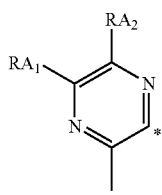 A-7
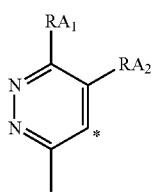 A-8
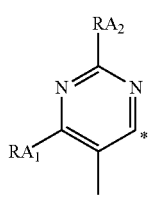 A-9
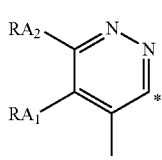 A-10
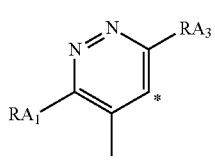 A-11
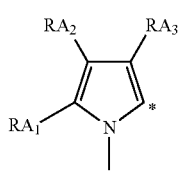 A-12
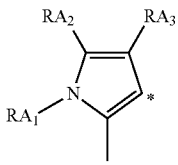 A-13
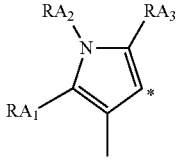 A-14
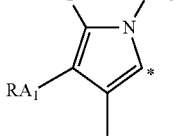 A-15
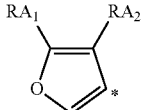 A-16
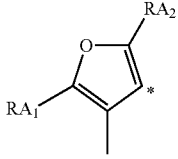 A-17
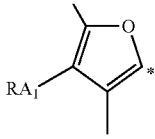 A-18
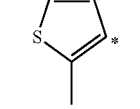 A-19
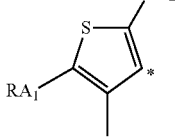 A-20
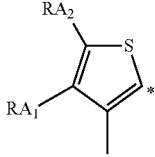 A-21

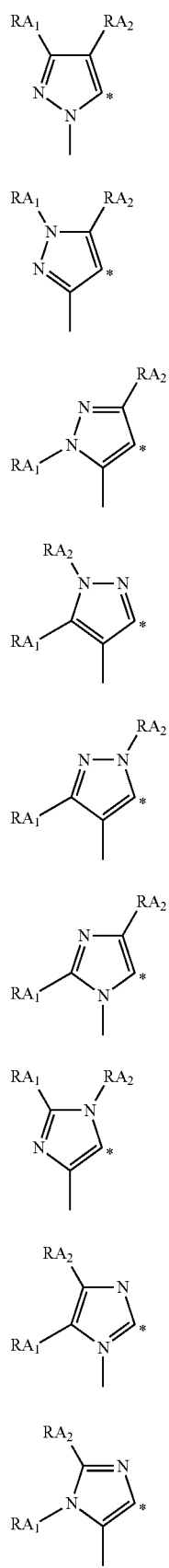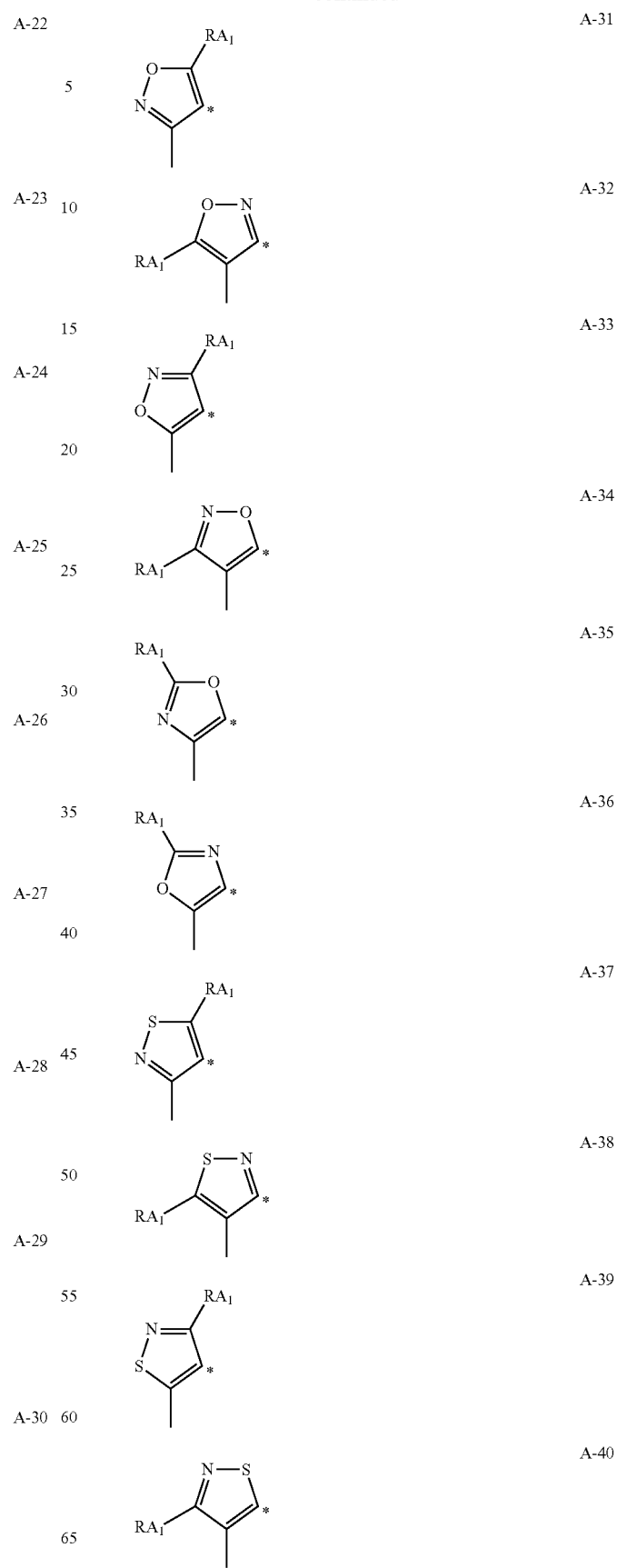

-continued
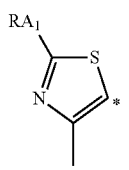 A-41
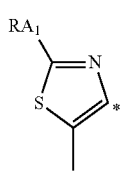 A-42
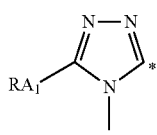 A-43
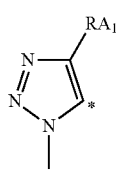 A-44
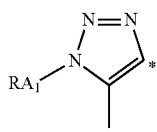 A-45
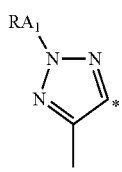 A-46
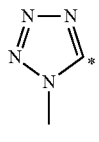 A-47
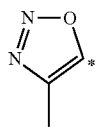 A-48
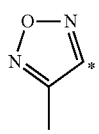 A-49
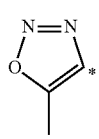 A-50
-continued
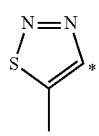 A-51
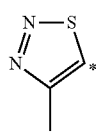 A-52
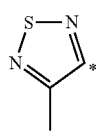 A-53
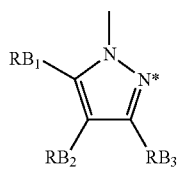 B-1
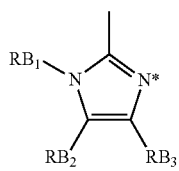 B-2
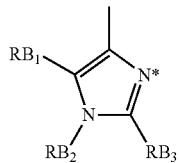 B-3
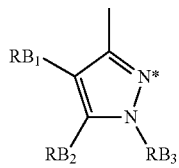 B-4
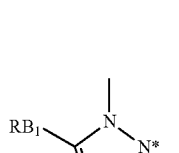 B-5
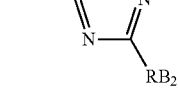 
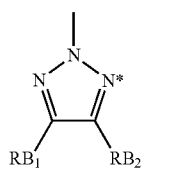 B-6

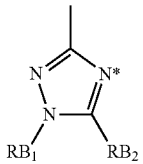

B-7

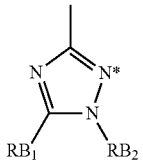

B-8

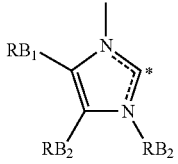

B-9

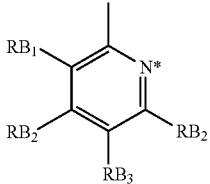

B-10

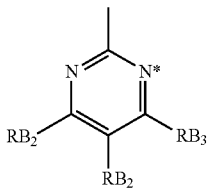

B-11

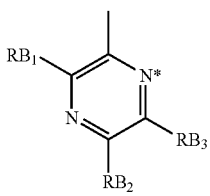

B-12

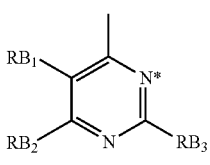

B-13

In Formulae A-1 to A-53 and B-1 to B-13, * indicates a bonding site to a transition metal element M.

In Formulae A-1 to A-53, $RA_1$, $RA_2$, $RA_3$, and $RA_4$ each represent a hydrogen atom or a substituent. Examples of the substituent include alkyl groups (such as methyl, ethyl, propyl, isopropyl, tert-butyl, pentyl, hexyl, octyl, dodecyl, tridecy, tetradecyl, and pentadecyl groups); cycloalkyl groups (such as cyclopentyl and cyclohexyl groups); alkenyl groups (such as vinyl and allyl groups); alkynyl groups (such as ethynyl and propargyl groups); aromatic hydrocarbon rings (also referred to as aromatic carbon rings or aryl groups, such as phenyl, p-chlorophenyl, mesityl, tolyl, xylyl, naphthyl, anthryl, azulenyl, acenaphthenyl, fluorenyl, phenanthryl, indenyl, pyrenyl, and biphenylyl groups); aromatic heterocyclic groups (such as pyridyl, pyrimidinyl, furyl, pyrrolyl, imidazolyl, benzoimidazolyl, pyrazolyl, pyrazinyl, triazolyl (such as 1,2,4-triazol-1-yl and 1,2,3-triazol-1-yl), oxazolyl, benzooxazolyl, thiazolyl, isooxazolyl, isothiazolyl, furazanyl, thienyl, quinolyl, benzofuryl, dibenzofuryl, benzothienyl, dibenzothienyl, indolyl, carbazolyl, carbolinyl, diazacarbazolyl (the carbolinyl group having a carboline ring in which one of carbon atoms is replaced with a nitrogen atom), quinoxalinyl, pyridazinyl, triazinyl, quinazolinyl, and phthalazinyl groups); heterocyclic groups (such as pyrrolidyl, imidazolydyl, morpholyl, and oxazolydyl groups); alkoxy groups (such as methoxy, ethoxy, propyloxy, pentyloxy, hexyloxy, octyloxy, and dodecyloxy groups); cycloalkoxy groups (such as cyclopentyloxy and cyclohexyloxy groups); aryloxy groups (such as phenoxy and naphthyloxy groups); alkylthio groups (such as methylthio, ethylthio, propylthio, pentylthio, hexylthio, octylthio, and dodecylthio groups); cycloalkylthio groups (such as cyclopentylthio and cyclohexylthio groups); arylthio groups (such as phenylthio and naphthylthio groups); alkoxycarbonyl groups (such as methyloxycarbonyl, ethyloxycarbonyl, butyloxycarbonyl, octyloxycarbonyl, and dodecyloxycarbonyl groups); aryloxycarbonyl groups (such as phenyloxycarbonyl and naphthyloxycarbonyl groups); sulphamoyl groups (such as aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, and 2-pyridylaminosulfonyl groups); acyl groups (such as acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl); acyloxy groups (such as acetyloxy, ethylcarbonyloxy, butylcarbonyloxy, octylcarbonyloxy, dodecylcarbonyloxy, and phenylcarbonyloxy); amide groups (such as methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, and naphthylcarbonylamino groups); carbamoyl groups (such as aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, and 2-pyridylaminocarbonyl groups); ureido groups (such as methylureido, ethylureido, pentylureido, cyclohexylureido, octylureido, dodecylureido, phenylureidonaphthylureido, and 2-pyridylaminoureido groups); sulfinyl groups (such as methylsulfinyl, ethylsulfinyl, butylsulfinyl, cyclohexylsulfinyl, 2-ethylhexylsulfinyl, dodecylsulfinyl, phenylsulfinyl, naphthylsulfinyl, and 2-pyridylsulfinyl groups); alkylsulfonyl groups (such as methylsulfonyl, ethylsulfonyl, butylsulfonyl, cyclohexylsulfonyl, 2-ethylhexylsulfonyl, and dodecylsulfony groups); arylsulfonyl or heteroarylsulfonyl groups (such as phenylsulfonyl, naphthylsulfonyl, and 2-pyridylsulfonyl groups); amino groups (such as amino, ethylamino, dimethylamino, butylamino, cyclopentylamino, 2-ethylhexylamino, dodecylamino, anilino, naphthylamino, and 2-pyridylamino groups); halogen atoms (such as fluorine, chlorine, and bromine atoms); fluorohydrocarbon groups (such as fluoromethyl, trifluoromethyl, pentafluoroethyl, and pentafluorophenyl groups); a cyano group; a nitro group; a hydroxy group; a mercapto group; and silyl groups (such as trimethylsilyl, triisopropylsilyl, triphenylsilyl, and phenyldiethylsilyl groups).

In Formulae A-1 to A-53, two of $RA_1$, $RA_2$, $RA_3$, and $RA_4$ may bond to each other to form a ring.

Examples of the rings formed through bonding of two of $RA_1$, $RA_2$, $RA_3$, and $RA_4$ in Formulae A-1 to A-53 include naphthalene, tetralin, anthracene, phenanthrene, quinoline, isoquinoline, indole, benzofuran, benzothiophene, indazole, benzoimidazole, benzothiazole, benzooxazole, carbazole, dibenzofuran, dibenzothiophene, and benzotriazole rings.

In Formulae B-1 to B-13, * indicates a bonding site to a transition metal element M.

In Formulae B-1 to B-13, $RB_1$, $RB_2$, and $RB_3$ represent a hydrogen atom or a substituent. Examples of the substituent include the same substituents as those represented by $RA_1$ to $RA_4$ in Formulae A-1 to A-53.

In Formulae B-1 to B-13, two of $RB_1$, $RB_2$, and $RB_3$ may bond to each other to form a ring.

Examples of the rings formed through bonding of two of $RB_1$, $RB_2$, and $RB_3$ in Formulae B-1 to B-13 include the same rings as those formed through bonding of two of $RA_1$, $RA_2$, and $RA_3$ in Formulae A-1 to A-53.

In the complex according to the present invention, the ring represented by Bm or Bn in Formula (1) is preferably a pyrazole or imidazole ring.

In Formula (1), a ligand formed through bonding of the rings An and Bn or a ligand formed through bonding of the rings Am and Bm is preferably represented by Formula (2), (3), (5), or (6):

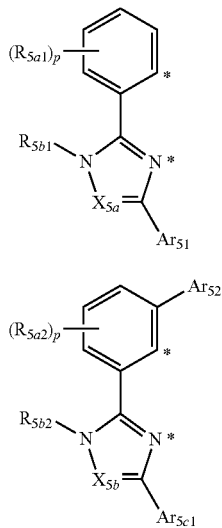

Formula (2)

Formula (3)

In Formulae (2) and (3), $R_{5a1}$ and $R_{5a2}$ each independently represent a halogen atom, a cyano group, an alkyl group, an alkenyl group, an alkynyl group, an alkoxy group, an amino group, a silyl group, an arylalkyl group, an aromatic hydrocarbon ring, an aromatic heterocyclic group, a non-aromatic hydrocarbon ring, or a non-aromatic heterocyclic group, and optionally have a substituent; p represents an integer of 0 to 4.

$R_{5b1}$ and $R_{5b2}$ represent an alkyl group, an aromatic hydrocarbon ring, an aromatic heterocyclic group, a non-aromatic hydrocarbon ring, or a non-aromatic heterocyclic group, and optionally have a substituent. $X_{5a}$ and $X_{5b}$ each independently represent $=C(R_{5e})-$ or $=N-$. $R_{5e}$ represents an alkyl group, an aromatic hydrocarbon ring, an aromatic heterocyclic group, a non-aromatic hydrocarbon ring, or a non-aromatic heterocyclic group;

$Ar_{51}$ and $Ar_{52}$ each independently represent an aromatic hydrocarbon ring represented by Formula (4):

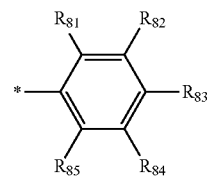

Formula (4)

$R_{81}$ to $R_{85}$ each independently represent a hydrogen atom, a halogen atom, a cyano group, an alkyl group, an alkenyl group, an alkynyl group, an alkoxy group, an amino group, a silyl group, an arylalkyl group, an aryl group, a heteroaryl group, a non-aromatic hydrocarbon ring, or a non-aromatic heterocyclic group, and optionally have a substituent. Two adjacent groups of $R_{81}$ to $R_{85}$ may bond to each other to form a ring. $R_{81}=R_{85}$ is incompatible with $R_{82}=R_{84}$.

In Formulae (2) and (3), * represents a bonding site to a metal atom.

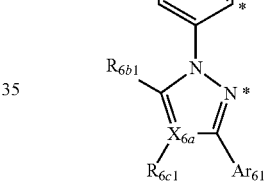

Formula (5)

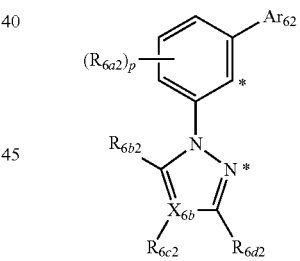

Formula (6)

In Formulae (5) and (6), $R_{6a1}$ and $R_{6a2}$ each independently represent a halogen atom, a cyano group, an alkyl group, an alkenyl group, an alkynyl group, an alkoxy group, an amino group, a silyl group, an arylalkyl group, an aromatic hydrocarbon ring, an aromatic heterocyclic group, a non-aromatic hydrocarbon ring, or a non-aromatic heterocyclic group, and optionally have a substituent; q represents an integer of 0 to 4.

$R_{6b1}$, $R_{6c1}$, $R_{6b2}$, $R_{6c2}$, and $R_{6d2}$ each independently represent a hydrogen atom, an alkyl group, an aromatic hydrocarbon ring, an aromatic heterocyclic group, a non-aromatic hydrocarbon ring, or a non-aromatic heterocyclic group, and optionally have a substituent. $X_{6a}$ and $X_{6b}$ each independently represent $=C(R_{6e})-$ or $=N-$. $R_{6e}$ represents an alkyl group, an aromatic hydrocarbon ring, an aromatic heterocyclic group, a non-aromatic hydrocarbon ring, or a non-aromatic heterocyclic group.

In Formulae (5) and (6), * represents a bonding site to an Ir atom. $Ar_{61}$ and $Ar_{62}$ are the same as $Ar_{511}$ and $Ar_{52}$ in Formulae (2) and (3), and represent an aromatic hydrocarbon group represented by Formula (4). In Formulae (5) and (6), * represents a bonding site to a metal atom.

Non-limiting specific examples of the complex according to the present invention are shown below:

Exemplified Compound 1

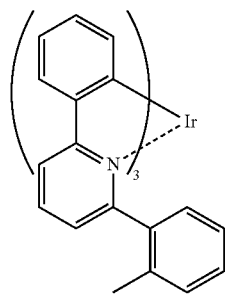

Exemplified Compound 2

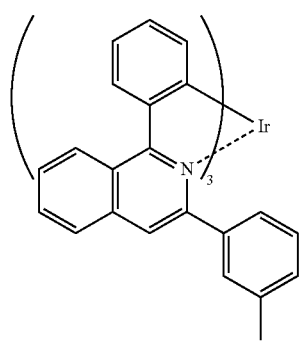

Exemplified Compound 3

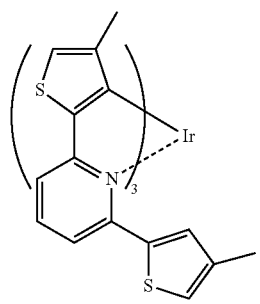

Exemplified Compound 4

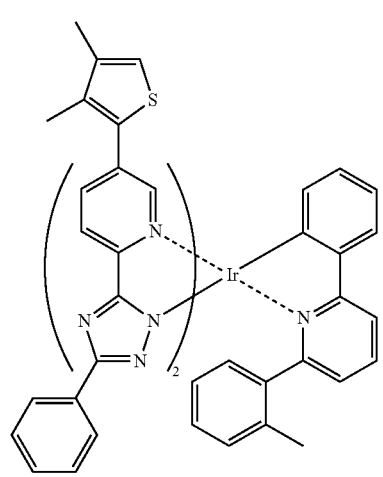

Exemplified Compound 5

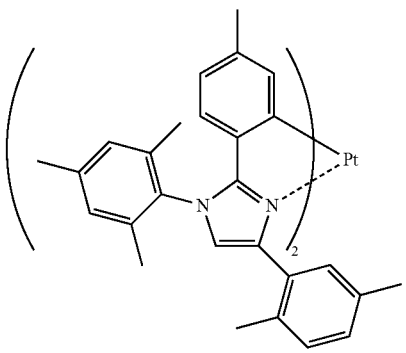

Exemplified Compound 6

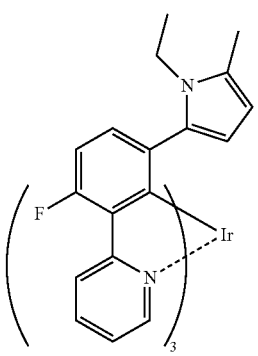

Exemplified Compound 7

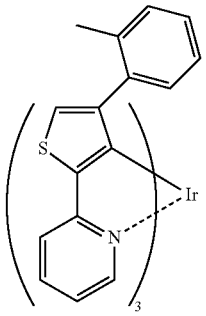

Exemplified Compound 8

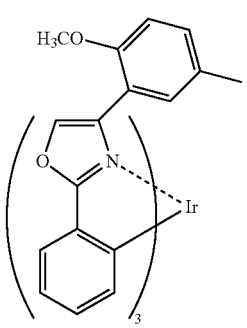

Exemplified Compound 9
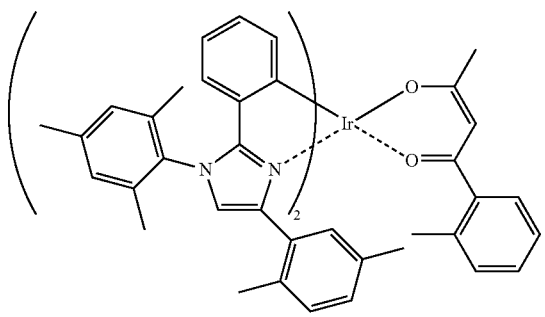
Exemplified Compound 10
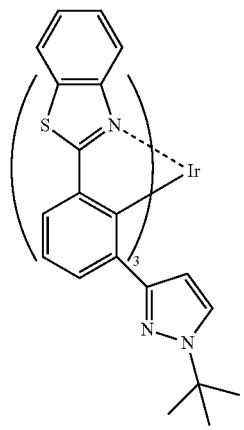
Exemplified Compound 11
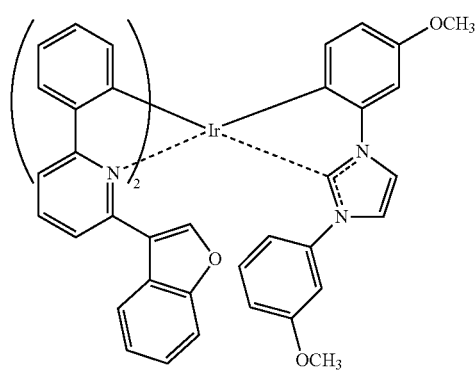
Exemplified Compound 12
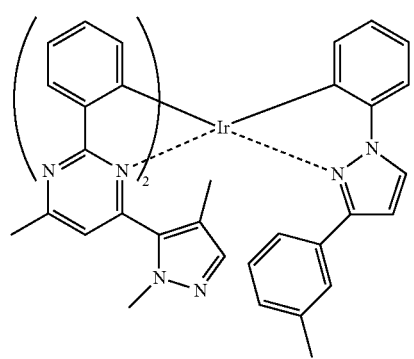
Exemplified Compound 13
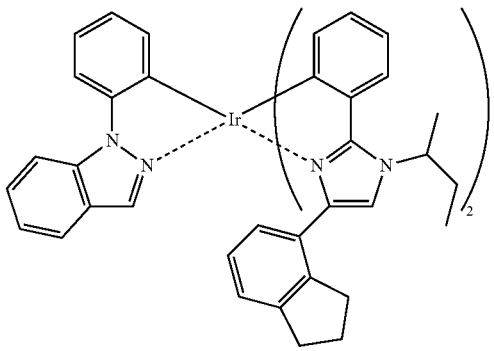
Exemplified Compound 14
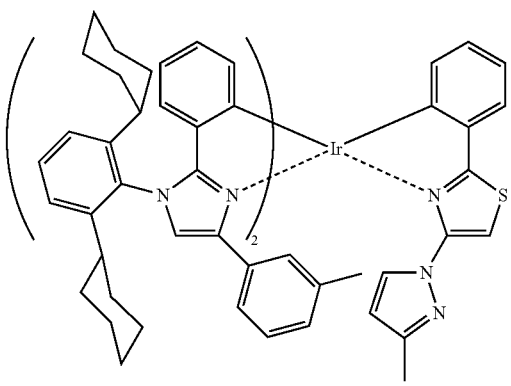
Exemplified Compound 15
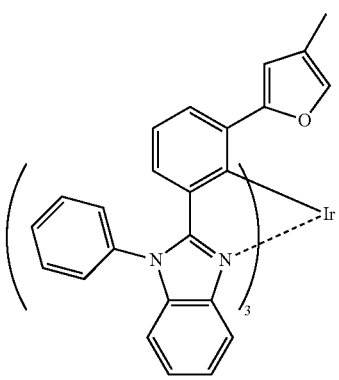
Exemplified Compound 16
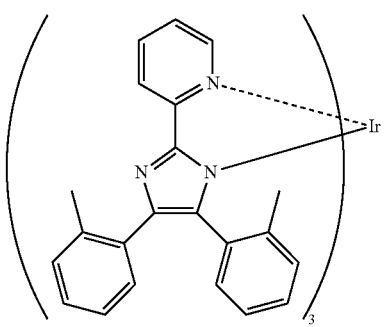

Exemplified Compound 17
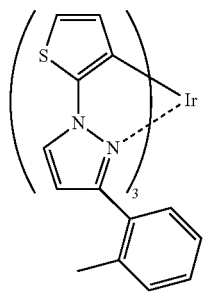
Exemplified Compound 18
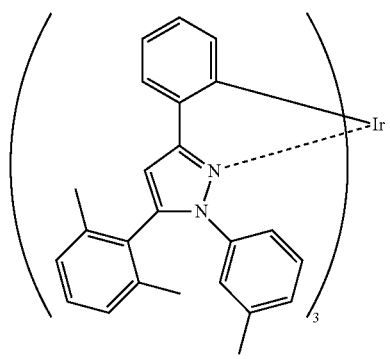
Exemplified Compound 19
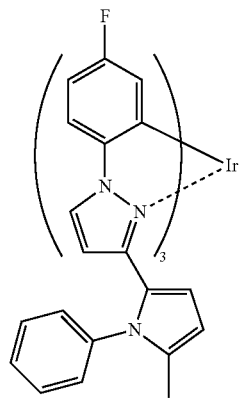
Exemplified Compound 20
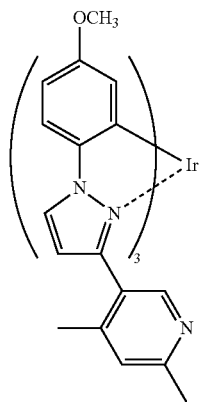
Exemplified Compound 21
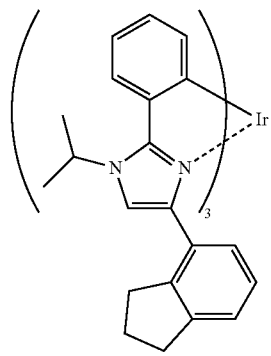
Exemplified Compound 22
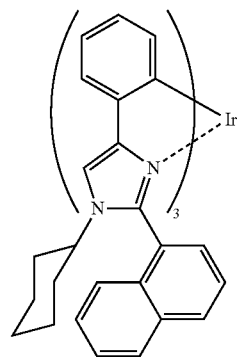
Exemplified Compound 23
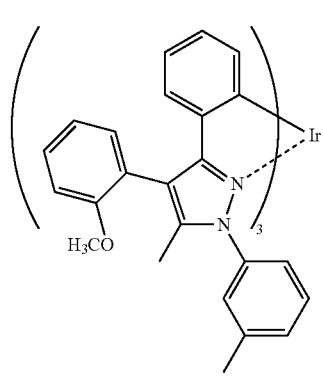
Exemplified Compound 24
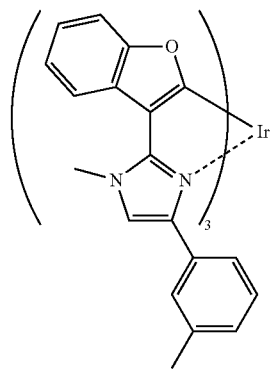

-continued
Exemplified Compound 25
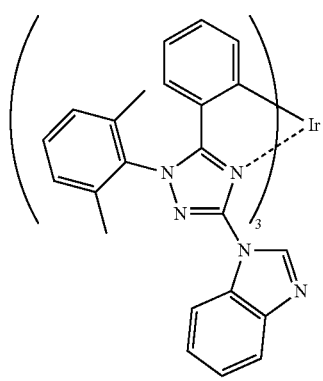
Exemplified Compound 26
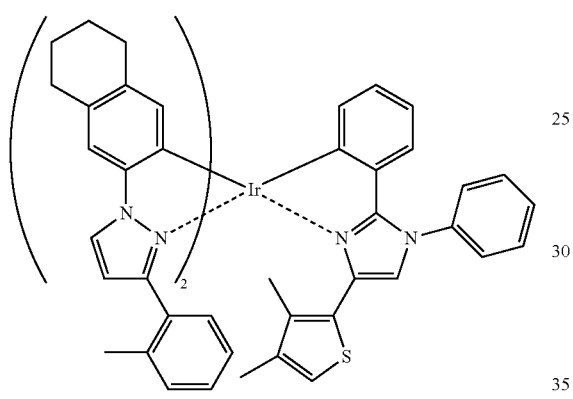
Exemplified Compound 27
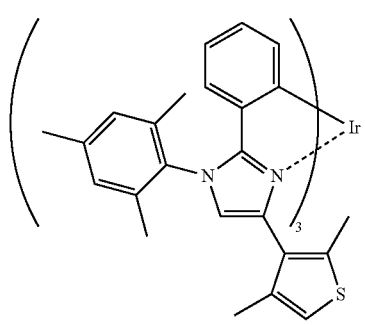
Exemplified Compound 28
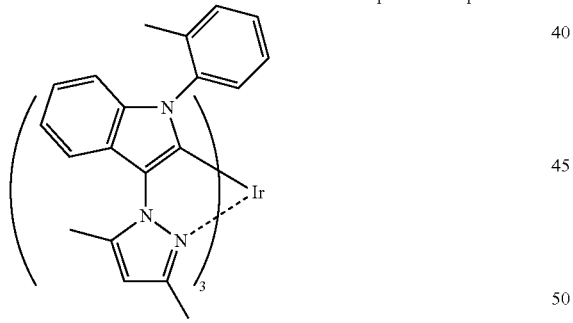
-continued
Exemplified Compound 29
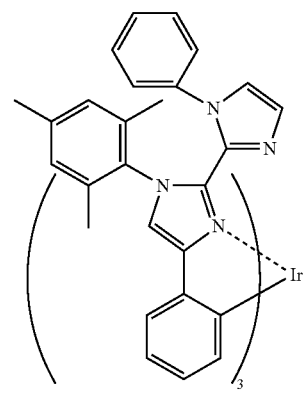
Exemplified Compound 30
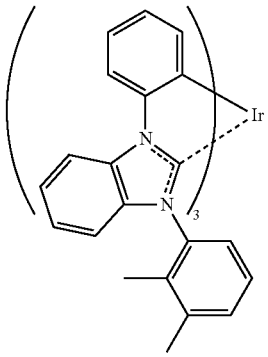
Exemplified Compound 31
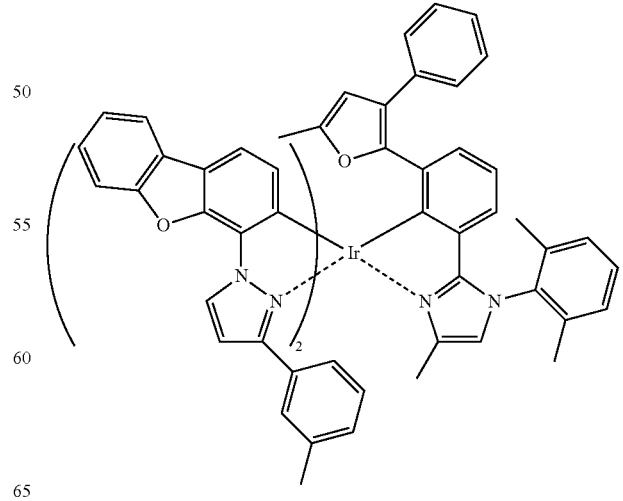

Exemplified Compound 32
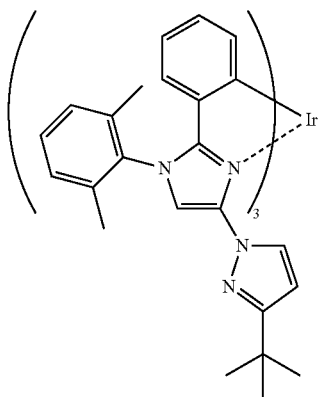
Exemplified Compound 33
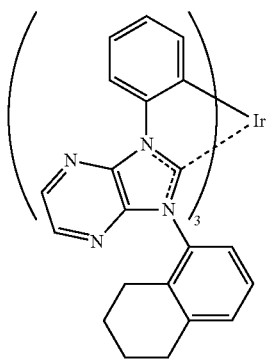
Exemplified Compound 34
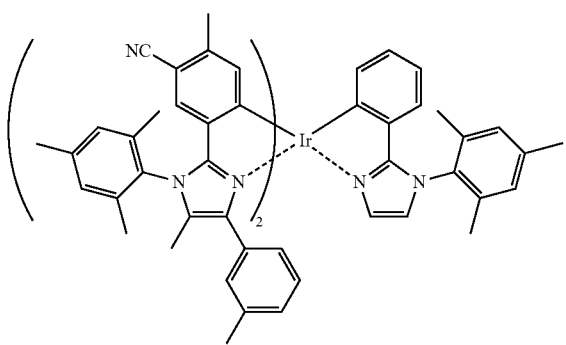
Exemplified Compound 35
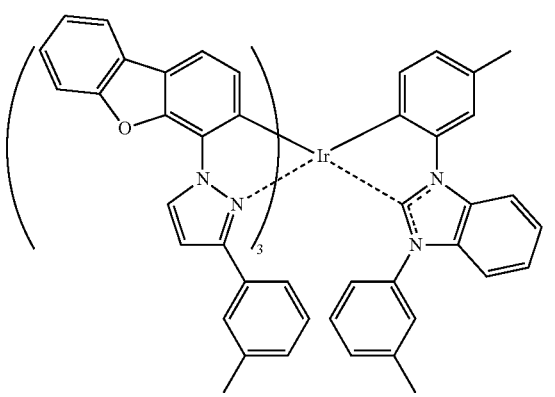
Exemplified Compound 36
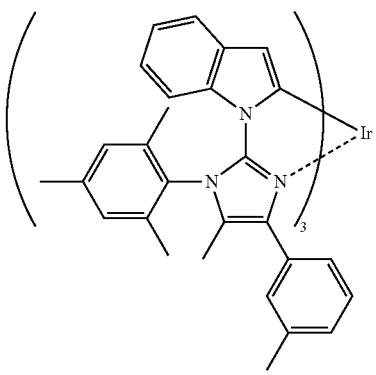
Exemplified Compound 37
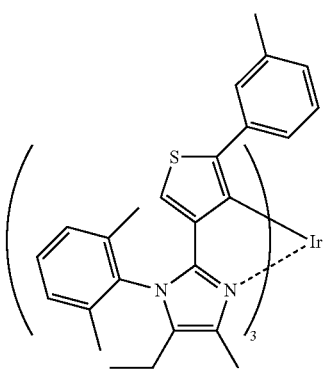
Exemplified Compound 38
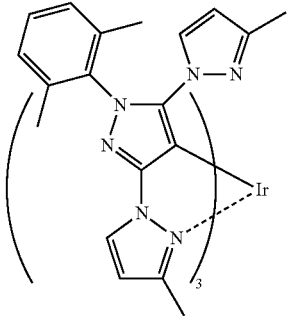
Exemplified Compound 39
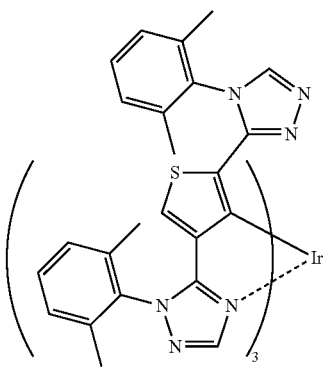

Exemplified Compound 40
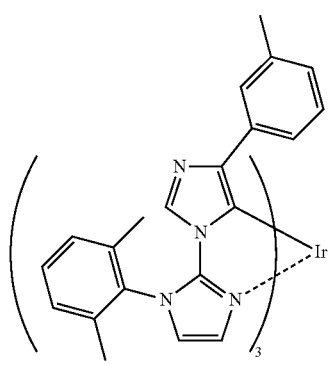
Exemplified Compound 41
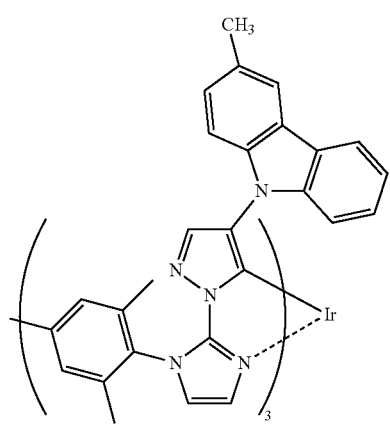
Exemplified Compound 42
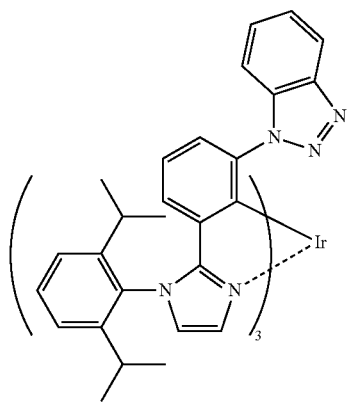
Exemplified Compound 43
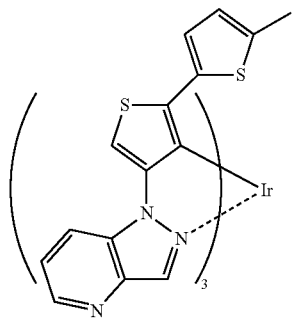
Exemplified Compound 44
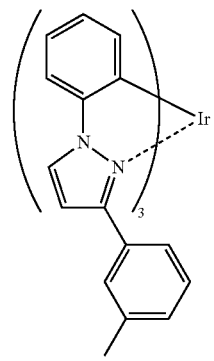
Exemplified Compound 45
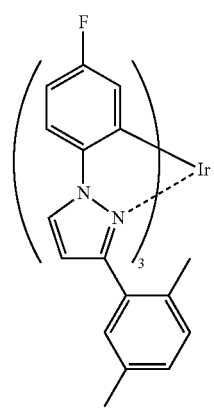
Exemplified Compound 46
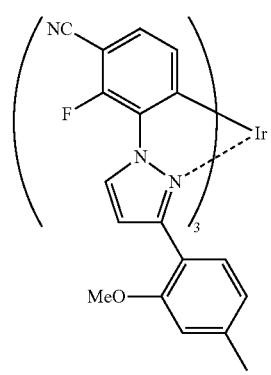
Exemplified Compound 47
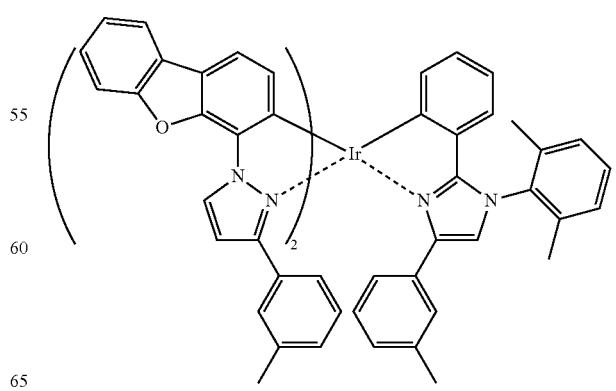

Exemplified Compound 48
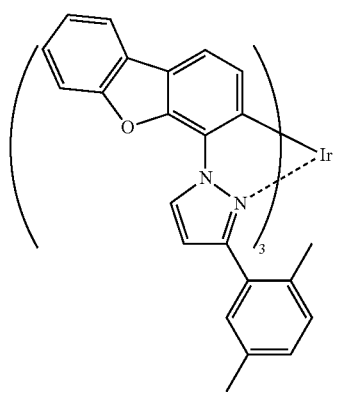
Exemplified Compound 49
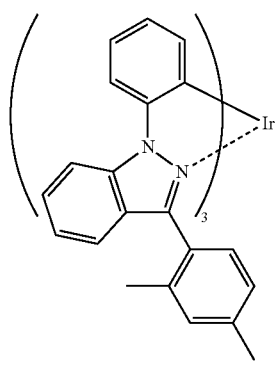
Exemplified Compound 50
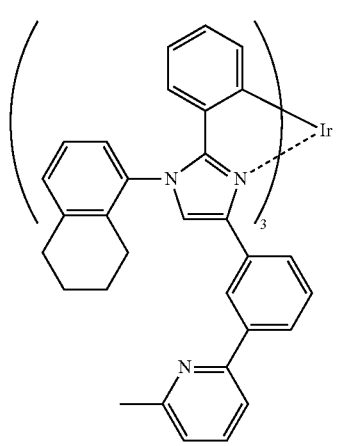
Exemplified Compound 51
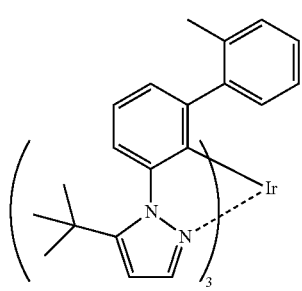
Exemplified Compound 52
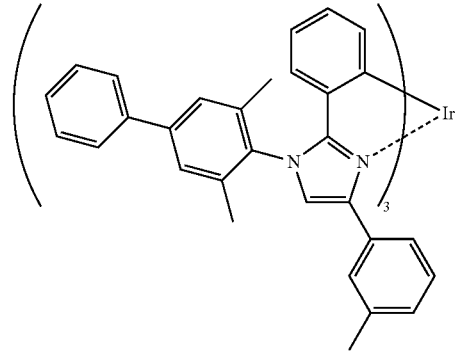
Exemplified Compound 53
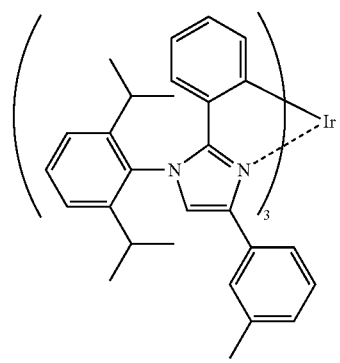
Exemplified Compound 54
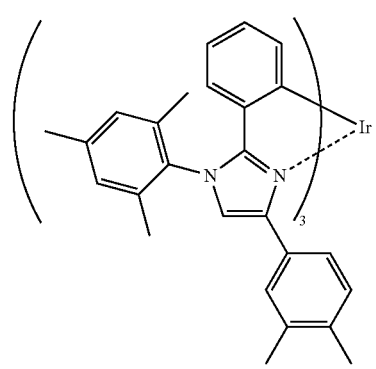
Exemplified Compound 55
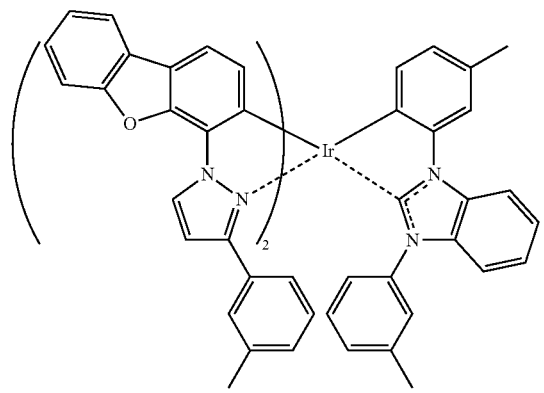

Exemplified Compound 56
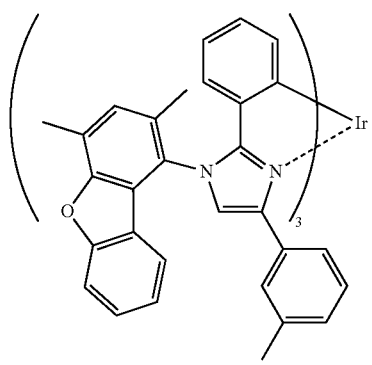
Exemplified Compound 57
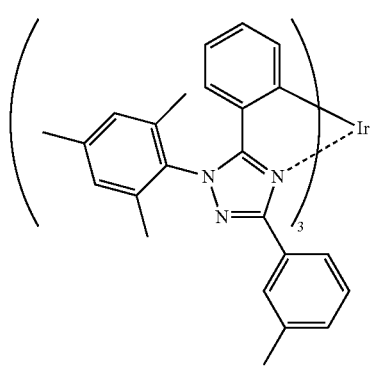
Exemplified Compound 58
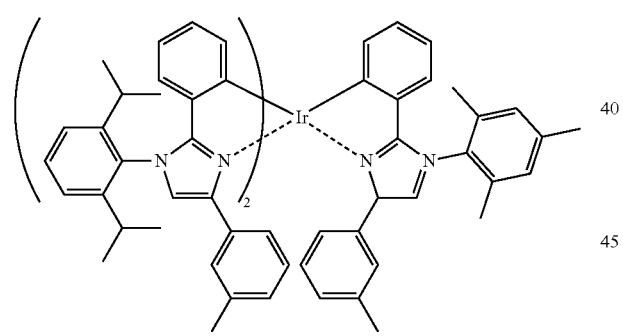
Exemplified Compound 59
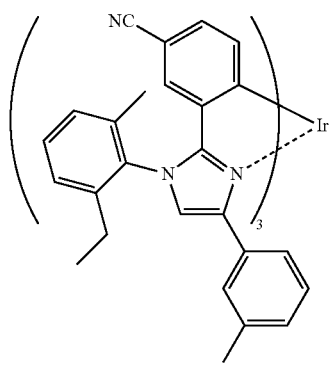
Exemplified Compound 60
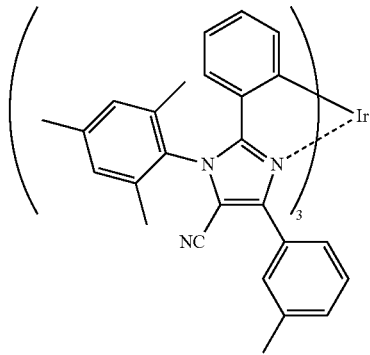
Exemplified Compound 61
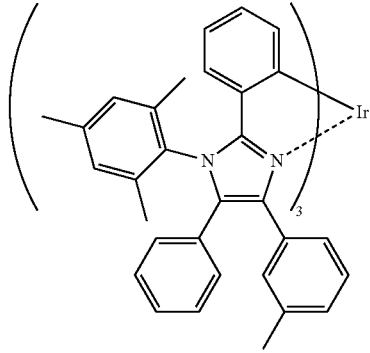
Exemplified Compound 62
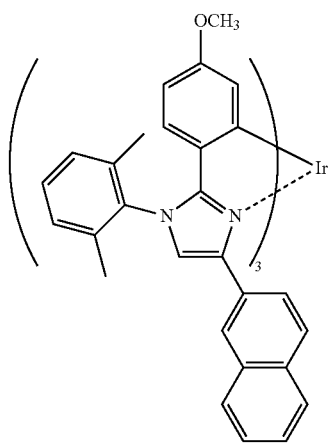
Exemplified Compound 63
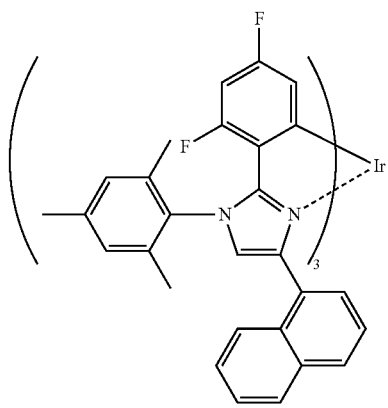

Exemplified Compound 64

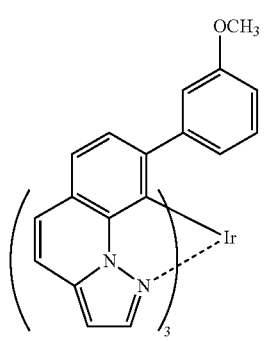

Exemplified Compound 65

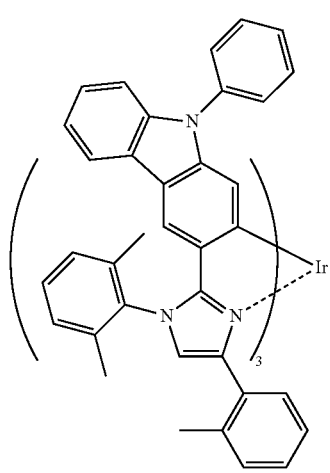

Exemplified Compound 66

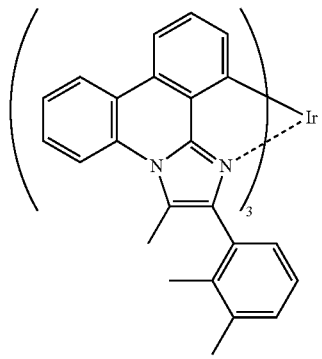

Exemplified Compound 67

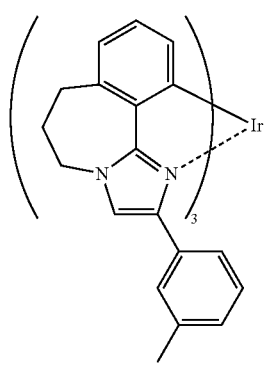

Exemplified Compound 68

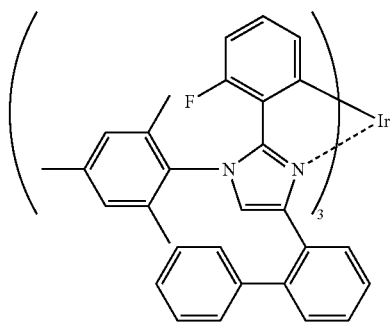

Exemplified Compound 69

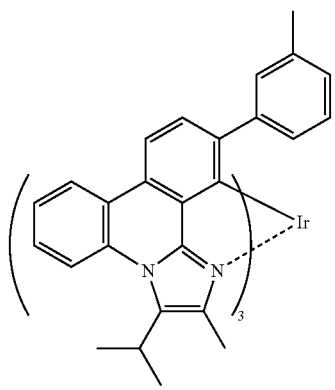

Exemplified Compound 70

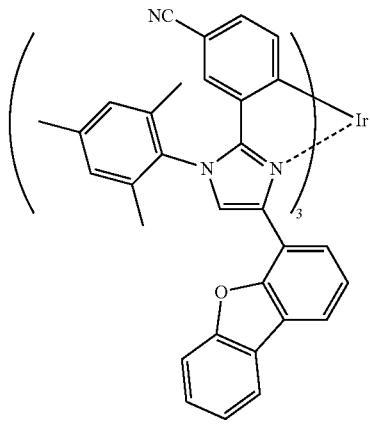

Exemplified Compound 71

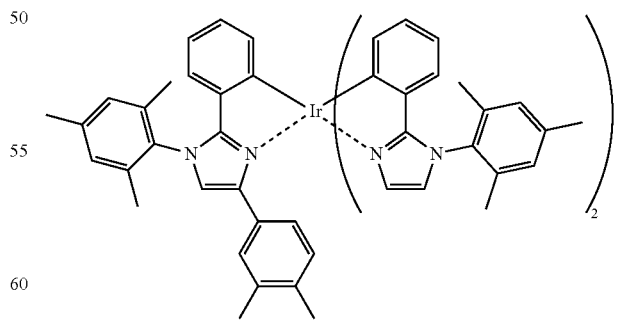

<<Configuration of Organic EL Element>>

The organic EL element according to the present invention preferably includes a pair of electrodes, and one or more organic layers disposed between the pair of electrodes. For example, the organic EL element may have a layer structure (i) or (ii). In the present invention, the organic layer refers to a layer containing an organic compound.

(i) anode/hole injecting layer/hole transporting layer/luminous layer/electron transporting layer/electron injecting layer/cathode (ii) anode/hole injecting layer/hole transporting layer/luminous layer/hole blocking layer/electron transporting layer/electron injecting layer/cathode <<Luminous Layer>>

The luminous layer according to the present invention emits light through recombination of electrons and holes injected into the luminous layer from the electrodes or from the electron transporting layer and hole transporting layer. The luminous layer may have a luminous portion therein or at the interface between the luminous layer and its adjacent layer. The luminous layer preferably comprises a mixed isomeric metal complex composition as a phosphorescent organic EL material. The luminous layer preferably contains a host compound.

The luminous layer can have any total thickness. The total thickness is controlled in the range of preferably 2 nm to 5 µm, more preferably 2 to 200 nm, particularly preferably 10 to 100 nm to attain a homogenous film, avoid application of significantly high voltage for light emission, and enhance the stability of the color of light to a driving current.

(Use of Known Dopants in Combination)

The luminous dopant according to the present invention may contain several compounds, for example, a combination of phosphorescent dopants having different structures, or a combination of a phosphorescent dopant and a fluorescent dopant, in the range not impairing the advantageous effects of the present invention.

Non-limiting, specific examples of known luminous dopants (also referred to as dopant compounds) usable in combination with the iridium complex compound according to the present invention represented by Formula (1) are shown below:

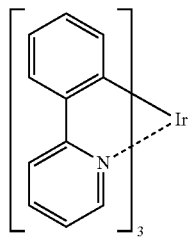
D-1

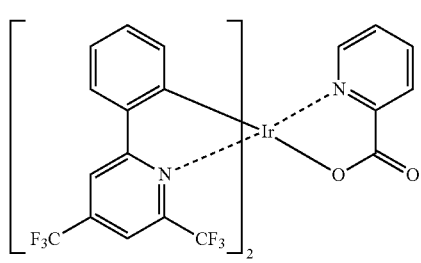
D-2

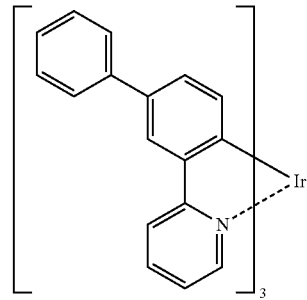
D-3

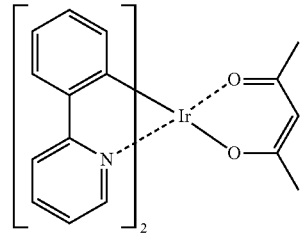
D-4

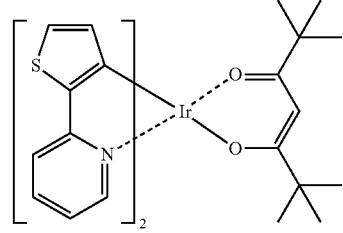
D-5

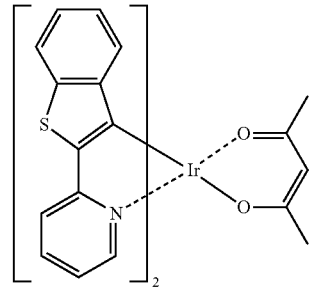
D-6

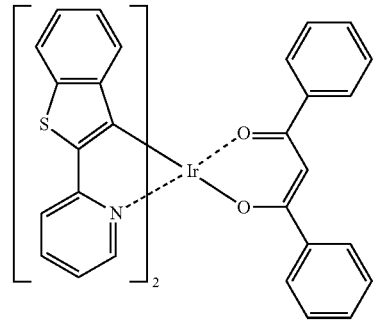
D-7

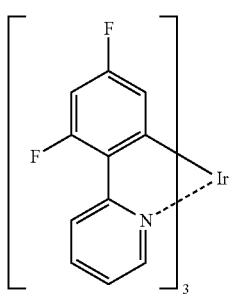 D-8
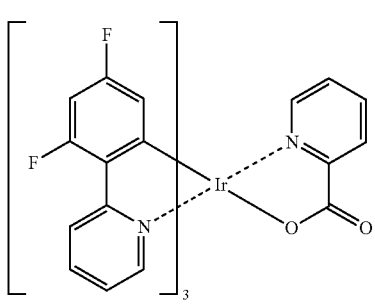 D-9
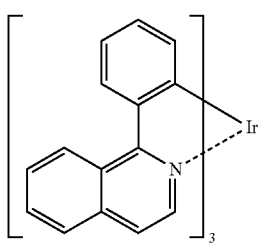 D-10
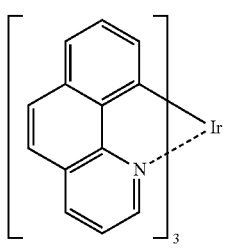 D-11
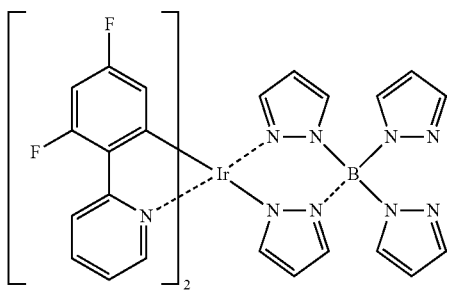 D-12
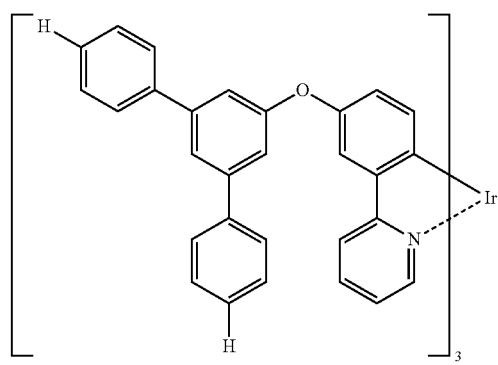 D-13
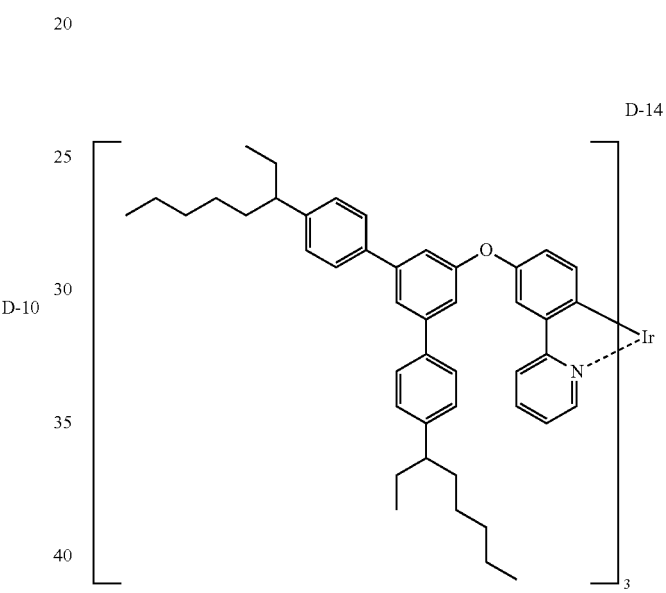 D-14
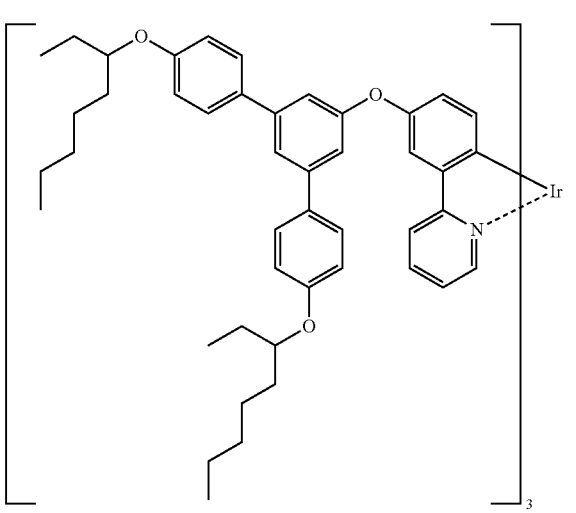 D-15

D-16
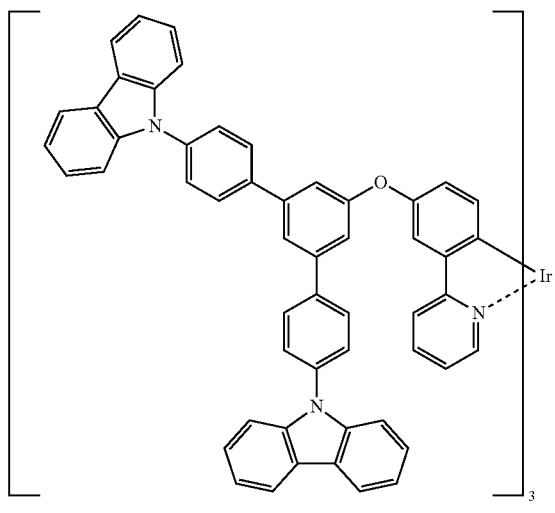
D-17
D-18
D-19
D-20
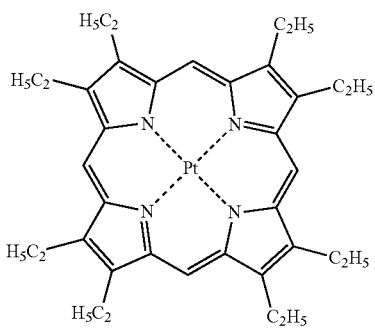
D-21
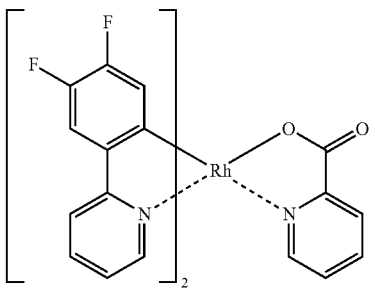
D-22
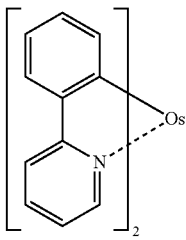
D-23
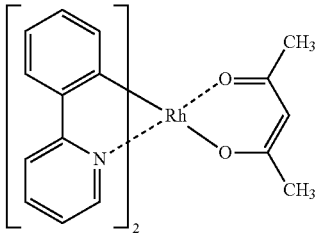
D-24
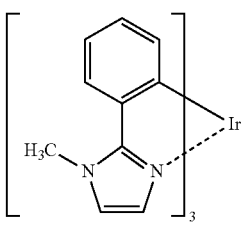
D-25
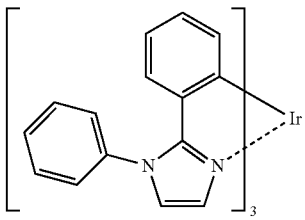

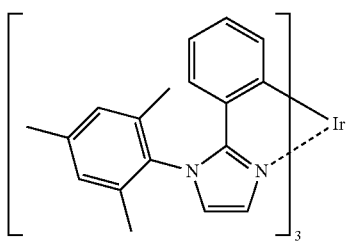
D-26
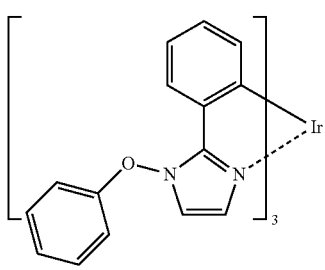
D-27
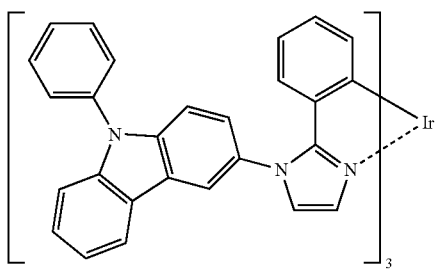
D-28
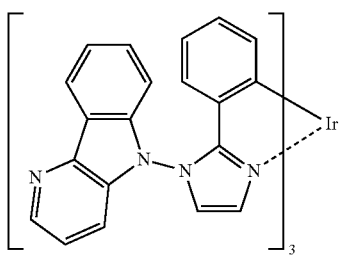
D-29
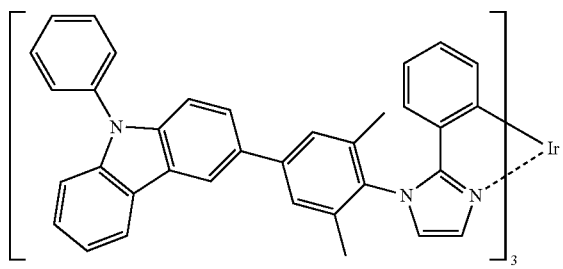
D-30
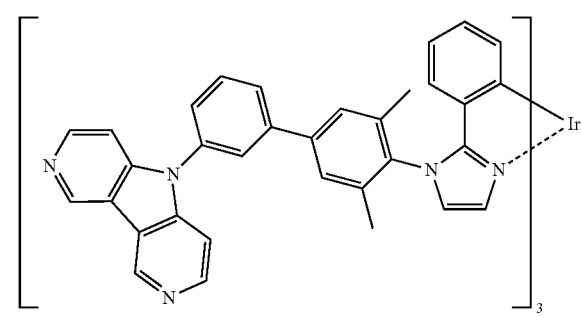
D-31
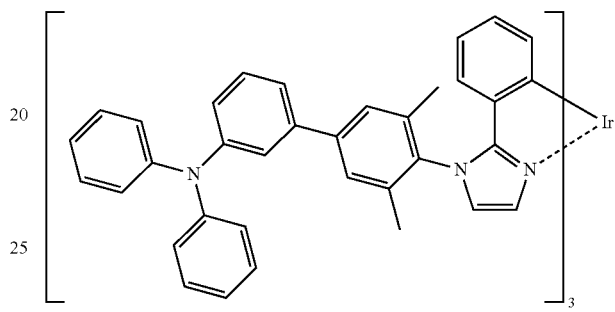
D-32
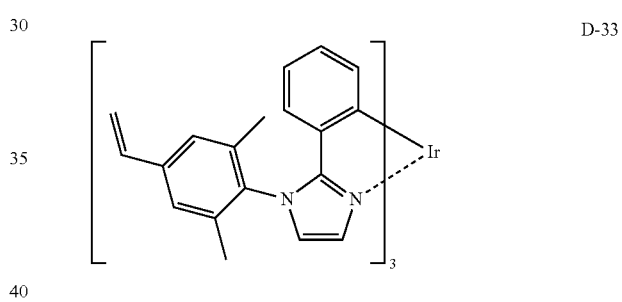
D-33
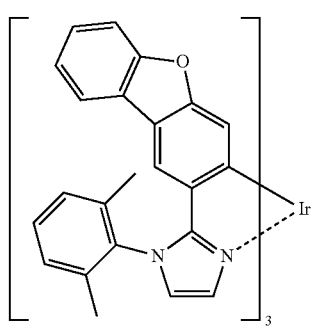
D-34
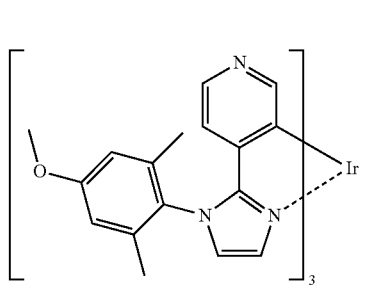
D-35

-continued
D-36
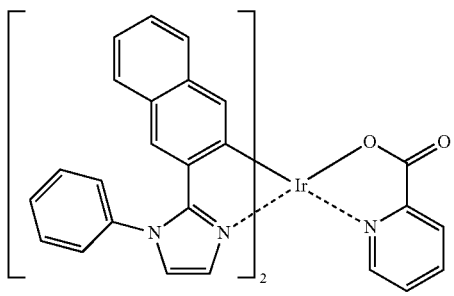
D-37
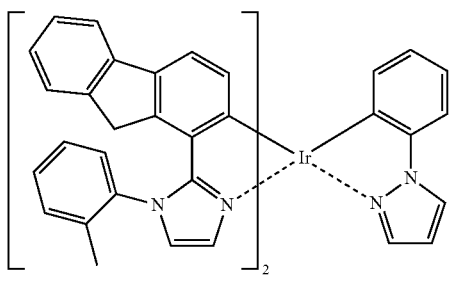
D-38
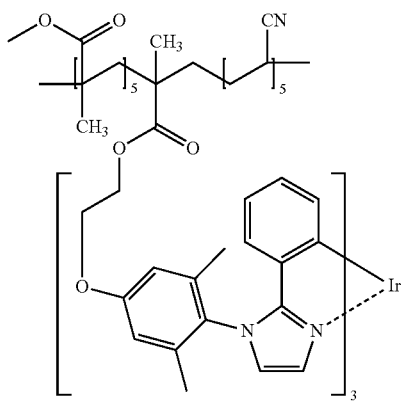
D-39
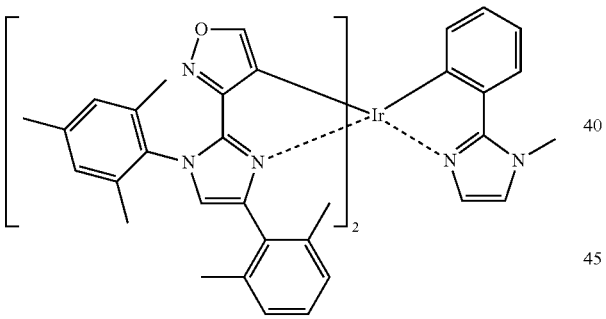
-continued
D-40
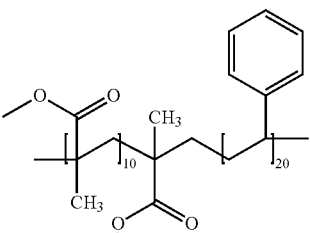
D-41
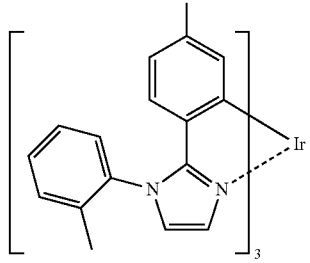
D-42
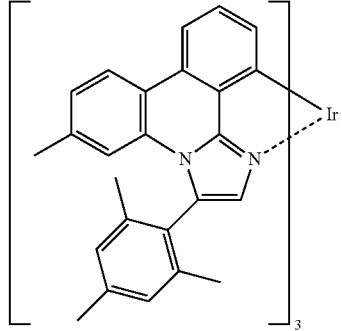

-continued

D-43
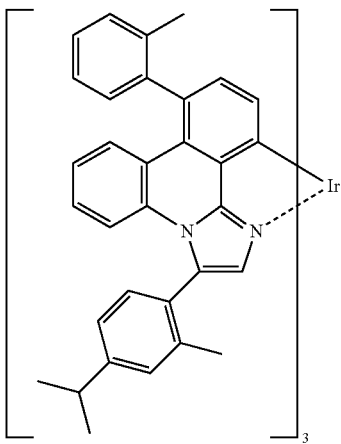

D-44
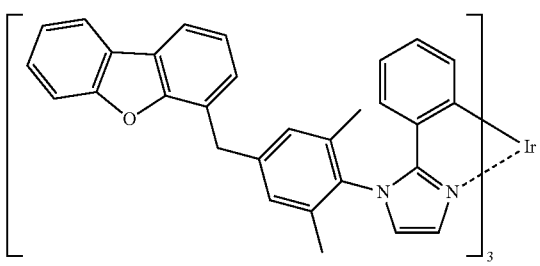

D-45
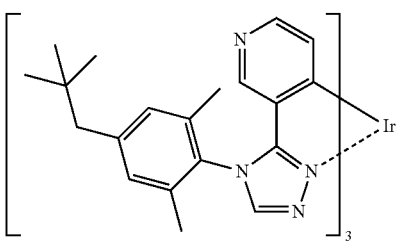

D-46
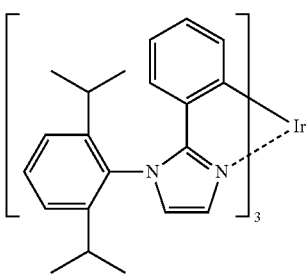

D-47
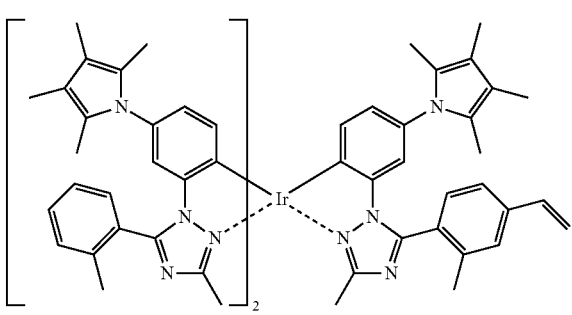

(2) Host Compound

The host compound in the present invention (also referred to as luminous host) is defined as a compound contained in the luminous layer in an amount of 20 mass % or more and having a phosphorescent quantum yield of less than 0.1 at room temperature (25° C.) during phosphorescence. The phosphorescent quantum yield is preferably less than 0.01. The compound is preferably contained in the luminous layer in an amount of 20 mass % or more.

Any host compound usually used in organic EL elements can also be used in the present invention. Typical examples of such a host compound include compounds having basic skeletons of carbazole derivatives, triarylamine derivatives, aromatic derivatives, nitrogen-containing heterocyclic compounds, thiophene derivatives, furan derivatives, and oligoarylene compounds; or carboline derivatives and diazacarbazole derivatives (the diazacarbazole derivatives refer to carboline derivatives in which at least one carbon atom of the hydrocarbon ring in a carboline ring is replaced with a nitrogen atom).

Among these known host compounds usable in the present invention, preferred are compounds having hole and electron transportability, having high glass transition temperatures (Tg), and emitting light without conversion of the light into longer wavelengths.

These known host compounds can also be used alone or in combination in the present invention. Combined use of two or more host compounds can control the charge transfer to attain organic EL elements having high efficiency. Mixtures of the metal complexes used as phosphorescent dopants in the present invention and/or these known compounds can attain light emission of any color composed of different colors.

The host compound used in the present invention may be a low molecular compound, a high molecular compound having a repeating unit, or a low molecular compound having a polymerizable group such as a vinyl or epoxy group (polymerizable host compound). These compounds can be used alone or in combination.

Specific examples of the known host compounds include compounds described in Japanese Patent Application Laid-Open Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

The complex according to the present invention can appropriately interact with the host compound to prevent agglomeration of the complex molecules. The host compound used in this case should preferably interact with the complex and have a structure to prevent agglomeration of host compound molecules. Specifically, the host compound preferably has a partial structure interactive with the aryl group and the it-plane of the complex molecule and a partial structure to prevent interaction with other host compound molecules.

Although a general chemical structure of the host compound cannot be specified, a preferred structure of the host compound has the following features:

a. The host compound has a freely rotating biaryl structure.

b. The host compound having a freely rotating biaryl structure has a dibenzofuran structure.

c. The host compound having a freely rotating biaryl structure has a carbazole structure.
d. The host compound having a freely rotating biaryl structure has an unsubstituted phenyl group.

Non-limiting, specific examples of the preferred host compounds usable in combination with the complex according to the present invention are shown below:

OC-1

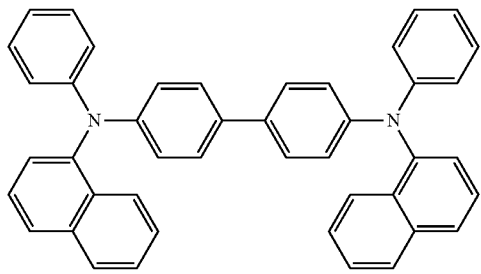

OC-2

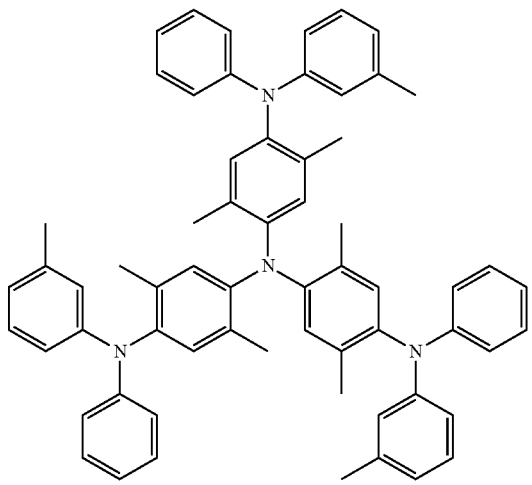

OC-3

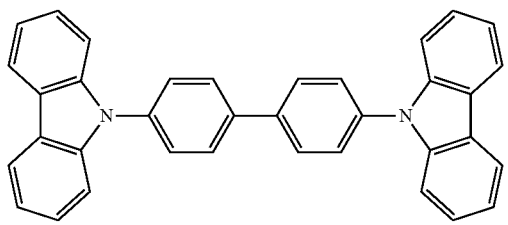

OC-4

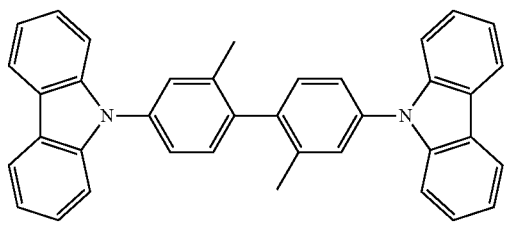

OC-5

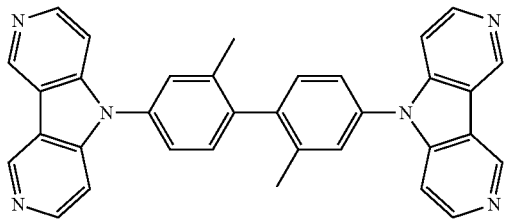

OC-6

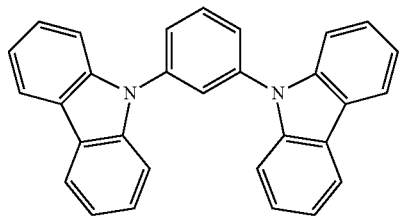

OC-7

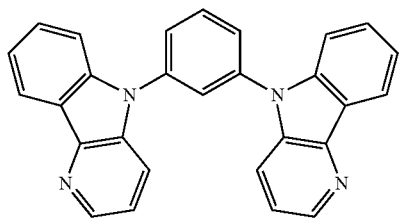

OC-8

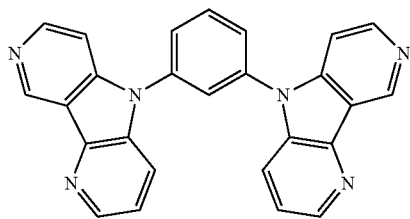

-continued
OC-9
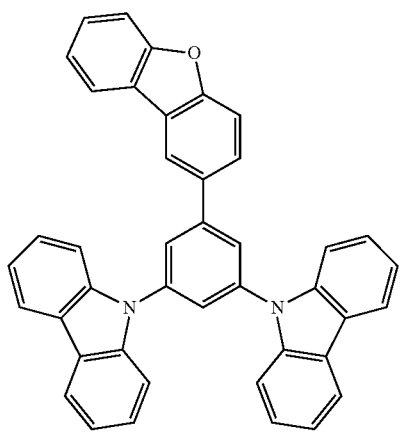
OC-10
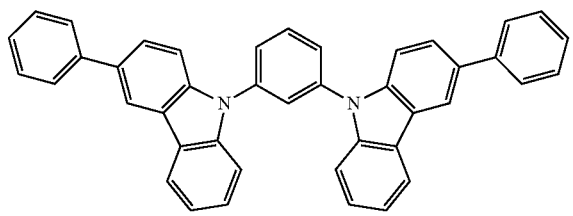
OC-11
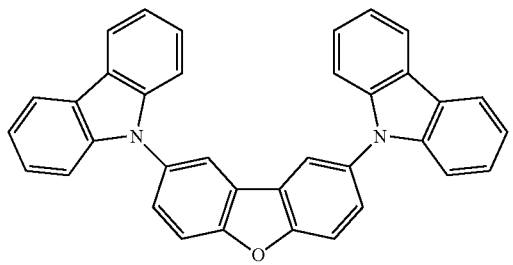
OC-12
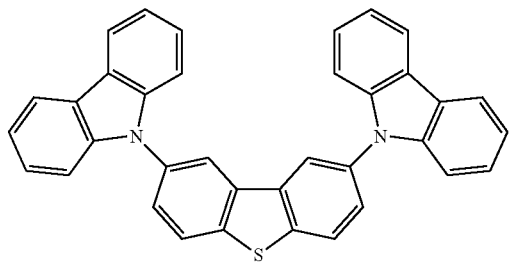
OC-13
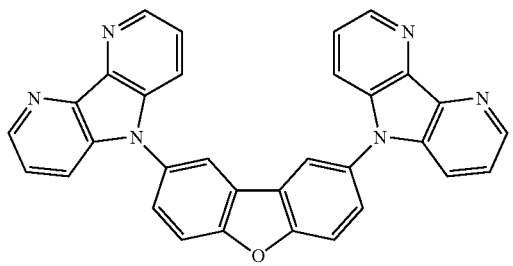
OC-14
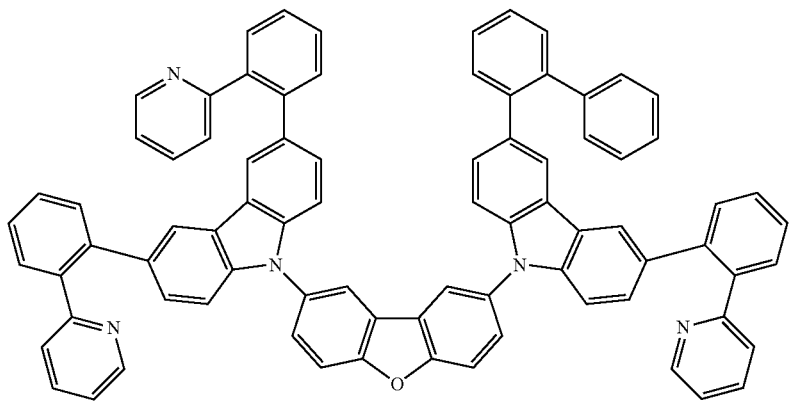

-continued
OC-15
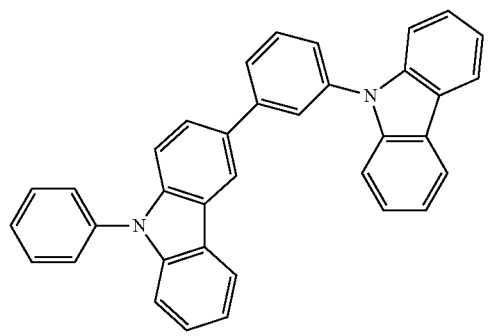
OC-16
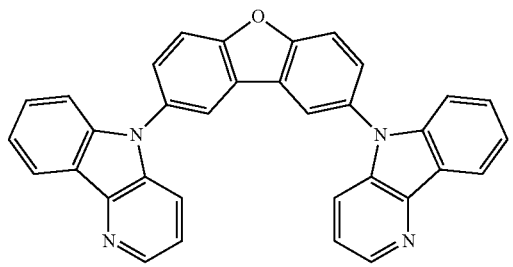
OC-17
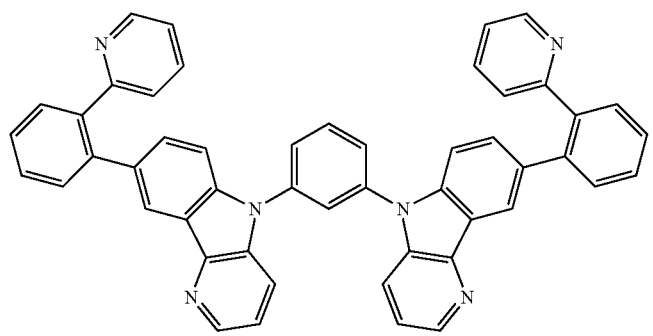
OC-18
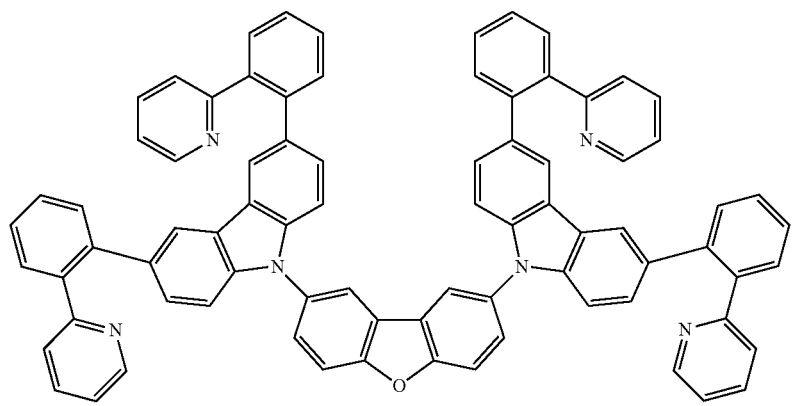
OC-19
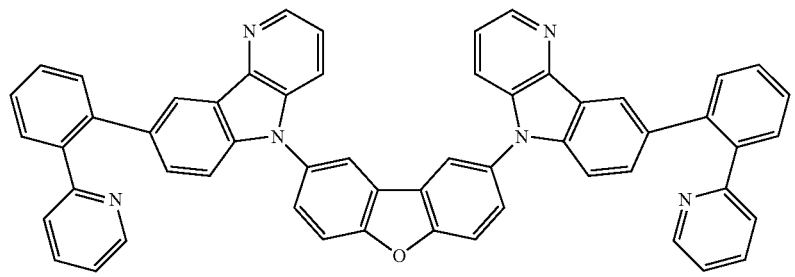

-continued
OC-20
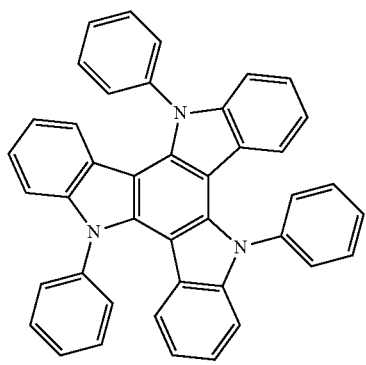
OC-21
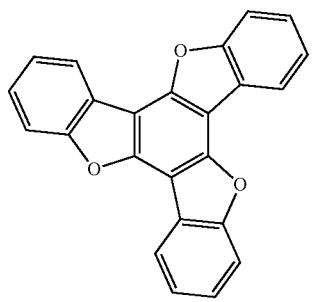
OC-22
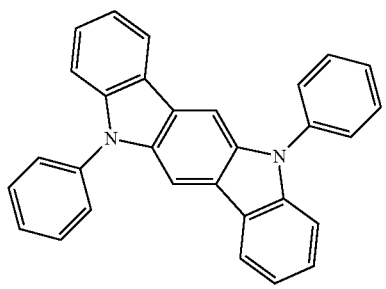
OC-23
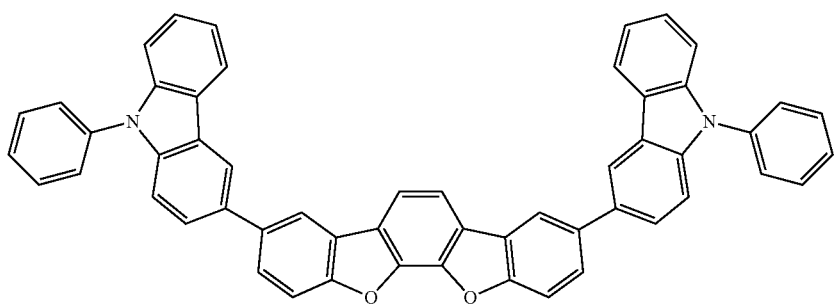
OC-24
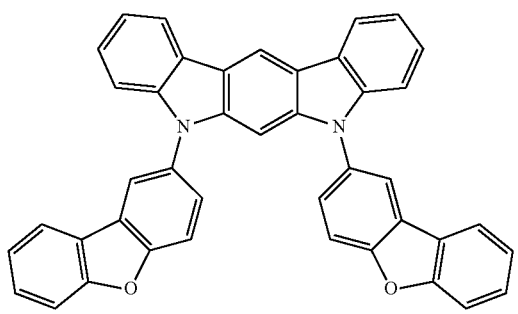
OC-25
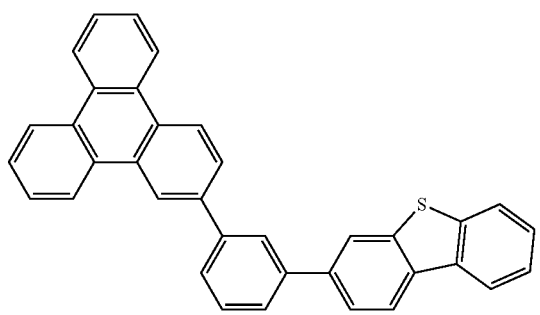
OC-26
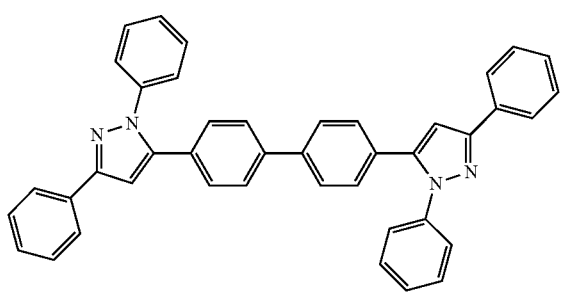
OC-27
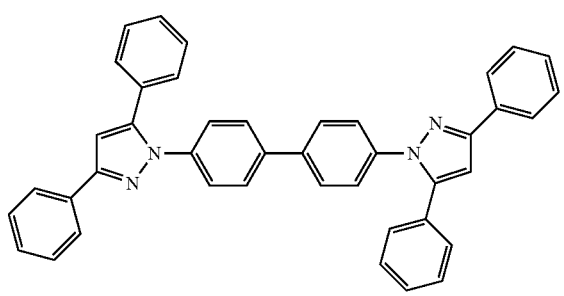

-continued
OC-28
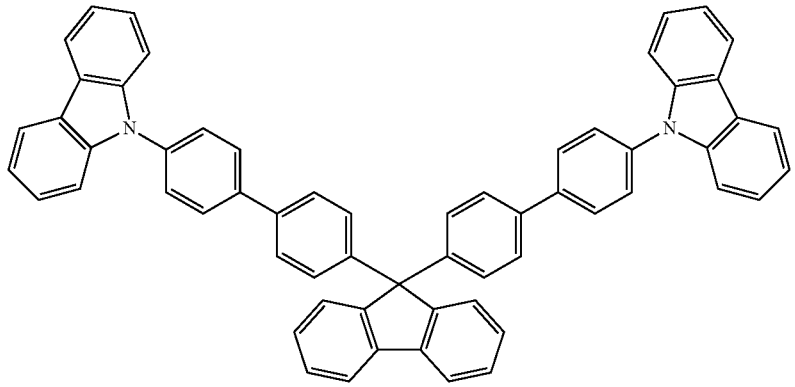
OC-29 OC-30
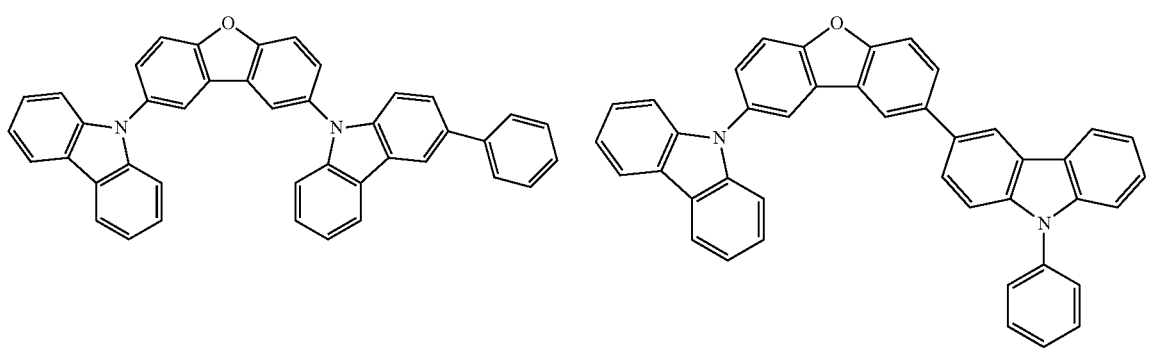
OC-31 OC-32
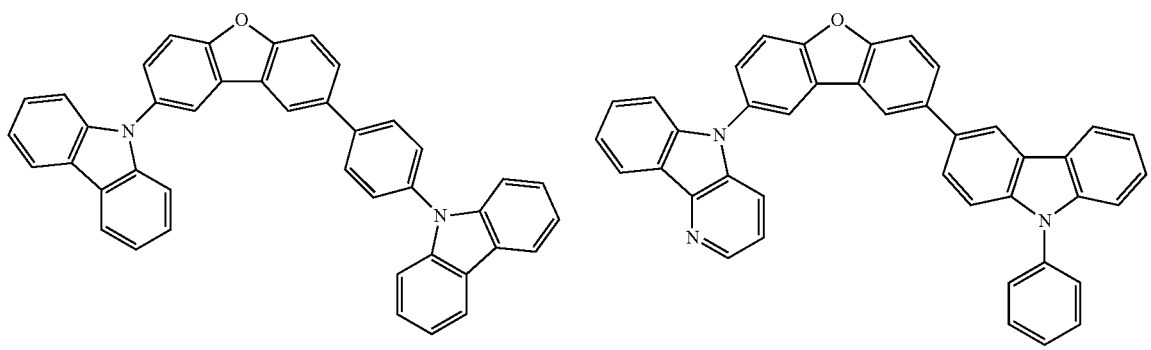
OC-33 OC-34
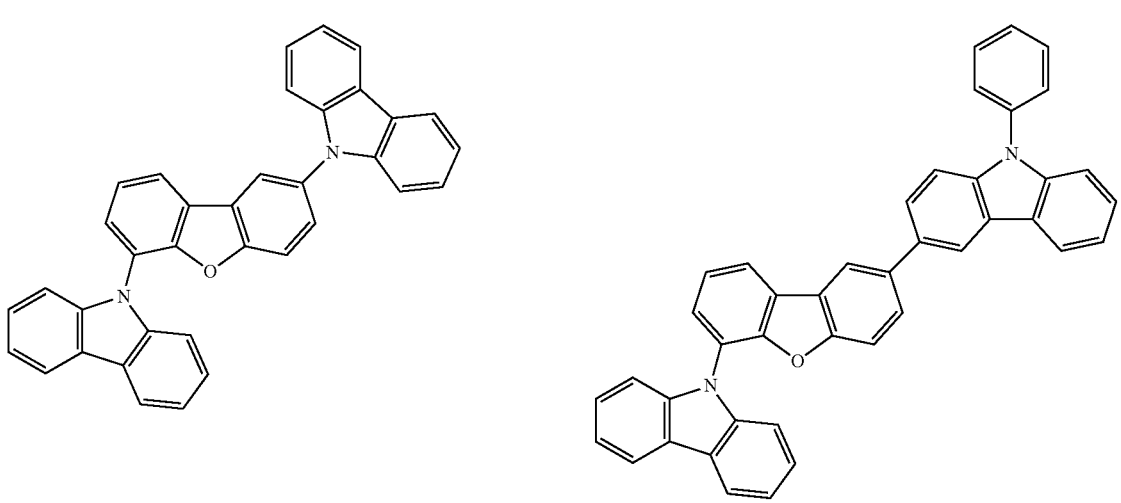

-continued
OC-35
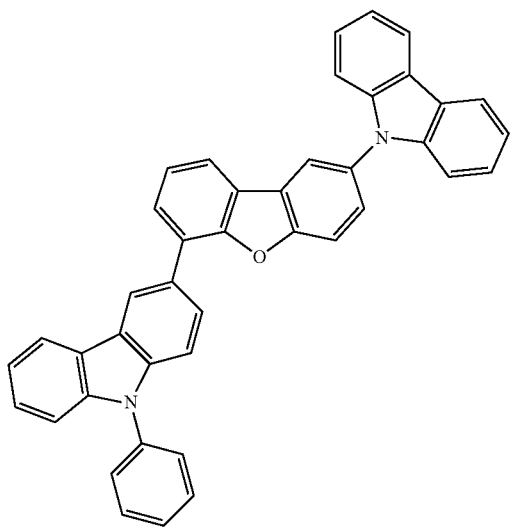
OC-36
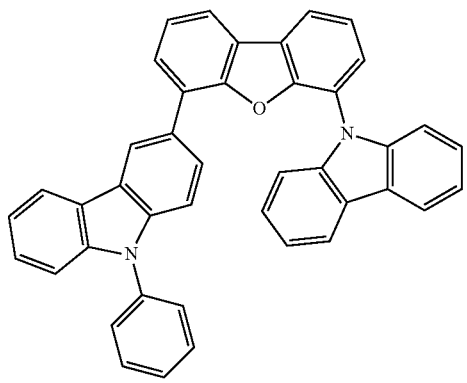
OC-37
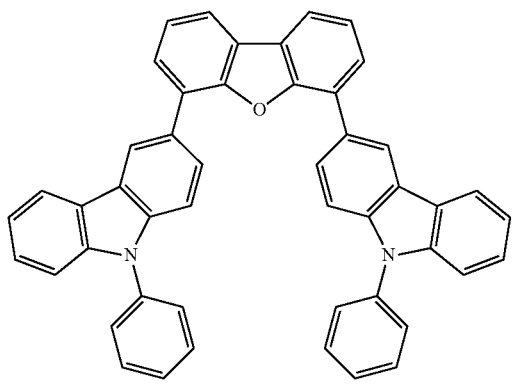
OC-38
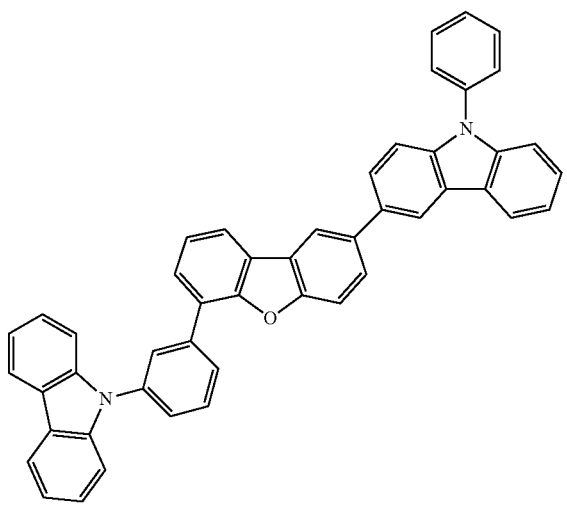
OC-39
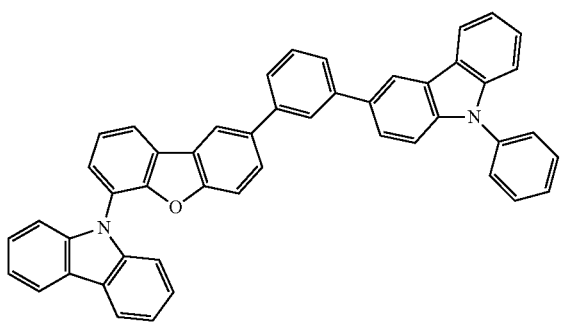
OC-40
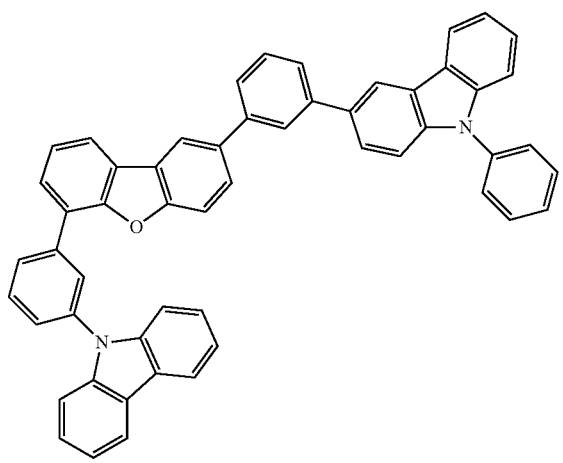

-continued
OC-41
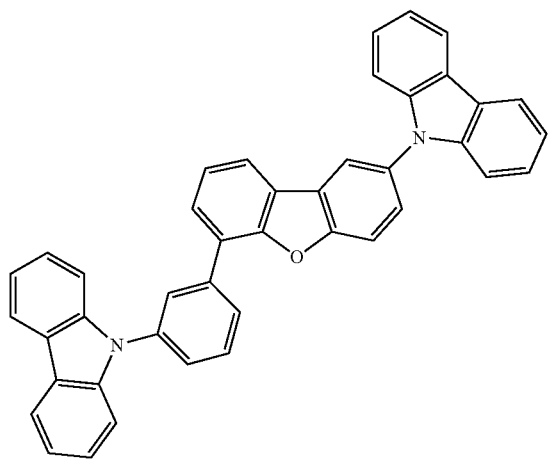
OC-42
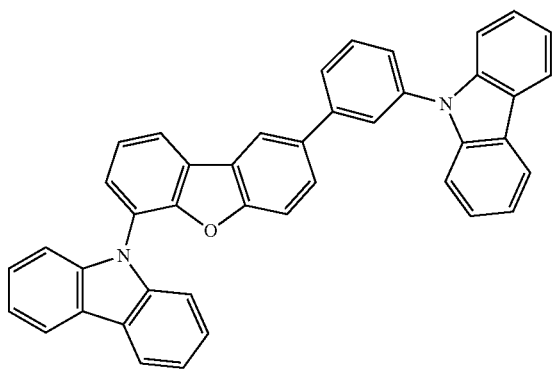
OC-43
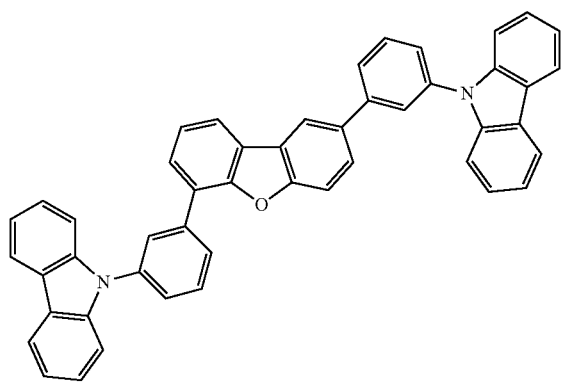
OC-44
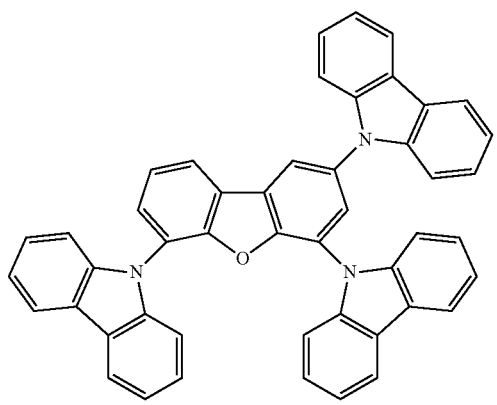
OC-45
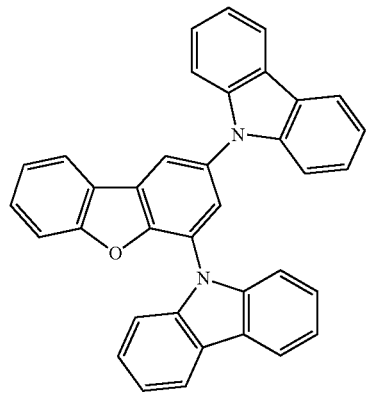
OC-46
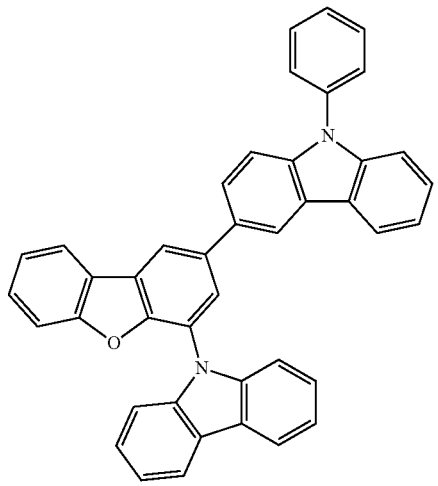

-continued
OC-47
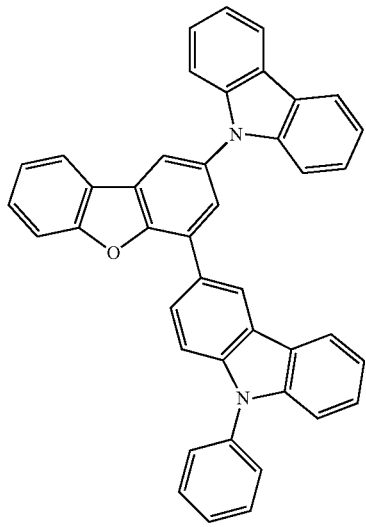
OC-48
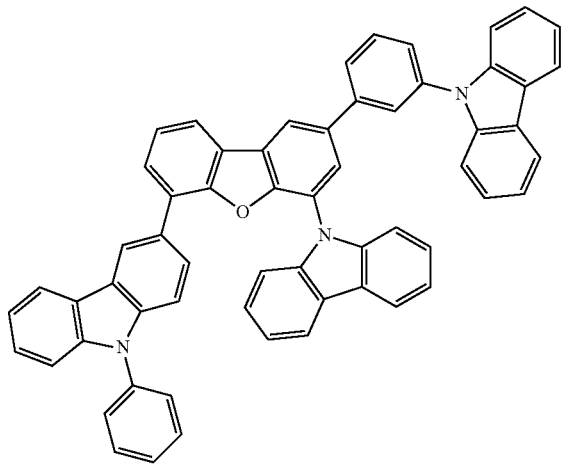
OC-49
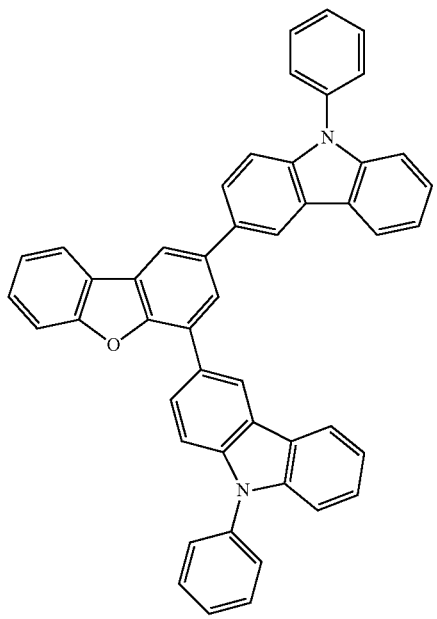
OC-50
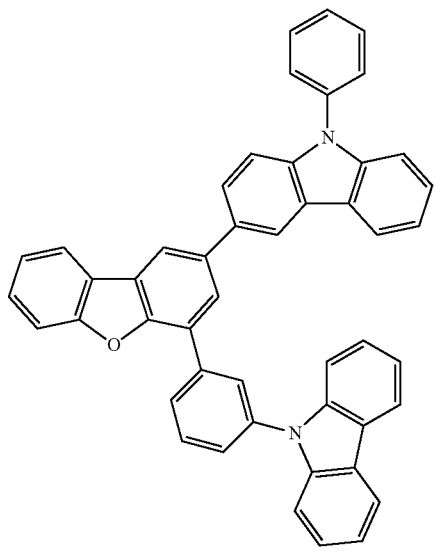
OC-51
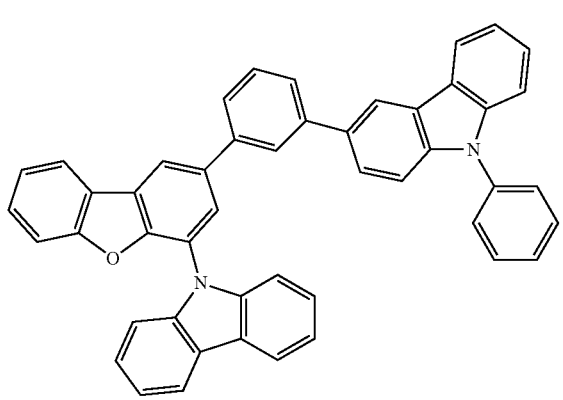
OC-52
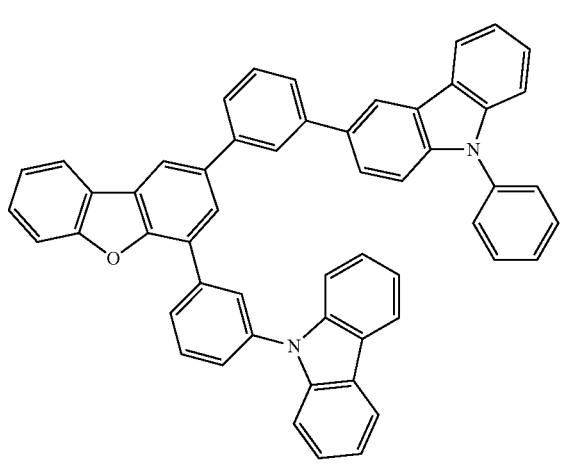

-continued
OC-53
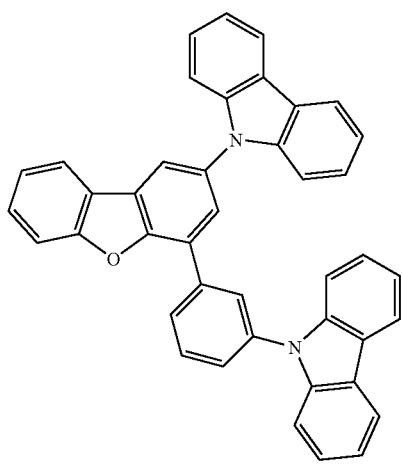
OC-54
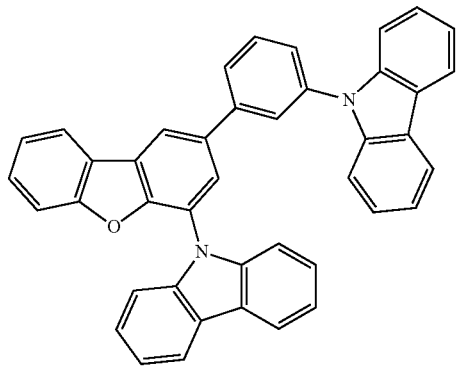
OC-55
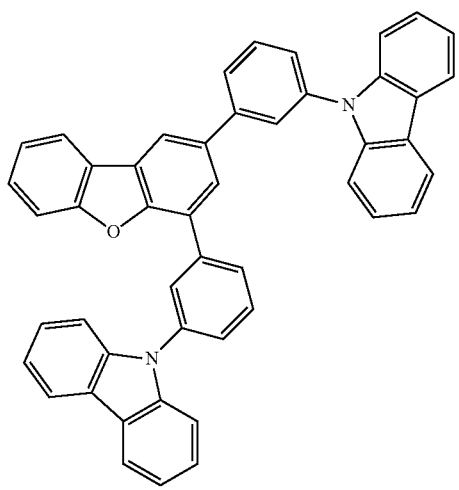
OC-56
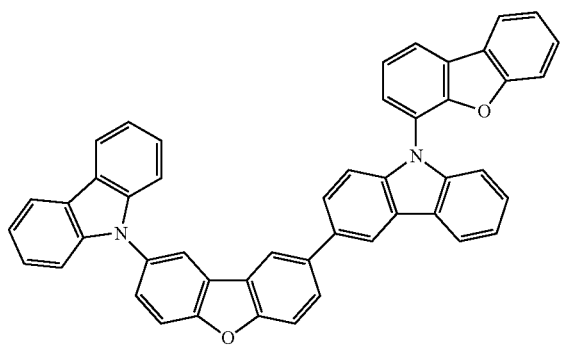
OC-57
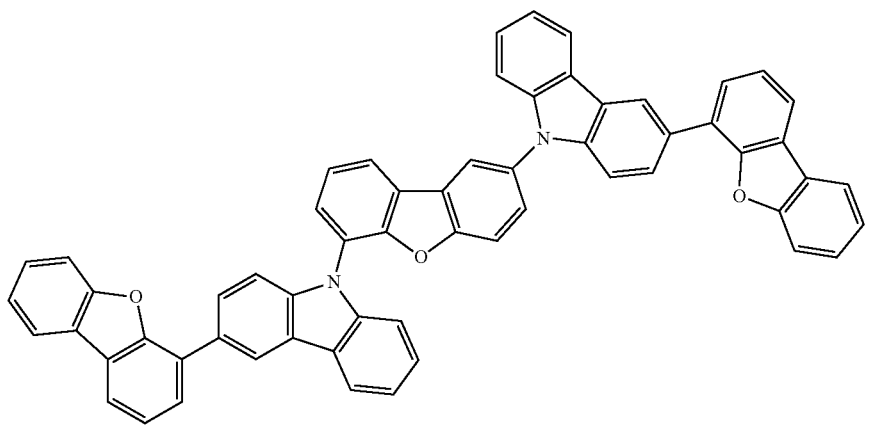

-continued
OC-58
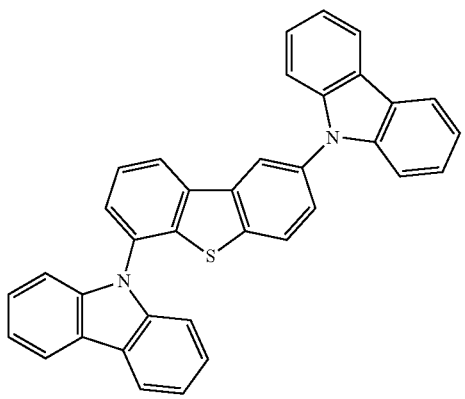
OC-59
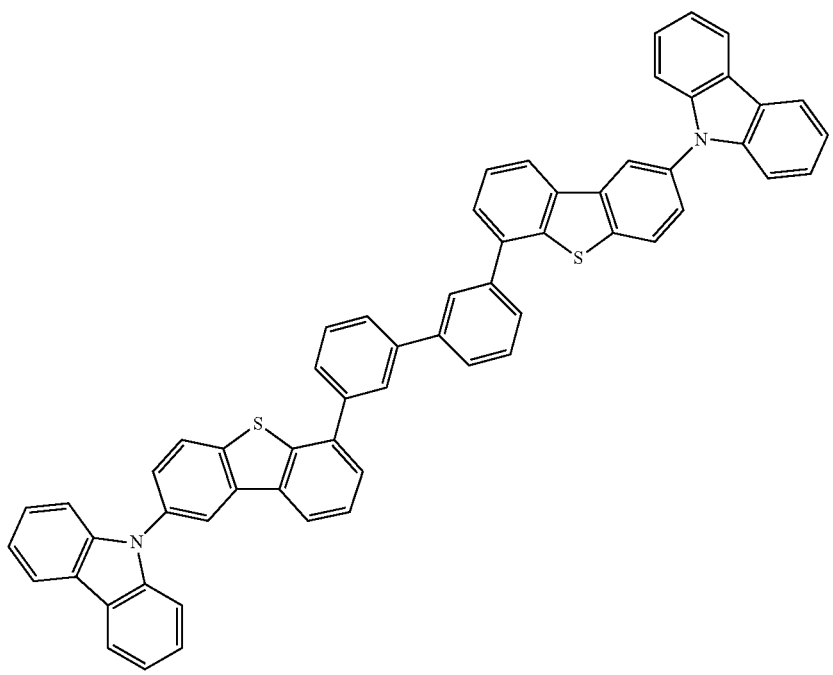
OC-60
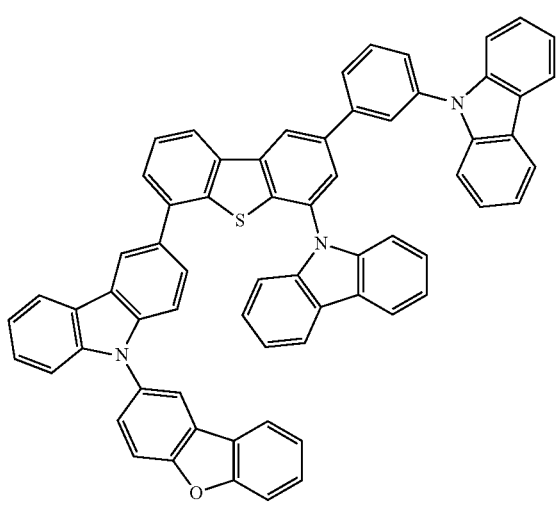
OC-61
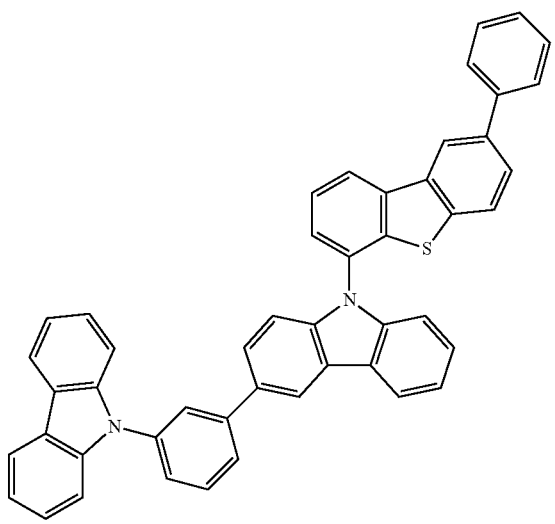

OC-62
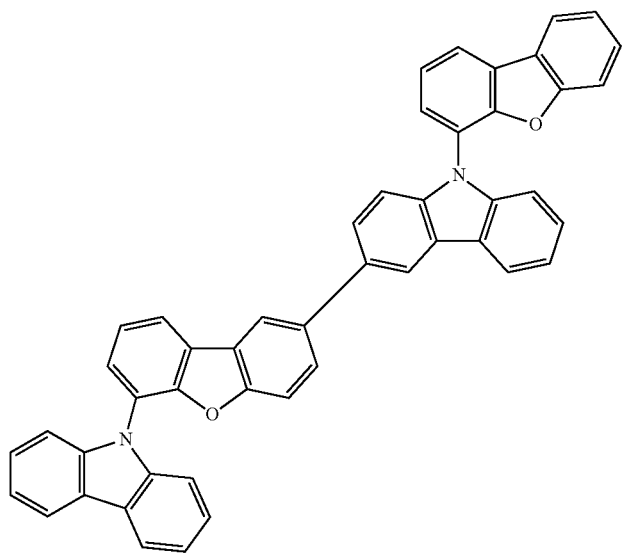
OC-63 OC-64
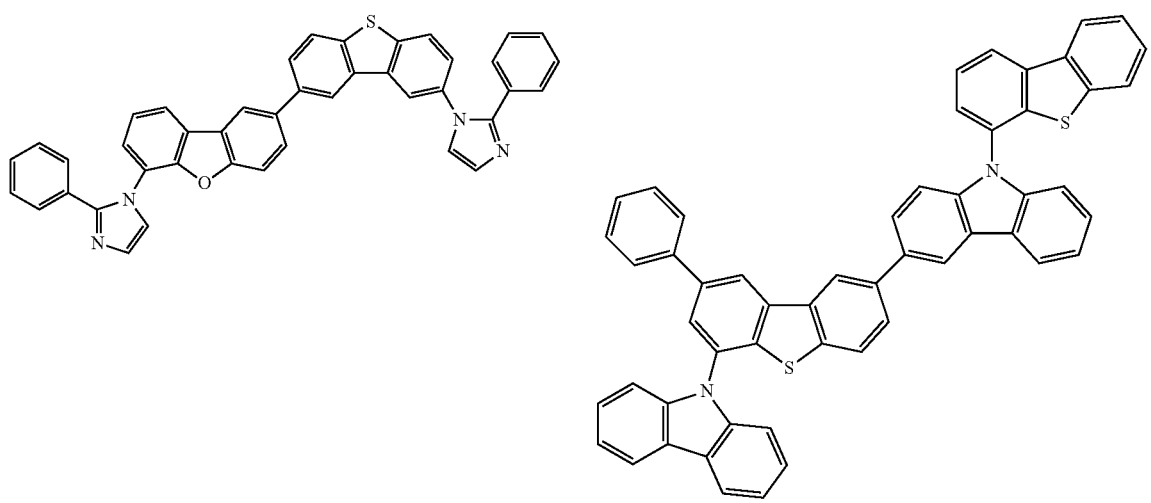
OC-65 OC-66
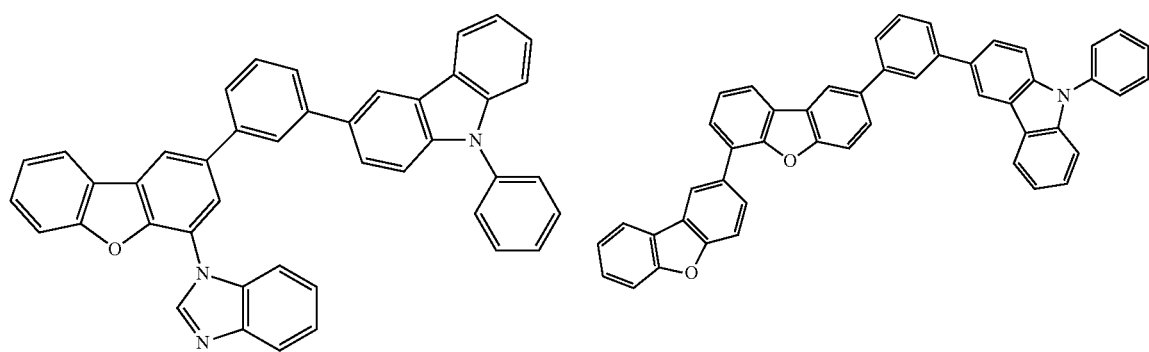

-continued
OC-67
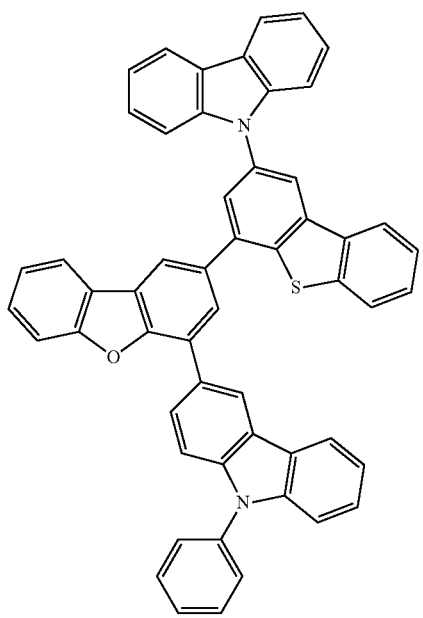
OC-68
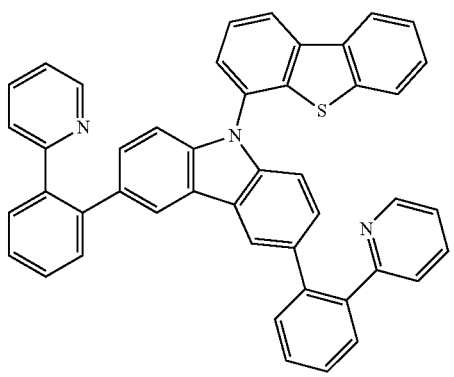
OC-69
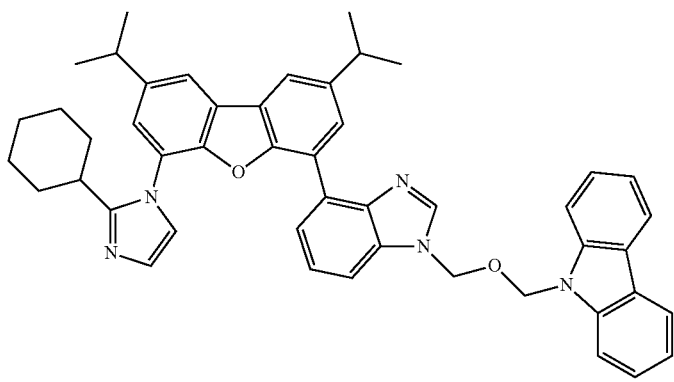
OC-70
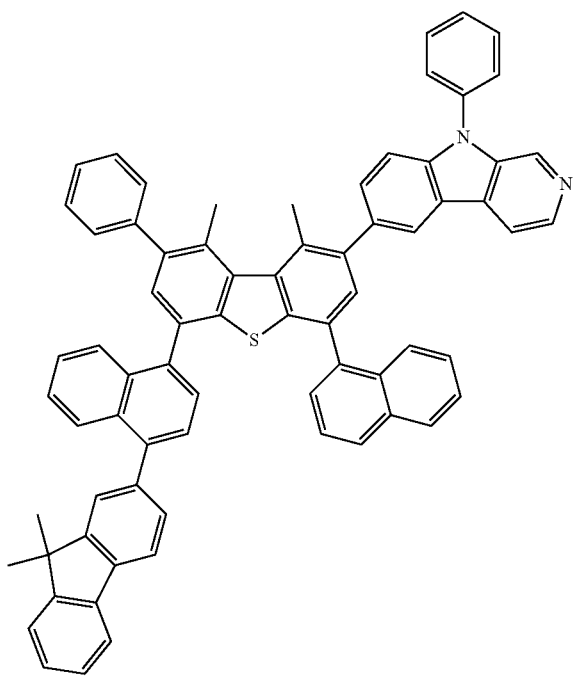

OC-71
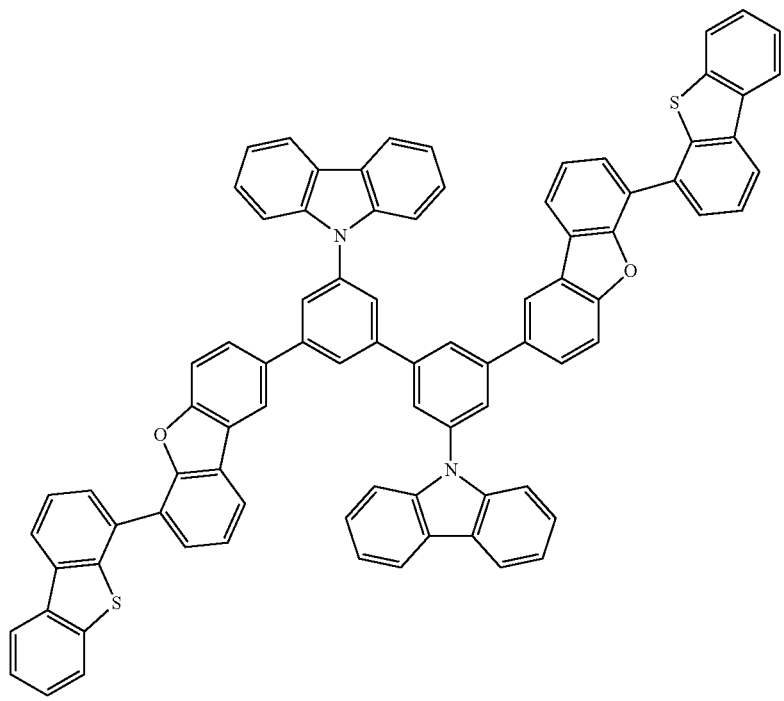
OC-72

OC-73
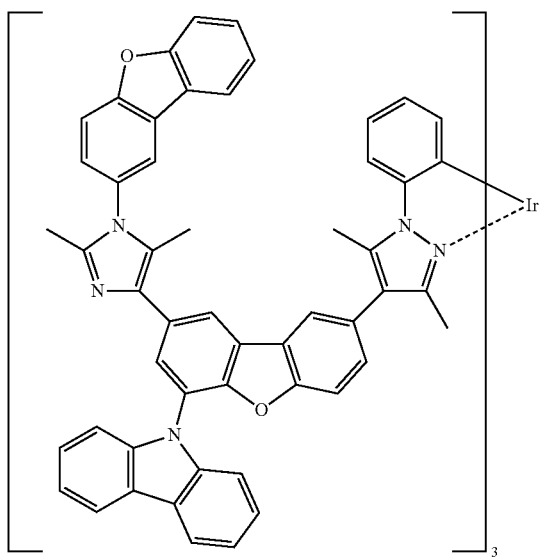
OC-74
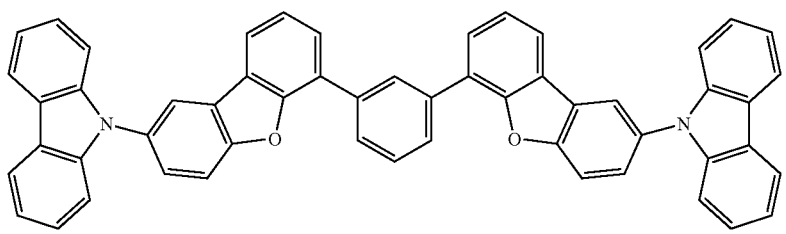
OC-75
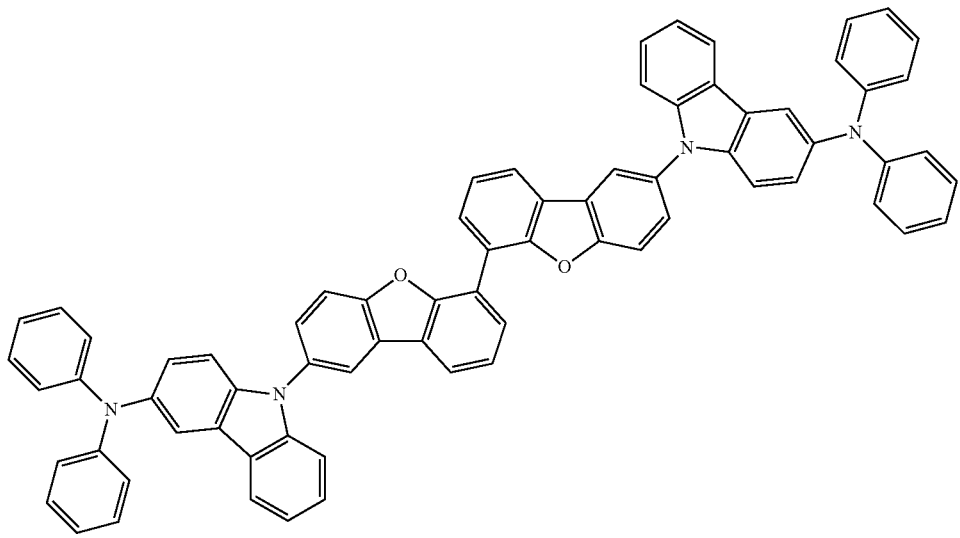

OC-76
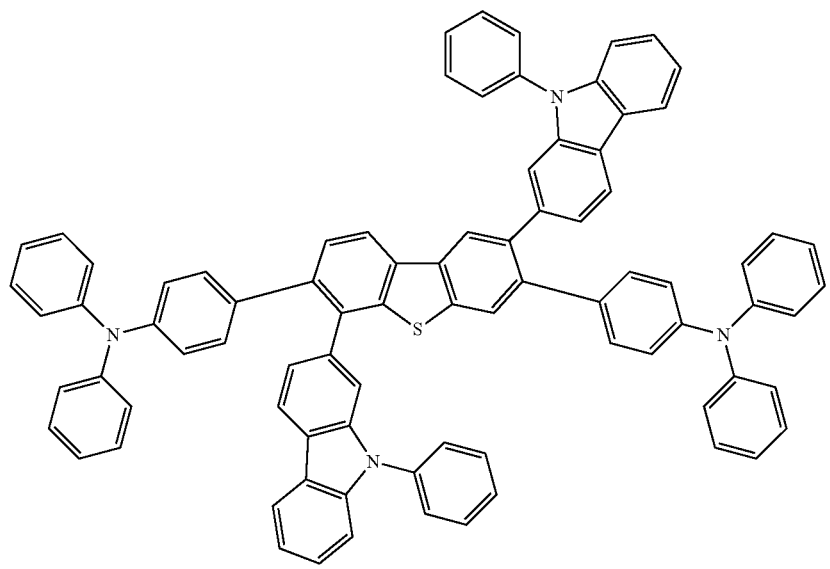
OC-77
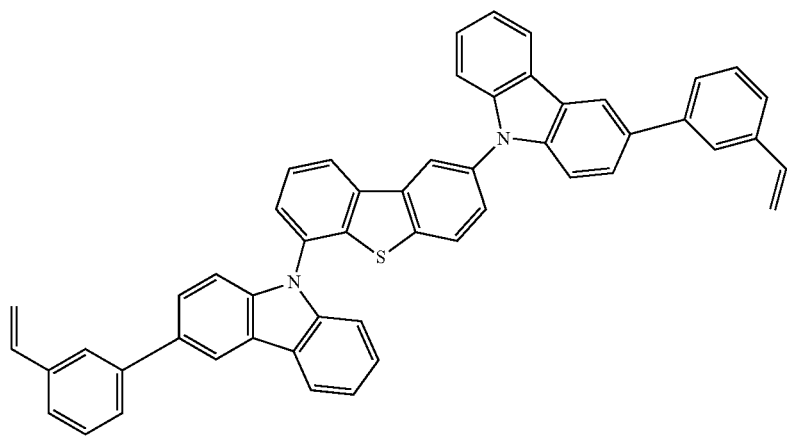
OC-78
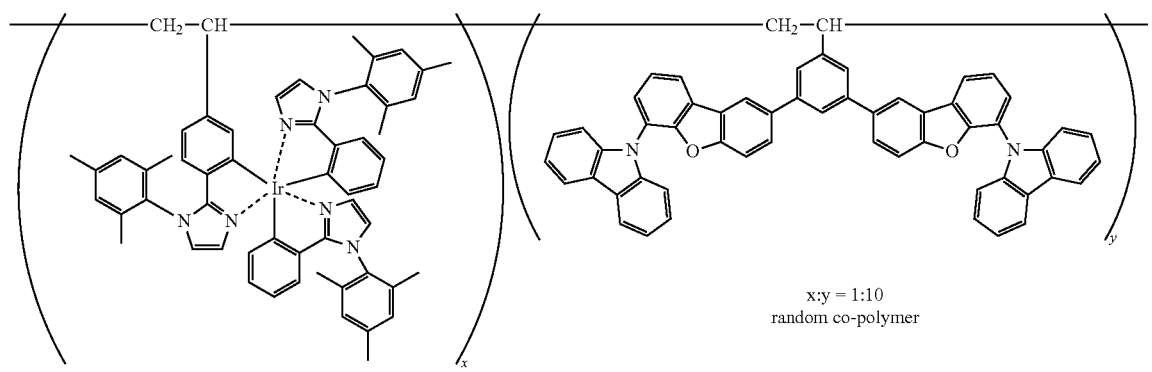
x:y = 1:10
random co-polymer OC-79
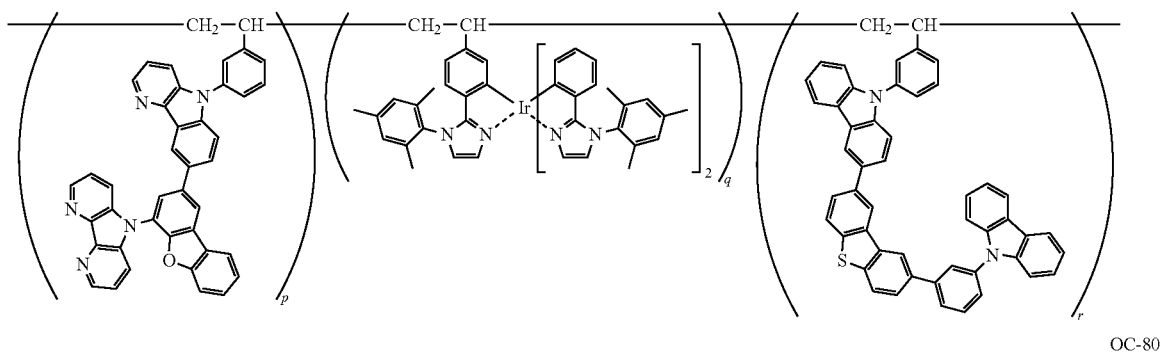
OC-80
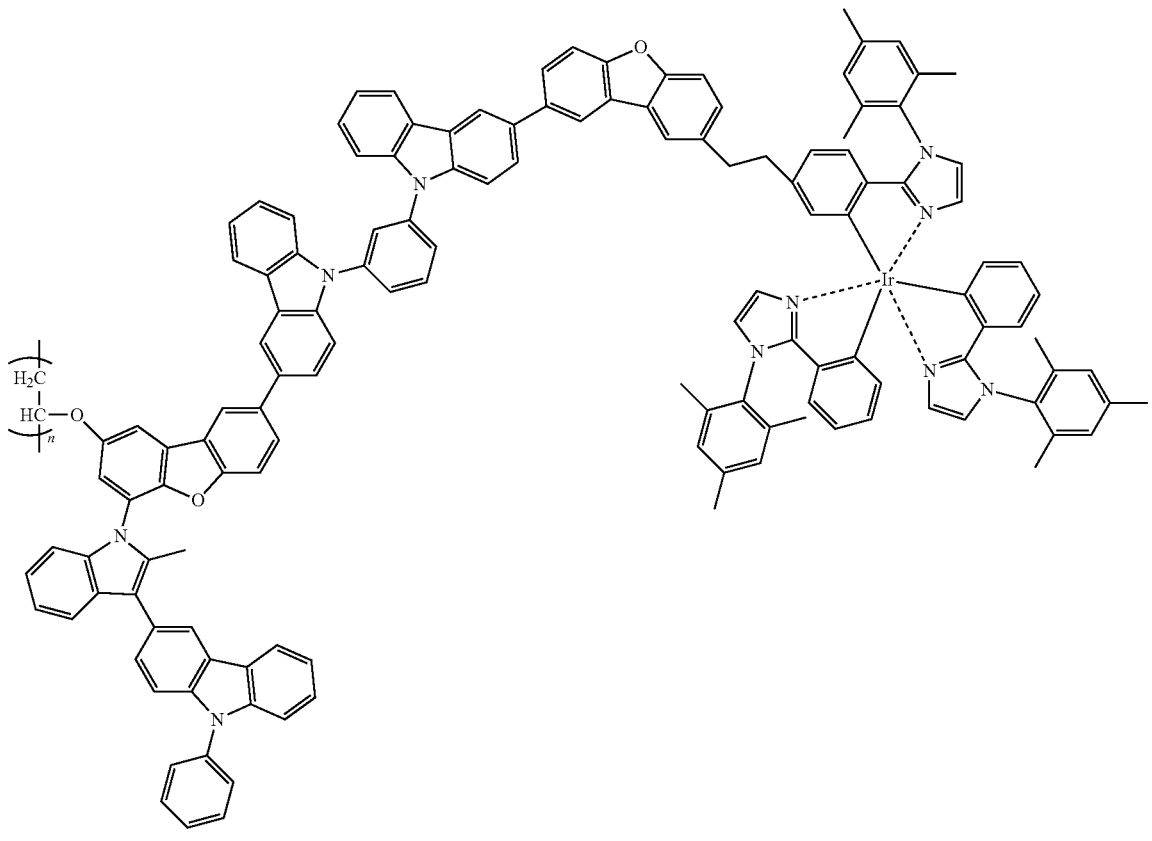
OC-81
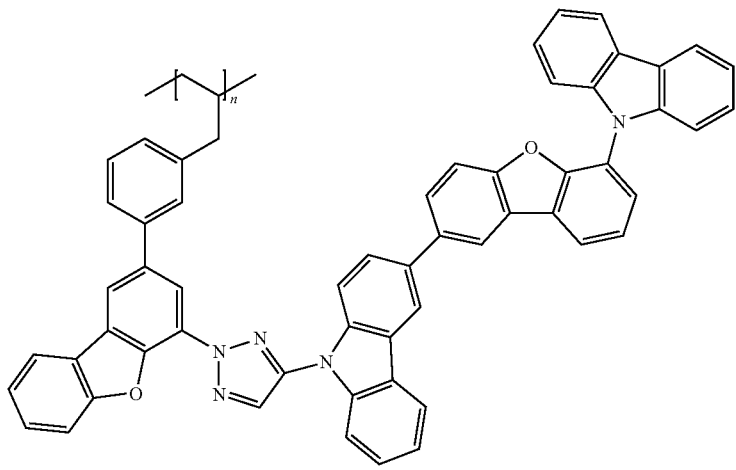

-continued
OC-82
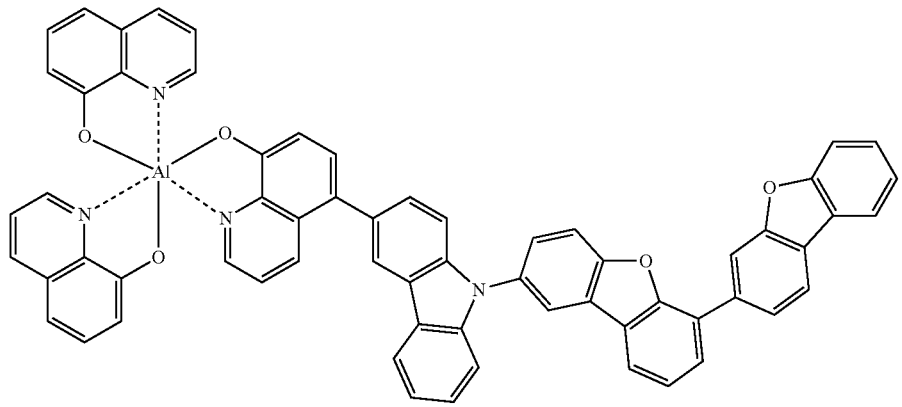
OC-83
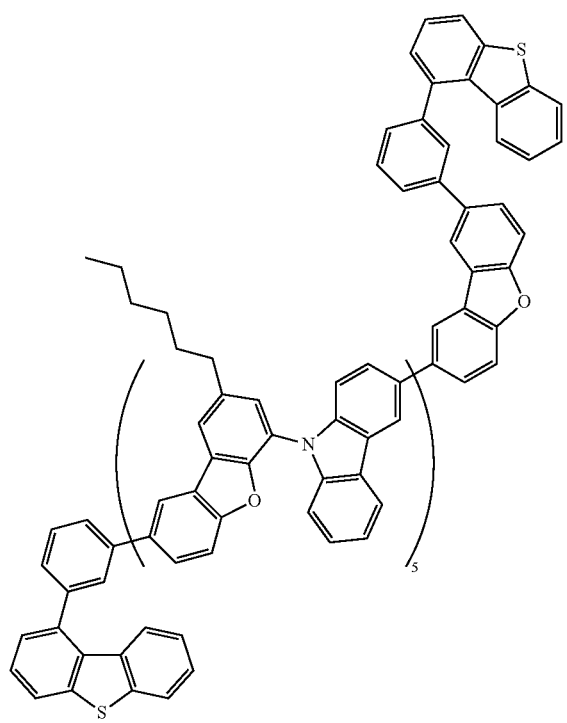
OC-84
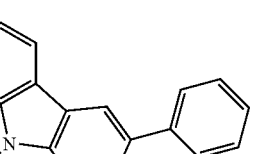
OC-85
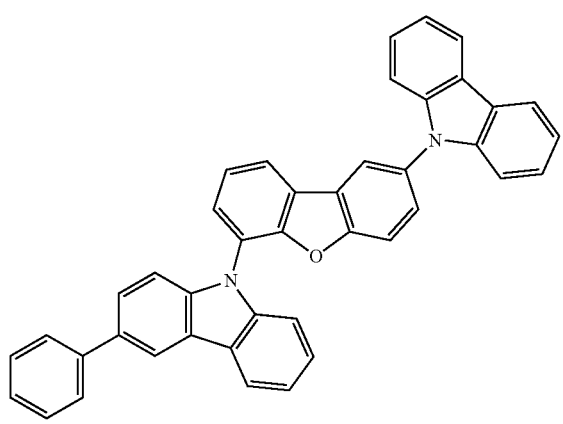
OC-86
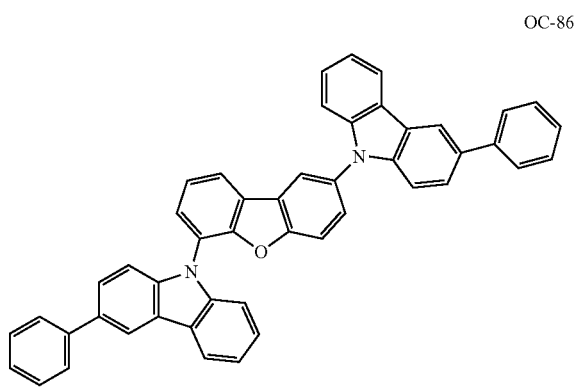

OC-87
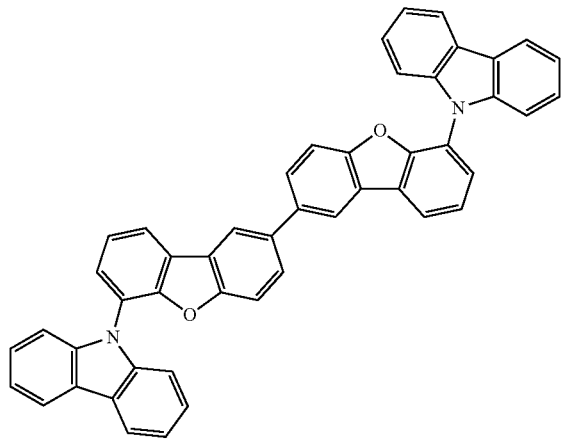
OC-88
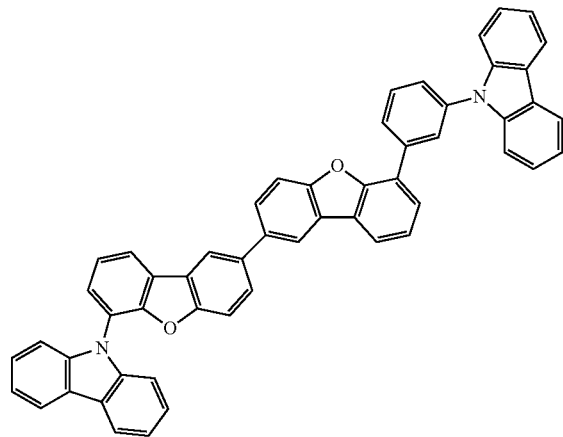
OC-89
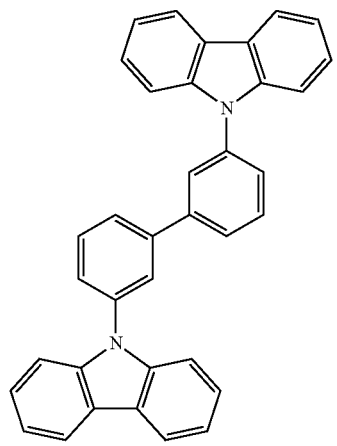
OC-90
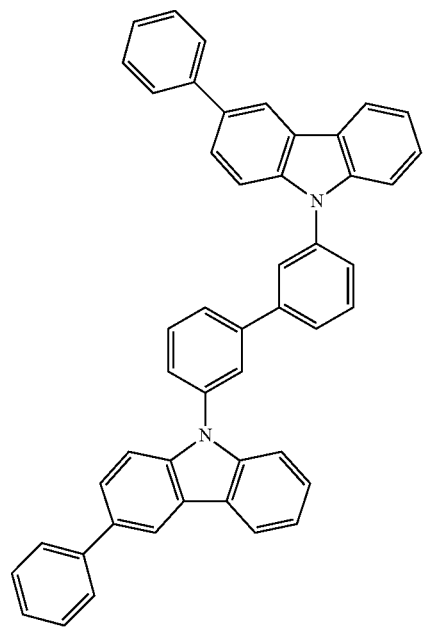
OC-91
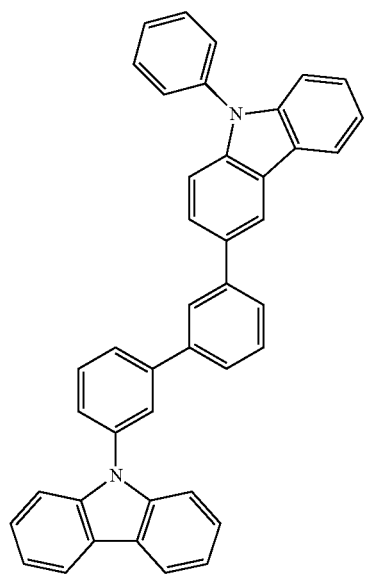

-continued

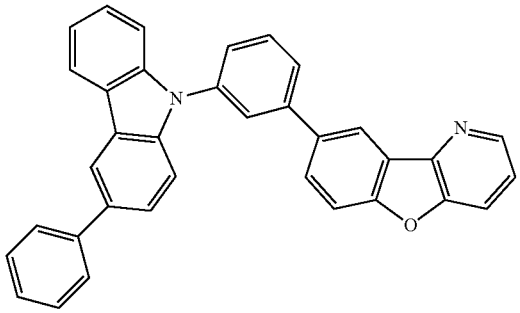
OC-92

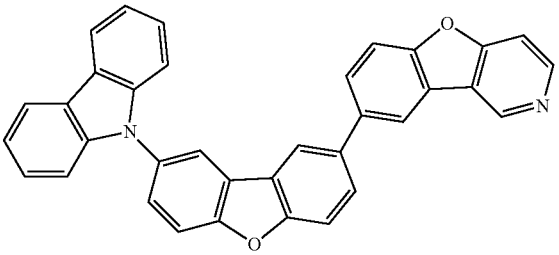
OC-93

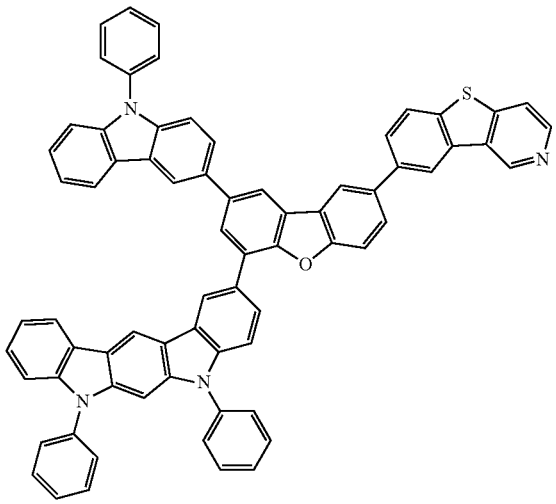
OC-94

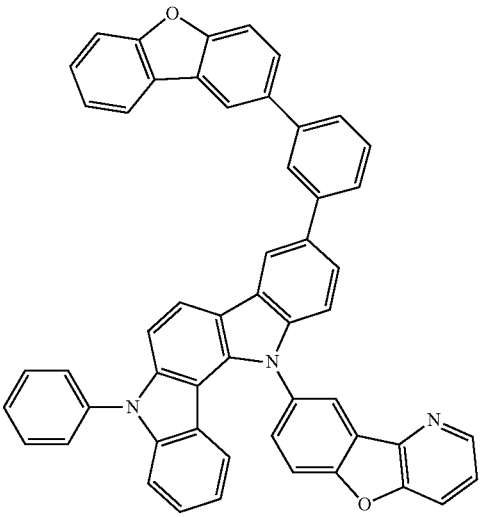
OC-95

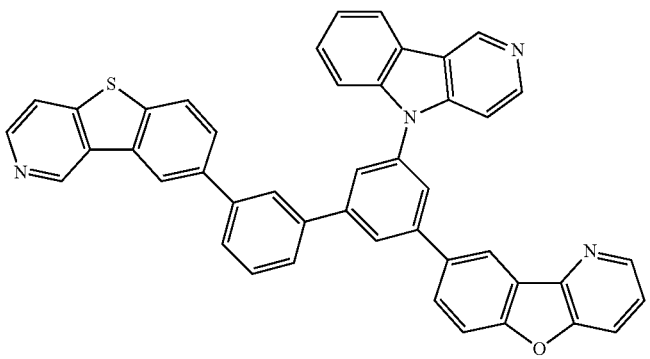
OC-96

<<Electron Transporting Layer>>

The electron transporting layer is composed of an electron transporting material, and includes an electron injecting layer and a hole blocking layer in a broad sense. The electron transporting layer can have a single-layer or multi-layer configuration.

The electron transporting layer can transport electrons injected from the cathode to the luminous layer. The electron transporting layer can be composed of any known compound. These compounds can also be used in combination.

Examples of known materials (hereinafter referred to as electron transporting material) used in the electron transporting layer include polycyclic aromatic hydrocarbons, such as nitro-substituted fluorene derivatives, diphenylquinone derivatives, thiopyran dioxide derivatives, naphthalene, and perylene; heterocyclic tetracarboxylic anhydrides; carbodiimides; fluorenylidenemethane derivatives; anthraquinodimethane and anthrone derivatives; oxadiazole derivatives; carboline derivatives or carboline derivatives having a ring structure in which at least one carbon atom of a hydrocarbon ring in the carboline ring is replaced with a nitrogen atom; and hexaazatriphenylene derivatives.

Examples of usable electron transporting materials include thiadiazole derivatives prepared by replacing an oxygen atom of an oxadiazole ring in the oxadiazole derivatives with a sulfur atom, and quinoxaline derivatives having a quinoxaline ring known as an electron-withdrawing group.

These electron transporting materials can also be used in the form of polymer materials composed of these materials introduced into polymer chains or polymers having main chains composed of electron transporting these materials.

Further examples of the usable electron transporting materials include metal complexes of 8-quinolinol derivatives, such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, and bis(8-quinolinol) zinc (Znq); and metal complexes in which the central metals of these metal complexes are replaced with In, Mg, Cu, Ca, Sn, Ga, or Pb.

Other examples of the usable electron transporting materials include metal-free or metal phthalocyanines, or those having terminals replaced with an alkyl group or a sulfonate group. Other usable electron transporting materials are inorganic semiconductors, such as n-Si and n-SiC semiconductors.

The electron transporting layer is preferably formed with an electron transporting material which is shaped into a thin film by a vacuum evaporation or wet process, for example, spin coating, casting, die coating, blade coating, roll coating, inkjetting, printing, spray coating, curtain coating, or Langmuir Blodgett (LB) process.

The electron transporting layer can have any thickness. The thickness is within the range of usually about 5 nm to 5000 nm, preferably 5 nm to 200 nm. The electron transporting layer may have a single layer structure composed of one or more of these materials.

The electron transporting layer may be doped with an n-type dopant composed of a metal compound, such as a metal complex or a halogenated metal.

Non-limiting examples of the known compound (electron transporting material) preferably used in formation of the electron transporting layer of the organic EL element according to the present invention are shown below:

ET-1

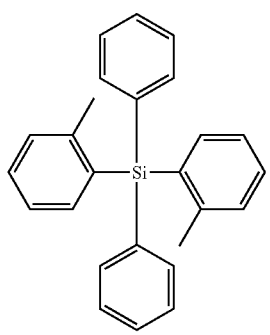

ET-2(BCP)

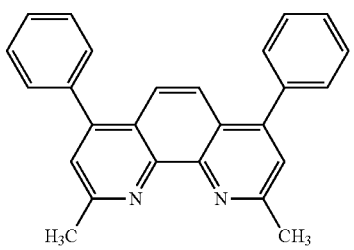

ET-3(PBD)

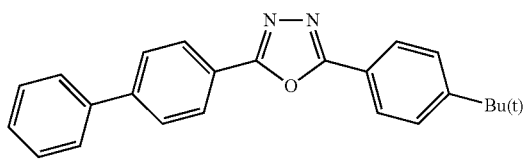

ET-4

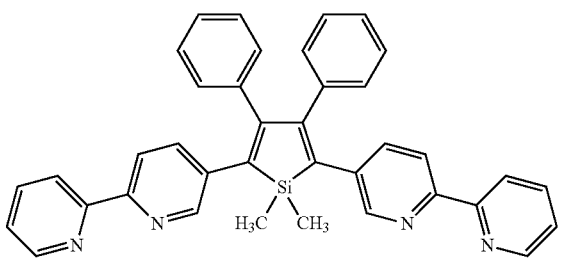

ET-5

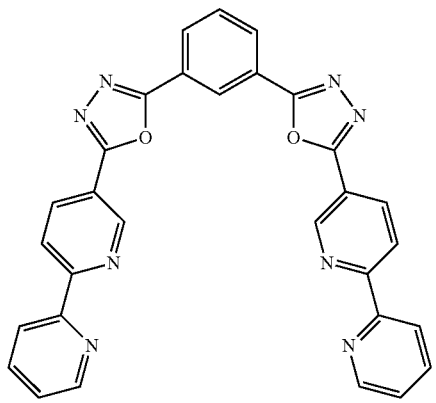

ET-6

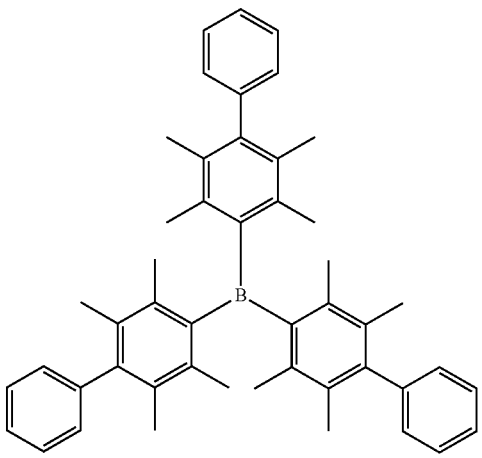

-continued
ET-7(Alq3)
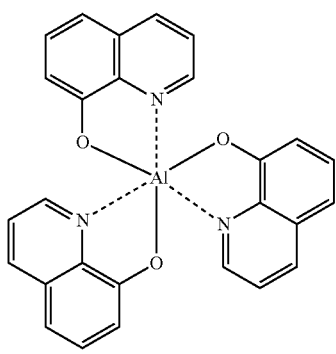
ET-8(BAlq)
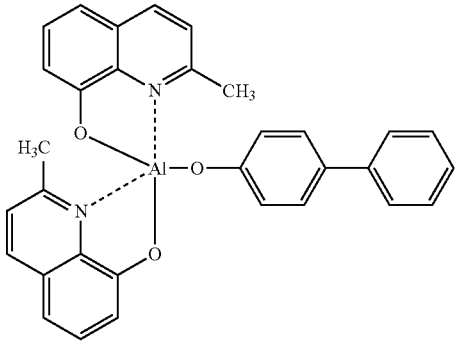
ET-9
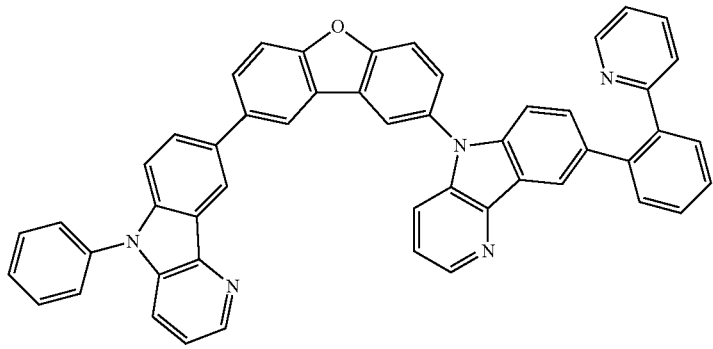
ET-10
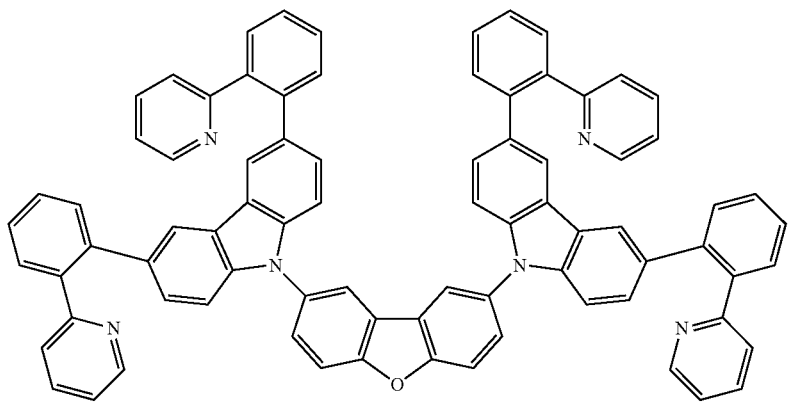
ET-11
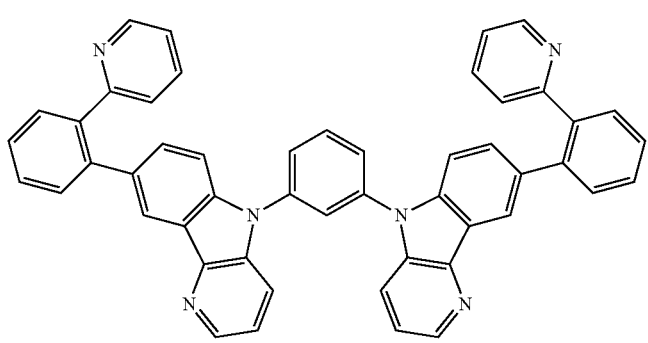

-continued
ET-12
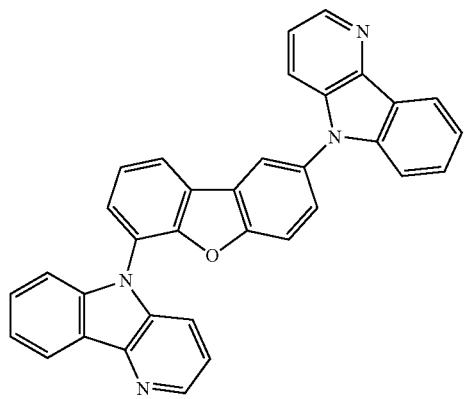
ET-13
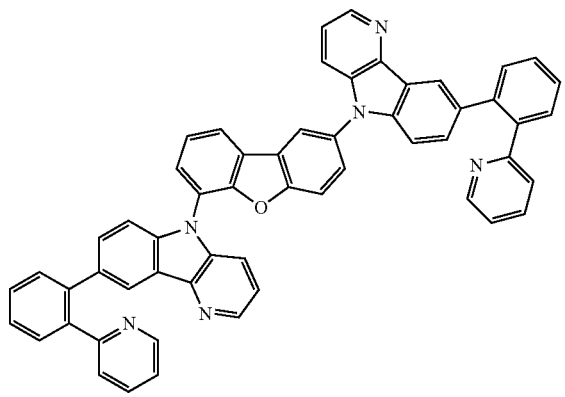
ET-14
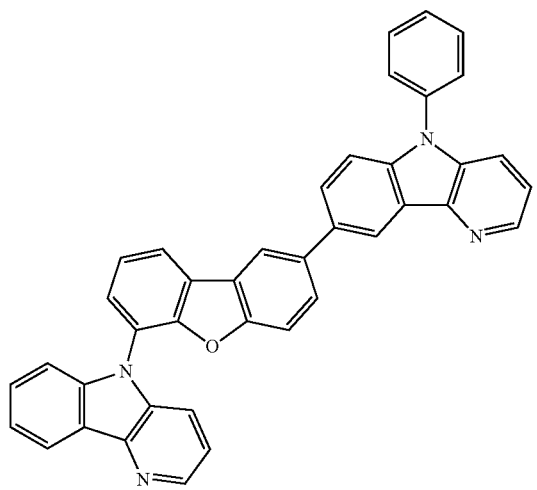
ET-15
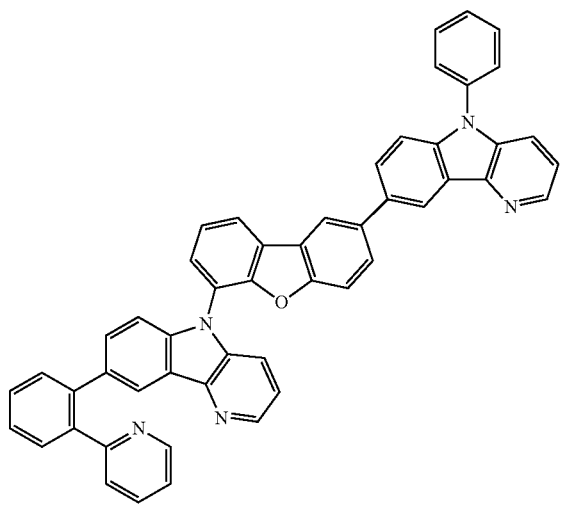
ET-16
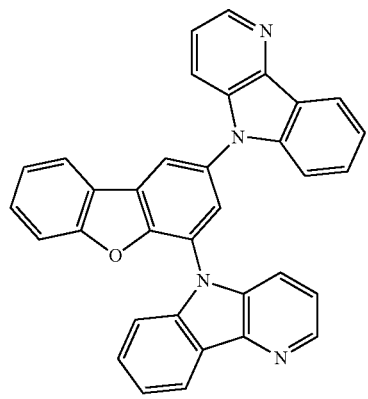
ET-17
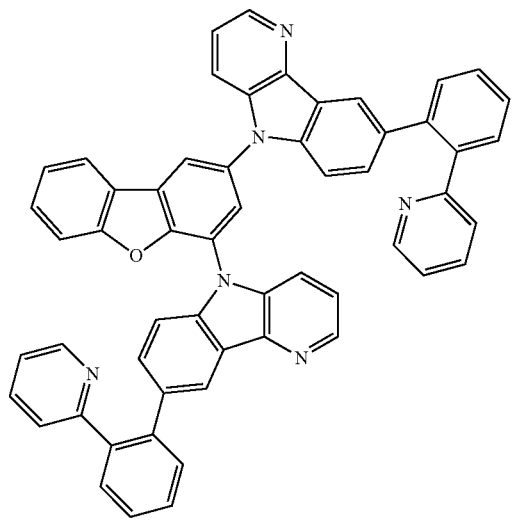

-continued
ET-18
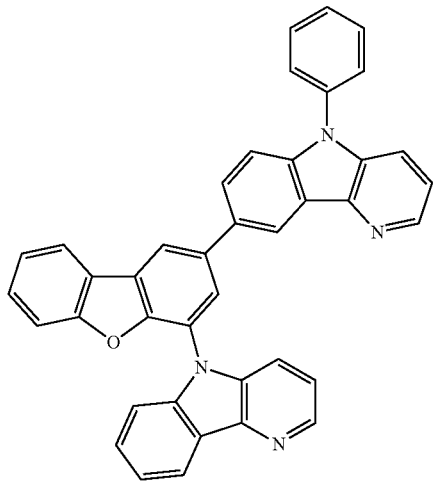
ET-19
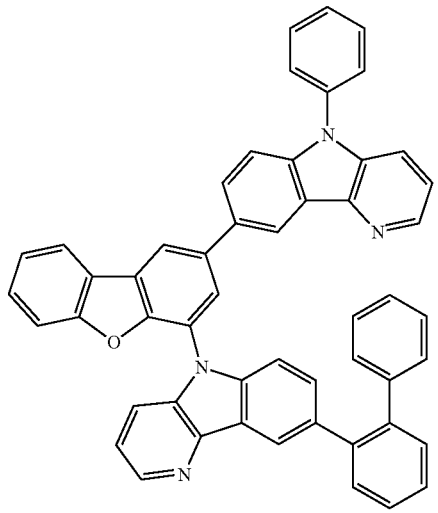
ET-20
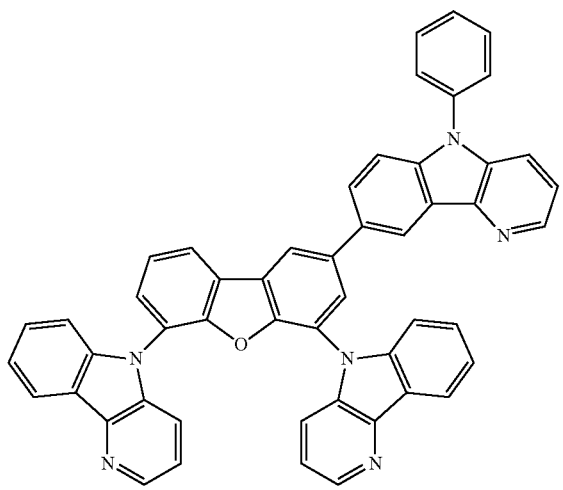
ET-21
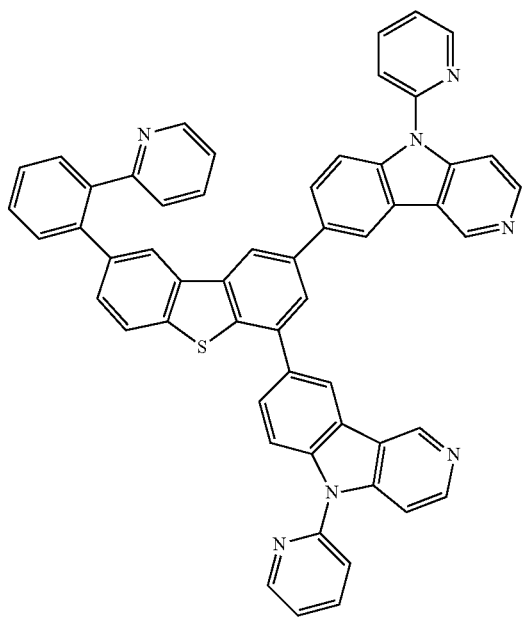
ET-22
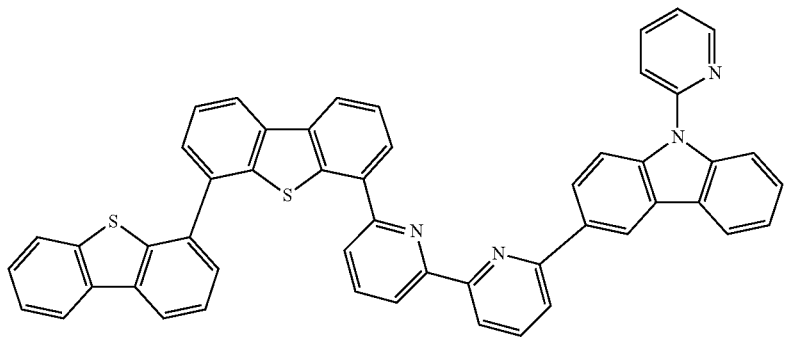

ET-23
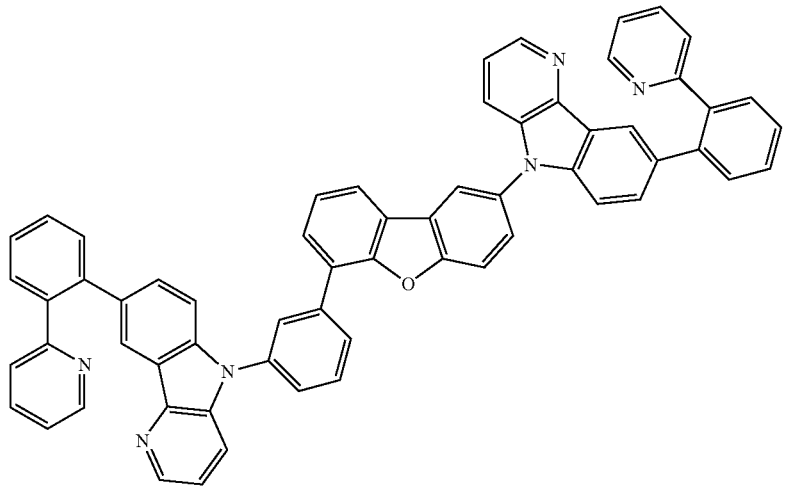
ET-24
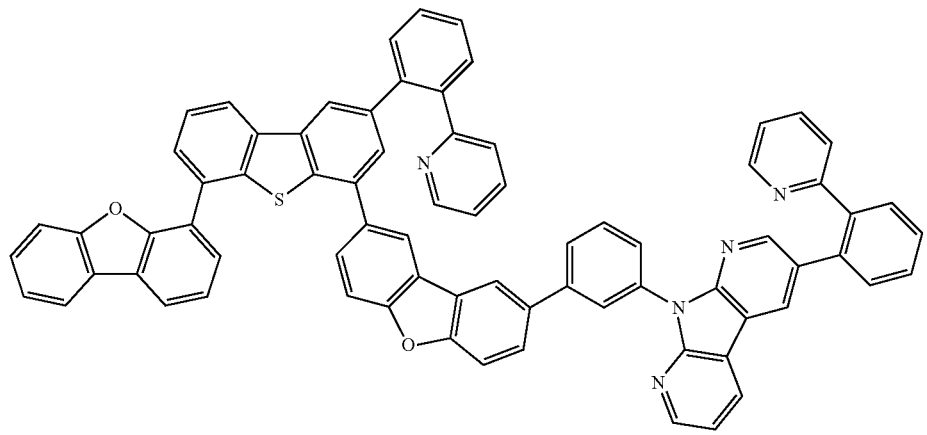
ET-25
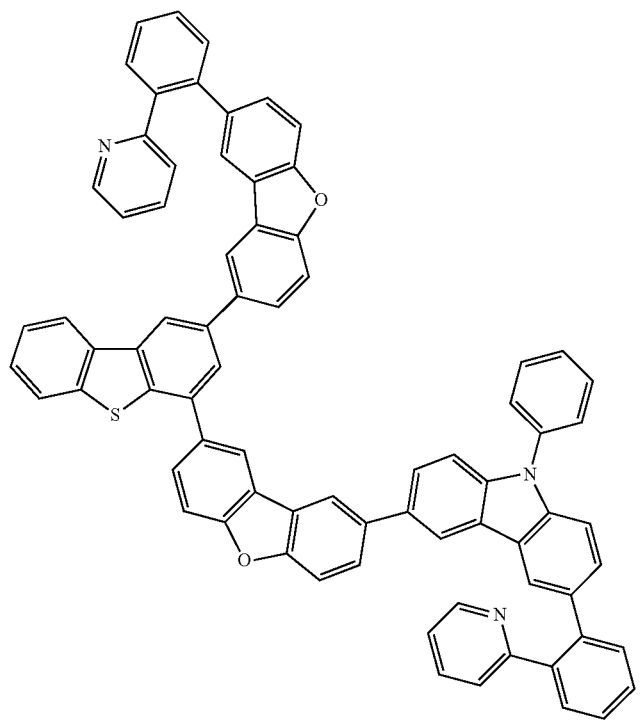

-continued
ET-26
ET-27
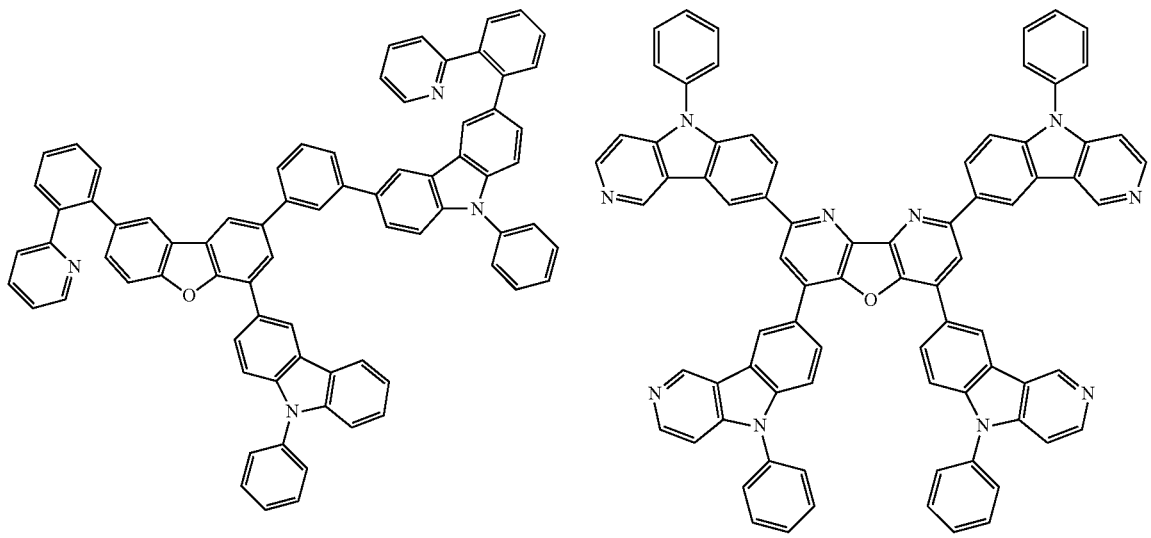
ET-28
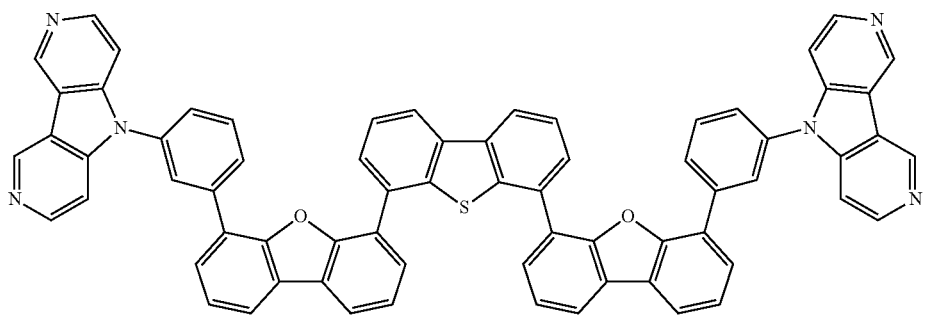
ET-29
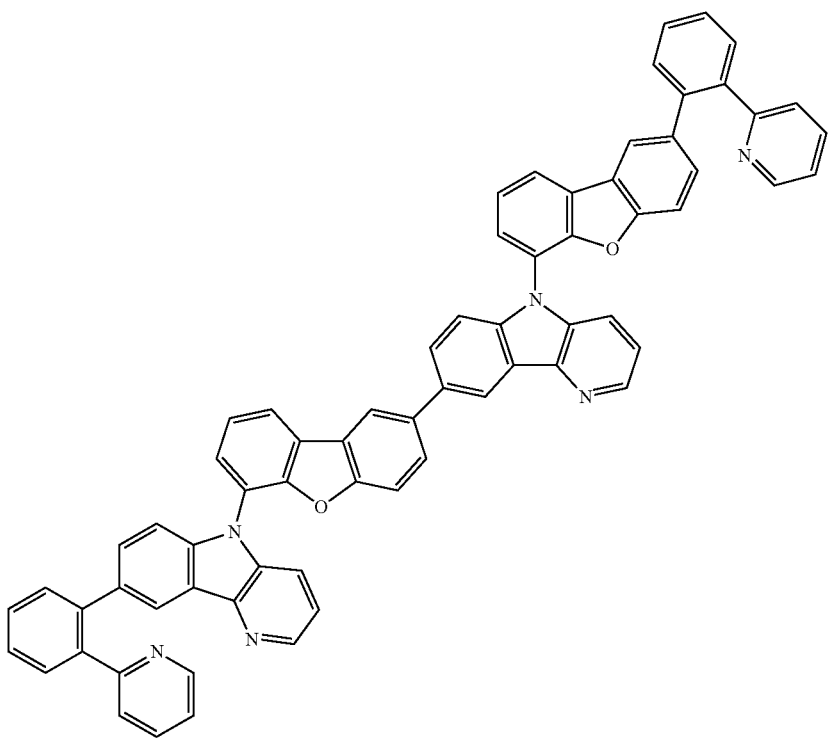

-continued
ET-30
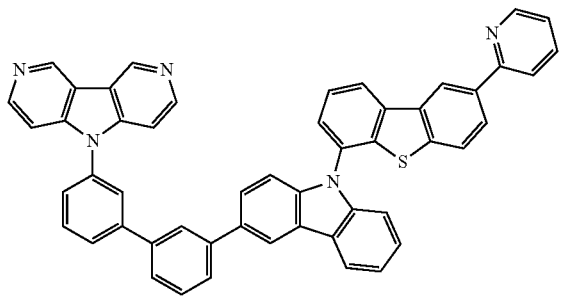
ET-31
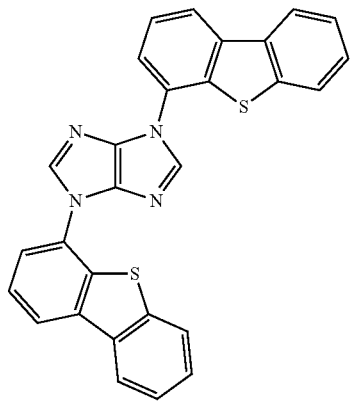
ET-32
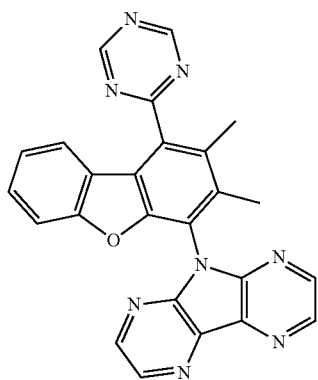
ET-33
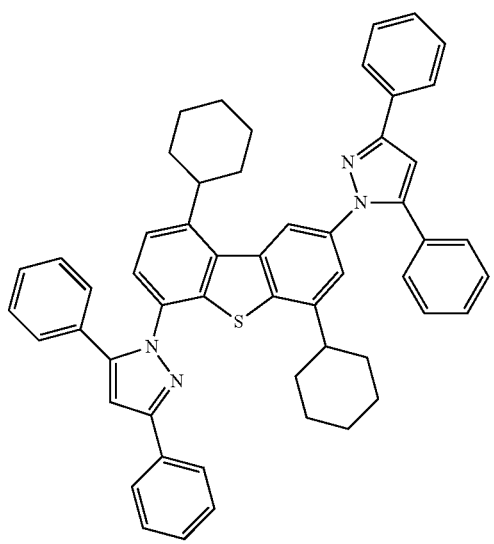
ET-34
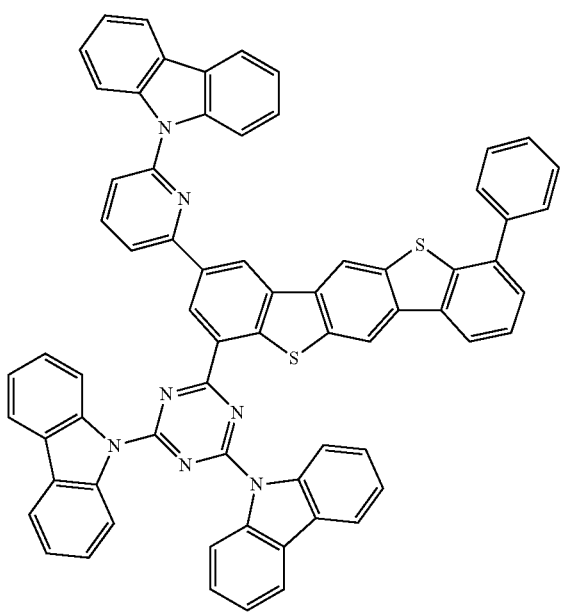
ET-35
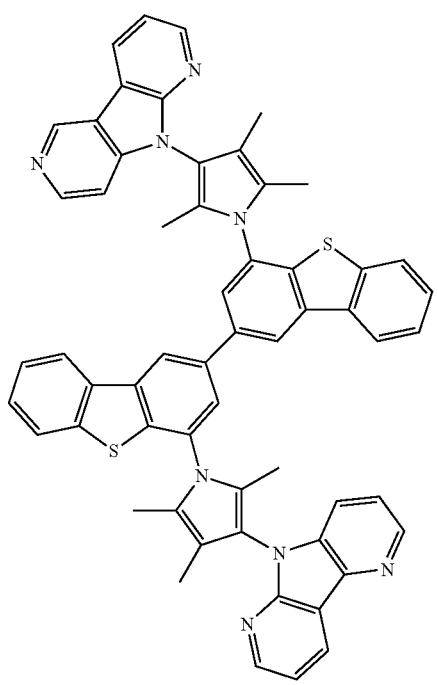

-continued
ET-36
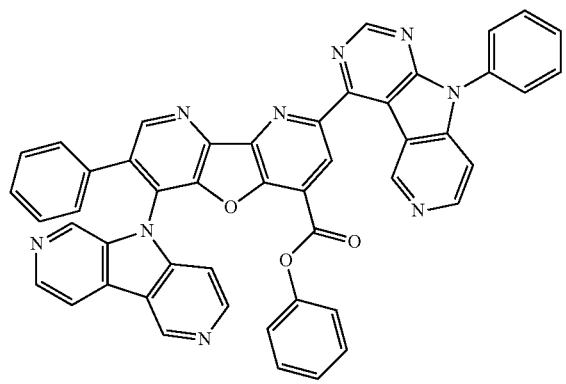
ET-37
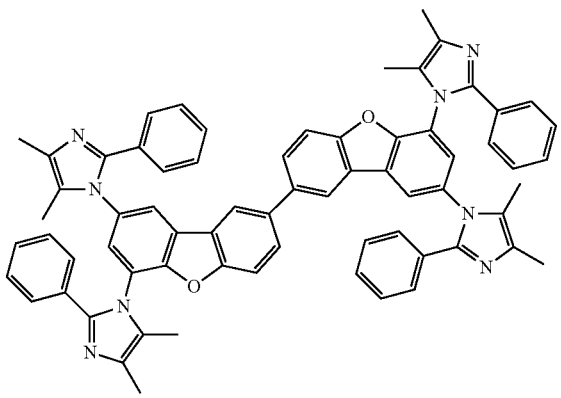
ET-38
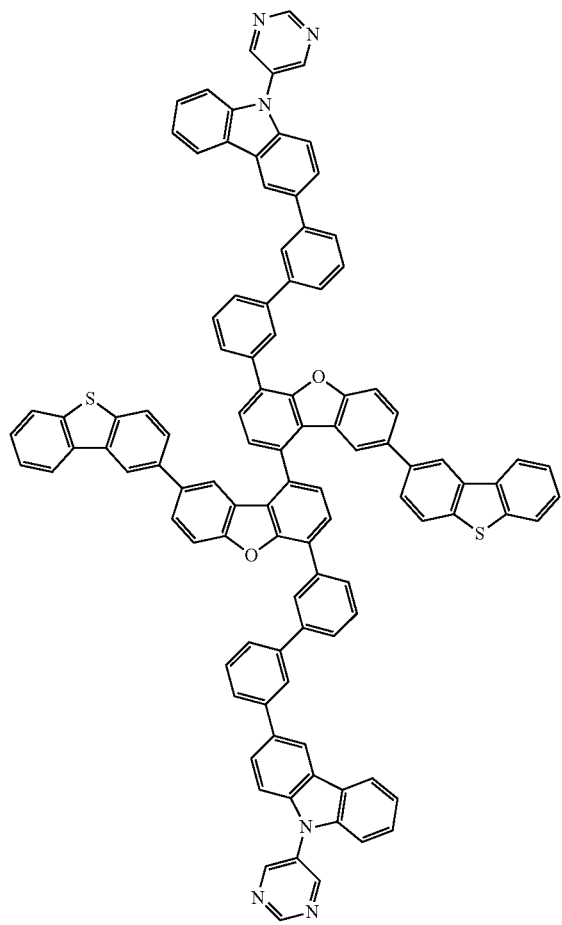
ET-39
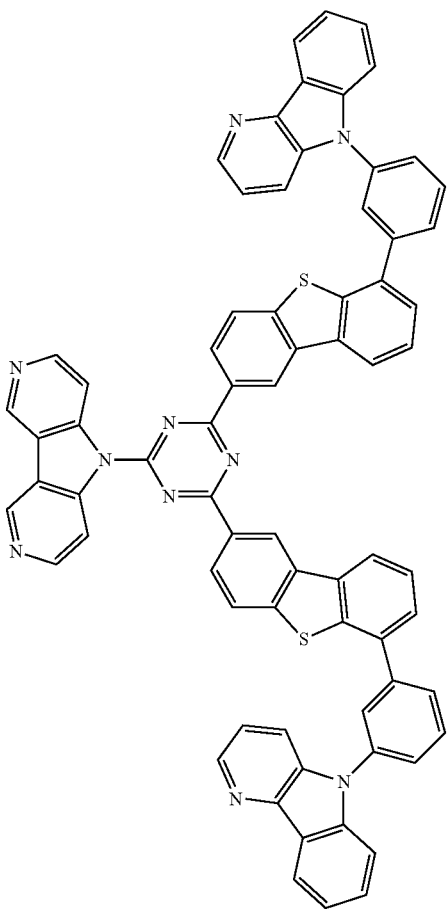

ET-40

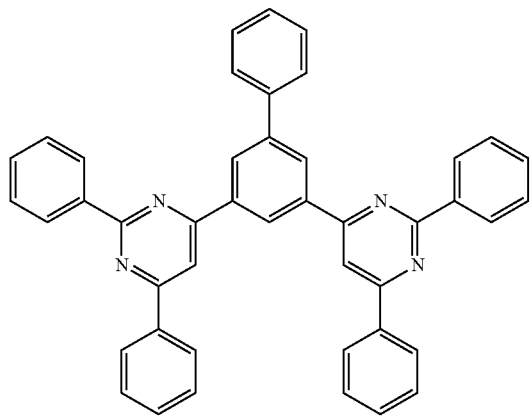

ET-41

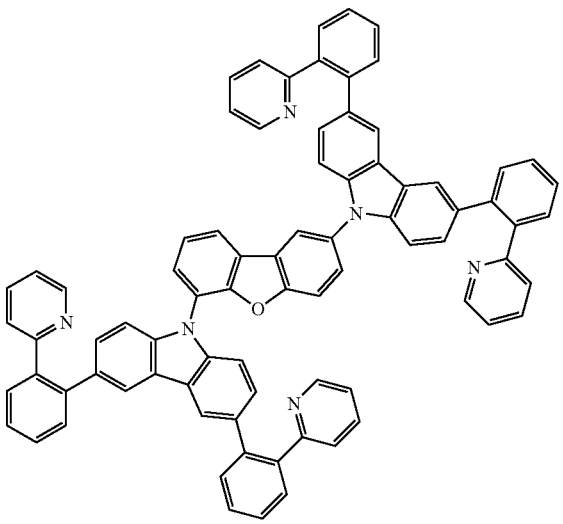

ET-42

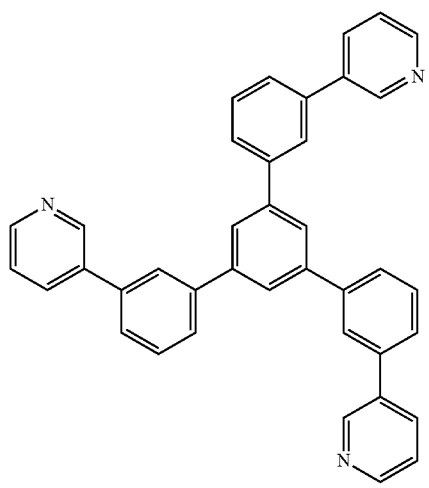

ET-43

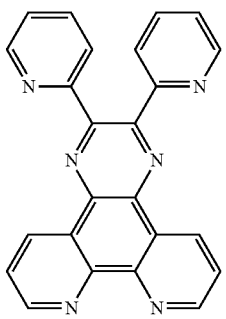

These electron transporting materials can also be used as host compounds for the luminous layer.

<<Cathode>>

The cathode used in the present invention is composed of an electrode material having small work functions (4 eV or less). Examples of such materials include metals (referred to as electron injecting metals) and alloys thereof, and conductive compounds, and mixtures thereof. Specific examples of such electrode materials include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, and rare earth metals. Among these electrode materials, suitable are mixtures of electron injecting metals and second metals having stability because of their work functions larger than those of electron injecting metals, such as magnesium/silver mixtures, magnesium/aluminum mixtures, magnesium/indium mixtures, aluminum/aluminum oxide ($Al_2O_3$) mixtures, lithium/aluminum mixtures, and aluminum in view of durability to electron injection and oxidation.

These electrode materials can be formed into a thin film by a process, such as deposition or sputtering, to prepare a cathode. The cathode preferably has a sheet resistance of several hundreds ohms per square or less and a thickness in the range of usually 10 nm to 5 μm, preferably 50 to 200 nm.

The organic EL element preferably transmits light emission through a transparent or translucent anode or cathode to enhance the luminance of the light emission.

The metal can be deposited on the cathode in a thickness of 1 to 20 nm, and a conductive transparent material listed in description of the anode described later can be disposed thereon to prepare a transparent or translucent cathode. This process can be used to prepare an element including an anode and a cathode both having transmittance.

<<Injecting Layer: Electron Injecting Layer (Cathode Buffer Layer), Hole Injecting Layer>>

The injecting layer is disposed when necessary. The injecting layer includes an electron injecting layer and a hole injecting layer, and may be disposed between the anode and the luminous layer or the hole transporting layer and between the cathode and the luminous layer or the electron transporting layer. The injecting layer is disposed between an electrode and an organic layer to reduce start-up voltage and enhance the luminance of the light emission, and is described in detail in Chapter 2 "Denkyoku zairyo (Electrode material)" (pp. 123 to 166) of Yuki EL Soshi to Sonokougyouka Saizensen (Organic electroluminescent elements and Their Frontiers of Industrial Applications) vol. 2 (Nov. 30, 1998, published by NTS Inc.). The injecting layer includes a hole injecting layer (anode buffer layer) and an electron injecting layer (cathode buffer layer).

The details of the anode buffer layer (hole injecting layer) are also described in Japanese Patent Application Laid-Open Nos. H9-45479, H9-260062, and H8-288069. Specific examples of the anode buffer layer include phthalocyanine buffer layers containing compounds, such as copper phthalocyanine; hexaazatriphenylene derivative buffer layers described in Japanese Unexamined Patent Application Publication (Tokuhyo) No. 2003-519432 and Japanese Patent Application Laid-Open No. 2006-135145; oxide buffer layers containing oxides, such as vanadium oxide; amorphous carbon buffer layers; polymer buffer layers containing conductive polymers, such as polyaniline (emeraldine) and polythiophene; and ortho-metalated complex layers containing complexes, such as tris(2-phenylpyridine)iridium complex.

The details of the cathode buffer layer (electron injecting layer) are also described in Japanese Patent Application Laid-Open Nos. H6-325871, H9-17574, and H10-74586. Specific examples thereof include metal buffer layers containing metals, such as strontium and aluminum; alkali metal compound buffer layers containing alkali metal compounds, such as lithium fluoride and potassium fluoride; alkaline earth metal compound buffer layers containing alkaline earth metal compounds, such as magnesium fluoride and cesium fluoride; and oxide buffer layers containing oxides, such as aluminum oxide. The buffer layer (injecting layer) is desirably a thin film having a thickness in the range of preferably 0.1 nm to 5 μm.

<<Blocking Layer: Hole Blocking Layer, Electron Blocking Layer>>

The blocking layer is disposed when necessary in the basic constitutional layers of a thin film composed of the organic compound. Examples thereof include hole blocking layers described in Japanese Patent Application Laid-Open Nos. H11-204258 and H11-204359, and Yuki EL Soshi to Sonokougyouka Saizensen (Organic electroluminescent elements and Their Frontiers of Industrial Applications), Nov. 30, 1998, published by NTS Inc.), p. 237.

The hole blocking layer in a broad sense functions as an electron transporting layer. The hole blocking layer is composed of a hole blocking material having electron transportability while having significantly low hole transportability. The hole blocking layer can block holes while transporting electrons, thereby increasing the opportunities of recombination between electrons and holes.

The hole blocking layer according to the present invention can have the same configuration as that of the electron transporting layer when necessary.

The hole blocking layer of the organic EL element according to the present invention is preferably disposed adjacent the luminous layer.

The hole blocking layer preferably contains the host compounds listed above, such as carbazole derivatives, carboline derivatives, and diazacarbazole derivatives (in which at least one carbon atom of the carboline ring is replaced with a nitrogen atom).

If a plurality of luminous layers emitting light beams having different colors is included in the present invention, a luminous layer, among all of the luminous layers, emitting a light beam at a local maximum at the shortest wavelength is preferably disposed nearest to the anode. In such a case, the hole blocking layer is preferably disposed between the shortest wavelength layer and the second nearest luminous layer to the anode. More preferably, the hole blocking layer disposed in this position contains 50 mass % or more compound having an ionization potential of 0.3 eV or more greater than that of the host compound contained in the shortest wavelength luminous layer.

The ionization potential is defined as energy required for release of electrons at the highest occupied molecular orbital (HOMO) level of a compound to the vacuum level, and can be determined by the following methods:

(1) The ionization potential can be determined with Gaussian 98 software for molecular orbital calculation (Gaussian 98, Revision A. 11.4, M. J. Frisch, et al., made by Gaussian, Inc., Pittsburgh Pa., the United States, 2002.) as a value (in eV unit) through optimization of the structure with a keyword B3LYP/6-31G*. The effectiveness of this calculated value is supported by a high correlation between the calculated value with this software and the experimental value.

(2) The ionization potential can also be directly determined by photoelectric spectroscopy. For example, the ionization potential can be suitably determined with a low energy electron spectrometer "Model AC-3" Riken Keiki Co., Ltd. or by ultraviolet photoelectron spectroscopy.

The electron blocking layer in a broad sense functions as a hole transporting layer. The electron blocking layer is composed of a material having hole transportability while having significantly low electron transportability. The electron blocking layer can block electrons while transporting holes, thereby increasing the opportunities of recombination between electrons and holes.

The electron blocking layer can have the same configuration as that of the hole transporting layer described later when necessary. The hole blocking layer and the electron transporting layer according to the present invention each have a thickness of preferably 3 to 100 nm, more preferably 5 to 30 nm.

<<Hole Transporting Layer>>

The hole transporting layer in a broad sense is composed of a hole transporting material having hole transportability, and includes the hole injecting layer and the electron blocking layer. The hole transporting layer can have a single-layer or multi-layer configuration.

The hole transporting material can be an organic or inorganic substance that has hole injection ability, hole transportability, or electron blocking ability. Examples of the hole transporting material include triazole derivatives, oxadiazole derivatives, imidazole derivatives, polyarylalkane derivatives, pyrazoline derivatives, pyrazolone derivatives, phenylenediamine derivative, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, and conductive higher oligomers, particularly thiophene oligomers.

Examples of the hole transporting material include azatriphenylene derivatives described in Japanese Unexamined Patent Application Publication (Tokuhyo) No. 2003-519432 and Japanese Patent Application Laid-Open No. 2006-135145.

These hole transporting materials can be used. Among these materials, preferred are porphyrin compounds, aromatic tertiary amine compounds, and styrylamine compounds, and particularly preferred are aromatic tertiary amine compounds.

Typical examples of the aromatic tertiary amine compounds and styrylamine compounds include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino)quadriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbene; N-phenylcarbazole; compounds having two condensed aromatic rings in the molecules, such as 4,4'-bis[N-(1-naphthyl)-N-phenylamino]biphenyl (NPD), described in U.S. Pat. No. 5,061,569; and compounds having three triphenyl amine units connected into a star burst shape, such as 4,4',4"-tris[N-(3-methylphenyl)-N-phenylamino]triphenylamine (MTDATA), described in Japanese Patent Application Laid-Open No. H4-308688.

These hole transporting materials can also be used in the form of polymer materials composed of these materials introduced into polymer chains or polymers having main chains composed of these materials.

Other usable hole injecting materials and hole transporting materials are inorganic compounds, such as p-Si and p-SiC semiconductors.

These materials also include the so-called p-type hole transporting materials described in Japanese Patent Application Laid-Open No. H11-251067 and J. Huang, et al., Applied Physics Letters 80 (2002), p. 139. These materials are preferably used in the present invention to attain luminescent elements with enhanced efficiency.

The hole transporting layer can be formed with a hole transporting material which is shaped into a thin film by a known process, such as vacuum evaporation, spin coating, casting, printing including inkjetting, or LB process.

The hole transporting layer can have any thickness. The thickness is within the range of usually about 5 nm to 5 μm, preferably 5 to 200 nm. The hole transporting layer can have a single-layer structure composed of one or more of the materials.

The hole transporting layer can also be doped with any impurity to enhance p-characteristics. Examples of such doped hole transporting layers include those described in Japanese Patent Application Laid-Open Nos. H4-297076, 2000-196140, and 2001-102175, and J. Appl. Phys., 95, 5773 (2004).

Such a hole transporting layer having high p-characteristics is preferably used in the present invention to attain organic EL elements having low power consumption.

<<Anode>>

The anode of the organic EL element is preferably composed of any electrode material having a large work function (4 eV or more). Examples of such materials include metals and alloys thereof and conductive compounds and mixtures thereof. Specific examples of such electrode materials include metals, such as Au, and conductive transparent materials, such as CuI, indium tin oxide (ITO), $SnO_2$, and ZnO.

The anode may be composed of a material, such as $In_2O_3$—ZnO (IDIXO), which can be prepared into an amorphous transparent conductive film. The anode may be in the form of a thin film formed through deposition or sputtering of such an electrode material, and may be etched into a desired pattern by photolithography. If high patterning accuracy is not required (about 100 μm or more), the pattern may be formed through a mask having a desired pattern by deposition or sputtering of the electrode material into a thin film.

Any coating material, such as an organic conductive compound, can also be formed into a film by a wet process, such as printing or coating. The anode should preferably have a transmittance of more than 10% to transmit emitted light. The anode preferably has a sheet resistance of several hundreds ohms per square or less. The thickness is selected from the range of usually 10 to 1000 nm, preferably 10 to 200 nm although it depends on the material.

<<Support Substrate>>

The organic EL element according to the present invention can be composed of any support substrate (hereinafter also referred to as base, substrate, base material, and support). The support substrate may be composed of glass or plastics, and may be transparent or opaque. If the transparent support substrate extracts light therefrom, the substrate should preferably be transparent. Examples of preferred transparent support substrate materials include glass, quartz, and transparent resin films. Particularly preferred support substrates are resin films which impart flexibility to organic EL elements.

Examples of the resin films include polyesters, such as poly(ethylene terephthalate) (PET) and poly(ethylene naphthalate) (PEN); polyethylene; polypropylene; cellophane; cellulose esters, such as cellulose diacetate, cellulose triacetate (TAC), cellulose acetate butyrate, cellulose acetate propionate (CAP), cellulose acetate terephthalate, and cellulose nitrate or derivatives thereof; poly(vinylidene chloride); poly(vinyl alcohol); poly(ethylenevinyl alcohol); syndiotactic polystyrenes; polycarbonates; norbornene resins; polymethylpentene; polyether ketone; polyimides; poly(ether sulfone) (PES); poly(phenylene sulfide); polysulfones; polyether imides; polyether ketone imide; polyamides; fluorinated resins; nylon; poly(methyl methacrylate); acrylates or polyarylates; and cycloolefin resins, such as ARTON (trade name, made by JSR Corporation) and APEL (trade name, made by Mitsui Chemicals, Inc.).

The resin film may have a coating film of an inorganic or organic material or an inorganic/organic hybrid coating film on the surface thereof. The coating film preferably has barrier characteristics, that is, a moisture permeation rate of 0.01 $g/(m^2 \cdot 24$ h) or less determined at 25±0.5° C. and a relative humidity of 90±2% RH by a method in accordance with JIS K 7129-1992. The coating film preferably has high barrier characteristics, that is, an oxygen permeation rate of $10^3$ $cm^3/(m^2 \cdot 24$ h·atm) or less and a moisture permeation rate of $10^{-5}$ $g/(m^2 \cdot 24$ h) or less determined by a method in accordance with JIS K 7126-1987.

The barrier film may be composed of any material which prevents intrusion of substances, such as moisture and oxygen, which cause deterioration of luminescent elements. Silicon oxide, silicon dioxide, and silicon nitride can be used to form a barrier film. The barrier film more preferably has a laminate structure composed of an inorganic layer and an organic layer to improve toughness. The inorganic layer and the organic layer can be laminated in any order. Preferably, inorganic layers and organic layers are alternatingly laminated.

The barrier film can be formed by any process, such as vacuum evaporation, sputtering, reactive sputtering, molecular beam epitaxy, cluster ion beaming process, ion plating, plasma polymerization, atmospheric pressure plasma polymerization, plasma chemical vapor deposition (CVD), laser CVD, thermal CVD, and coating. Particularly preferred is atmospheric pressure plasma polymerization described in Japanese Patent Application Laid-Open No. 2004-68143.

Examples of the opaque support substrate include metal plates made of aluminum and stainless steel, films, opaque resin substrates, and ceramic substrates.

The organic EL element according to the present invention extracts light emission at room temperature at an out-coupling efficiency of preferably 1% or more, more preferably 5% or more.

The external quantum efficiency is defined by an expression: external quantum efficiency (%)=((the number of photons emitting light from organic EL element)/(the number of electrons flowing in organic EL element))×100.

The organic EL element may include a hue improving filter, such as a color filter, or a color converting filter containing a fluorescent substance to convert the color of a light emission from the organic EL element into a multicolored light emission. In an organic EL element including such a color converting filter, the light emission preferably has a λmax of 480 nm or less.

<<Process of Preparing Organic EL Element>>

An exemplary process of preparing an organic EL element will be described, the organic EL element being composed of an anode, a hole injecting layer, a hole transporting layer, a luminous layer, a hole blocking layer, an electron transporting layer, a cathode buffer layer (electron injecting layer), and a cathode.

A desired electrode or anode substance is formed into a thickness of 1 µm or less, preferably 10 to 200 nm to form a thin film on an appropriate substrate. An anode is prepared.

In the subsequent step, thin films containing organic compounds each are formed on the substrate with materials for an hole injecting layer, a hole transporting layer, a luminous layer, a hole blocking layer, an electron transporting layer, and a cathode buffer layer.

The respective thin films can be formed by a process, such as vacuum evaporation and a wet process.

Examples of the wet process include spin coating, casting, die coating, blade coating, roll coating, inkjetting, printing, spray coating, curtain coating, and LB processes. Preferred are die coating, roll coating, inkjetting, and spray coating, which are highly applicable to the roll-to-roll method to attain a precise thin film at high productivity. The individual layers of the element may be formed by different processes.

The materials for the organic EL element according to the present invention can be dissolved or dispersed in a solvent. Examples of the solvent include ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexylbenzene; aliphatic hydrocarbons, such as cyclohexane, decalin, and dodecane; and organic solvents, such as N,N-dimethylformamide (DMF) and dimethyl sulfoxide (DMSO).

The materials can be dispersed by ultrasonic, high shear force, or media dispersion.

After these layers are formed, a cathode material is formed into a thin film having a thickness in the range of 1 µm or less, preferably 50 to 200 nm to prepare a cathode. A desired organic EL element is thereby prepared.

The organic EL element can also be prepared in the reverse order, that is, through formation of a cathode, a cathode buffer layer, an electron transporting layer, a hole blocking layer, a luminous layer, a hole transporting layer, a hole injecting layer, and an anode in this order.

The organic EL element according to the present invention is preferably prepared in a single vacuum process from the formation of the hole injecting layer to that of the cathode. Alternatively, the workpiece may be extracted during the preparation procedure, and may be subjected to a different process. In this case, the workpiece is preferably treated under a dry inert gas atmosphere.

<<Sealing>>

Examples of a method of sealing used in the present invention include a method of bonding a sealing member to an electrode and a support substrate with an adhesive.

The sealing member can be disposed over a display region of the organic EL element. The sealing member may be in the form of a concave or flat plate. The sealing member has no limitation in transparency or electrical insulation.

Specific examples of the sealing member include glass plates, polymer plates and films, and metal plates and films. Examples of materials for the glass plates include soda lime glass, barium•strontium-containing glass, lead glass, aluminosilicate glass, borosilicate glass, barium borosilicate glass, and quartz.

Examples of the polymer plates include plates made of polycarbonates, acrylates, poly(ethylene terephthalate), poly (ether sulfide), and polysulfone.

Examples of materials for the metal plates include one or more metals selected from the group consisting of stainless steel, iron, copper, aluminum, magnesium, nickel, zinc, chromium, titanium, molybdenum, silicon, germanium, and tantalum and alloys thereof.

Preferably used in the present invention are polymer films and metal films, which can attain an organic EL element in the form of a thin film.

The polymer film preferably has an oxygen permeation rate of $1 \times 10^{-3}$ cm$^3$/(m$^2$·24 h·atm) or less determined by a method in accordance with JIS K 7126-1987 and a moisture permeation rate of $1 \times 10^{-3}$ g/(m$^2$·24 h) or less determined at 25±0.5° C. and a relative humidity of 90±2% RH by a method in accordance with JIS K 7129-1992.

The sealing member is processed by sandblasting or chemical etching to form a concave surface.

Specific examples of the adhesive include photo-curable and thermosetting adhesives of acrylic oligomers and methacrylic oligomers having a reactive vinyl group; and moisture-curable adhesives, such as 2-cyanoacrylic acid ester. Other examples thereof include epoxy thermosetting and chemosetting (binary systems) adhesive. Further examples thereof include hot-melt polyamide, polyester, and polyolefin adhesives. Further examples thereof include cationic UV-curable epoxy resin adhesives.

An adhesive curable at a temperature from room temperature to 80° C. to bond the organic EL element is preferred to prevent degradation of the organic EL element by a heat treatment. The adhesive may contain a desiccant dispersed therein. The adhesive may be applied onto the bonding area with a commercially available dispenser or by any printing process, such as screen printing.

Alternatively, a sealing film composed of inorganic layers and organic layers can be suitably disposed on the support substrate so as to cover the organic layer and the electrode remote from the support substrate. In this case, the material for the film can be any material which can prevent intrusion of substances, such as moisture and oxygen, which cause deterioration of luminescent elements. Usable examples of such substances include silicon oxide, silicon dioxide, and silicon nitride.

The sealing film preferably has a laminate structure composed of inorganic layers and organic materials to improve toughness. Examples of the processes of forming a sealing film include, but should not be limited to, vacuum evaporation, sputtering, reactive sputtering, molecular beam epitaxy, cluster ion beaming process, ion plating, plasma polymerization, atmospheric pressure plasma polymerization, plasma CVD, laser CVD, thermal CVD, and coating.

The gap between the sealing member and the display region of the organic EL element preferably contains an inactive gas such as nitrogen or argon or an inactive liquid, such as fluorohydrocarbon or silicone oil in gaseous and liquid phases. The gap can also be in vacuum. A moisture absorbing compound can also be encapsulated in the gap.

Examples of the moisture absorbing compound include metal oxides (such as sodium oxide, potassium oxide, calcium oxide, barium oxide, magnesium oxide, and aluminum oxide), sulfates (such as sodium sulfate, calcium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), and perchloric acids (such as barium perchlorate and magnesium perchlorate). As for sulfates, metal halides, and perchloric acids, anhydrides are suitably used.

<<Protective Film, Protective Plate>>

A protective film or plate may be disposed on or over the sealing film on the side opposite to the support substrate across the organic layer to enhance the mechanical strength of the organic EL element. In particular, an organic EL element encapsulated with the sealing film does not always have high mechanical strength, and such a protective film or plate is preferably disposed. The protective film or plate can be formed of the same glass plates, polymer plates and films, and metal plates and films as those used in the sealing of the organic EL element. Preferred are polymer films that can achieve thin lightweight organic EL elements.

<<Extraction of Light>>

Usually, the organic EL element emits light inside a luminous layer having a refractive index (refractive index: about 1.7 to 2.1) higher than that of the air, and extracts only about 15% to 20% of light beams generated in the luminous layer. Such low out-coupling efficiency is explained for the following reasons: The light components incident on the interface (interface between a transparent substrate and the air) at an angle θ equal to or greater than the critical angle are totally reflected, and cannot be extracted from the element. Moreover, light components totally reflected between the transparent electrode or the luminous layer and the transparent substrate are transmitted through the transparent electrode or the luminous layer, and finally escape to the sides of the element.

Examples of the measures to enhance the light out-coupling efficiency include formation of irregularities on the surface of a transparent substrate to prevent the total reflection of light at the interface between the transparent substrate and the air (U.S. Pat. No. 4,774,435); use of a light-convergent substrate in a luminescent element to enhance the out-coupling efficiency (Japanese Patent Application Laid-Open No. S63-314795); formation of a reflecting surface on side surfaces of a luminescent element (Japanese Patent Application Laid-Open No. H1-220394); disposition of a planarizing layer between a substrate and a luminous substance to form an antireflection film having a middle refractive index between the substrate and the luminous substance (Japanese Patent Application Laid-Open No. S62-172691); disposition of a planarizing layer between a substrate and a luminous substance, the planarizing layer having a refractive index lower than that of the substrate (Japanese Patent Application Laid-Open No. 2001-202827); and disposition of a diffraction grating between any two adjacent layers of a substrate, a transparent electrode layer, and a luminous layer (including the interface between the substrate and the outside of a luminescent element) (Japanese Patent Application Laid-Open No. H11-283751).

In the present invention, a combination of these measures can be applied to the organic EL element according to the present invention. Preferred is disposition of a planarizing layer between a substrate and a luminous substance, the planarizing layer having a refractive index lower than that of the substrate or disposition of a diffraction grating between any two adjacent layers of a substrate, a transparent electrode layer, and a luminous layer (including the interface between the substrate and the outside of a luminescent element).

The present invention can enhance the luminance or durability of the organic EL elements using these measures in combination.

If a medium having a low refractive index and having a thickness longer than the wavelength of light to be generated is disposed between a transparent electrode and a transparent substrate, the light is extracted from the transparent electrode at higher out-coupling efficiency as the medium has a lower refractive index.

Examples of materials for a low-refractive index layer include aerogel, porous silica, magnesium fluoride, and fluorine polymers. The transparent substrate generally has a refractive index of about 1.5 to 1.7. The low-refractive index layer preferably has a refractive index of 1.5 or less. The reflective index is more preferably 1.35 or less.

The thickness of the low-refractive index medium is desirably twice or more the wavelength of the light in the medium. If the thickness of the low-refractive index medium is approximately equal to the wavelength of the light, the advantageous effects of the low-refractive index layer are reduced because such a thickness allows evanescent electromagnetic waves to intrude into the substrate.

A diffraction grating disposed at the interface or any medium which totally reflects light can significantly enhance the out-coupling efficiency. The diffraction grating can orient light to a specific direction due to so-called Bragg diffraction, such as primary diffraction or secondary diffraction, rather than refraction of the light. Such features of the diffraction grating are utilized to extract the light beams from the organic EL element. Specifically, the diffraction grating is disposed at the interface between any two adjacent layers or inside any medium (inside the transparent substrate or the transparent electrode) to diffract the light beams which are generated in the luminous layer but cannot be extracted from the organic EL element due to total reflection at the interface.

The diffraction grating desirably has a two-dimensional periodic pattern on the refractive index. The light beams emitted from the luminous layer are radiated in random directions. A typical one-dimensional diffraction grating having a periodic refractive index distribution in one direction diffracts only the light beams traveling in one specific direction, and does not contribute to the light out-coupling efficiency of the light beams radiated in random directions.

A diffraction grating having a two-dimensional distribution of the refractive index, however, diffracts the light beams traveling in every direction to enhance the light out-coupling efficiency.

The diffraction grating may be disposed at the interface between any two adjacent layers or inside any medium (inside the transparent substrate or the transparent electrode). The diffraction grating is desirably disposed near the organic luminous layer emitting the light beams. The period of the diffraction grating is preferably about half to triple the wavelength of the light in the medium.

The diffraction grating is preferably composed of a two-dimensional repeated pattern consisting of, for example, squares, triangles, or honeycombs arrayed into a grating.

<<Light-Condensing Sheet>>

The organic EL element according to the present invention can include a microlens array structure disposed on the light-extracting surface of the substrate or include a light-condensing sheet to condense light in a specific direction, for example, to the front of the luminous surface of the element, thereby enhancing the luminance in the specific direction.

An exemplary microlens array is composed of quadrangular pyramids having a side of 30 μm and an apex angle of 90 degrees and two-dimensionally arranged on the light-extracting surface of the substrate. The side of the quadrangular pyramid is preferably 10 μm to 100 μm. A side less than 10 μm causes coloring due to diffraction. A side more than 100 μm increases the thickness of the microlens array.

Examples of usable light-condensing sheets include those used in LED backlights of liquid crystal displays. Specific examples of such sheets include a brightness enhancing film (BEF) made by Sumitomo 3M Limited.

An exemplary prism sheet may be composed of a base substrate provided with stripes consisting of pyramidal prisms having an apex angle of 90 degrees and a pitch of 50 μm. The prisms may have round apices, or may be disposed at randomized pitches. Alternatively, the prisms may have any other shape.

A light diffusion plate or film can be used in combination with the light-condensing sheet to control the emission angle of the light from the luminescent element. A light diffusion film LIGHT-UP made by Kimoto Co., Ltd. can be used, for example.

<<Applications>>

The organic EL element according to the present invention can be used in display devices, display panels, and a variety of light-emitting sources. Examples of the light-emitting sources include, but should not be limited to, illuminators (house lightings, car interior lightings), backlights for clocks and liquid crystal devices, advertising signs, traffic signals, and light sources for optical storage media, electrophotographic copiers, optical communication processors, and optical sensors. The organic EL element according to the present invention can be particularly effective in applications to backlights for liquid crystal displays and light sources for illuminators.

Patterning through a metal mask or by inkjet printing may be performed during preparation of the organic EL element according to the present invention. Only an electrode may be patterned, or both the electrode and the luminous layer may be patterned. All of the layers in the organic EL element may be patterned. The organic EL element can be prepared by any known process.

Figure 4:
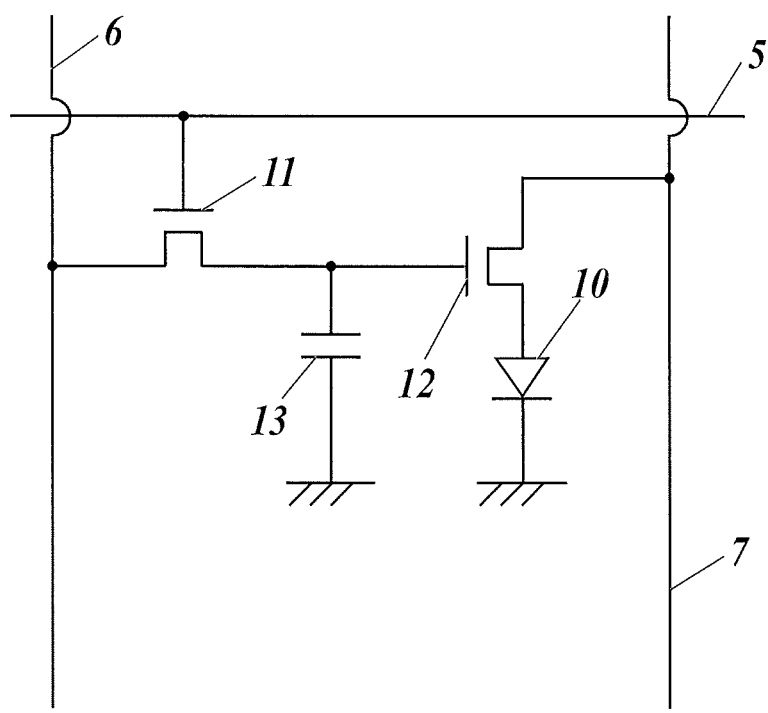
FIG. 4 is a diagram illustrating a circuit in a pixel.

The color of light emitted from the organic EL element according to the present invention or the compound according to the present invention is determined from the results of the measurements with a spectroradiometric luminance meter CS-1000 (made by Konica Minolta Sensing, Inc.) applied to the CIE chromaticity coordinates shown in FIG. 4.16 in page 108 of "Shinpen Shikisai Kagaku Handobukku (New Scientific Handbook of Color)" (edited by the Color Science Association of Japan, published by University of Tokyo Press, 1985).

In the organic EL element according to the present invention, the term "white" of a white element indicates that the chromaticity at 1000 cd/m$^2$ in the CIE 1931 color system is within the region defined by $x=0.33\pm0.07$ and $y=0.33\pm0.1$ in the measurement of the front luminance at a view angle of 2 degrees by the above method.

<<Display>>

The display according to the present invention will be described. The display according to the present invention includes the organic EL element according to the present invention. The display according to the present invention may be a monochromatic or multi-color display. A multi-color display will now be described.

In the multi-color display, the luminous layer can be formed over an underlying layer through a shadow mask by, for example, deposition, casting, spin coating, inkjetting, or printing.

Only the luminous layer can be patterned by any process, preferably, by deposition, inkjetting, spin coating, and printing processes.

The configuration of the organic EL element included in the display can be selected from the exemplary configurations (described above) of the organic EL element when necessary.

The method of preparing an organic EL element is described as one aspect of the organic EL element according to the present invention.

Light is emitted under a DC voltage of about 2 V to 40 V applied between an anode (positive polarity) and a cathode (negative polarity) in the multi-color display. If a voltage with reverse polarity is applied between the electrodes, no current flows and thus no light emission occurs. Light is emitted under an AC voltage only while the anode is being positive and the cathode is being negative. The AC voltage to be applied may have any waveform.

The multi-color display can be used in display devices, display panels, and a variety of light-emitting sources. Display devices and display panels can display multi-color images through three types of organic EL elements emitting blue light, red light, and green light, respectively.

Examples of the display devices and the display panels include television sets, personal computers, mobile apparatuses, audiovisual apparatuses, display panels for text broadcasting receivers, and car-mount displays. In particular, the multi-color display can be used for reproducing still pictures and moving pictures. A display for reproducing moving pictures can be driven in a simple matrix (passive matrix) mode or an active matrix mode.

Examples of the light-emitting sources include, but should not be limited to, house lightings, car interior lightings, backlights for clocks and liquid crystal devices, advertising signs, traffic signals, and light sources for optical storage media, electrophotographic copiers, optical communication processors, and optical sensors.

An exemplary display including the organic EL element according to the present invention will now be described based on the drawings.

Figure 2:
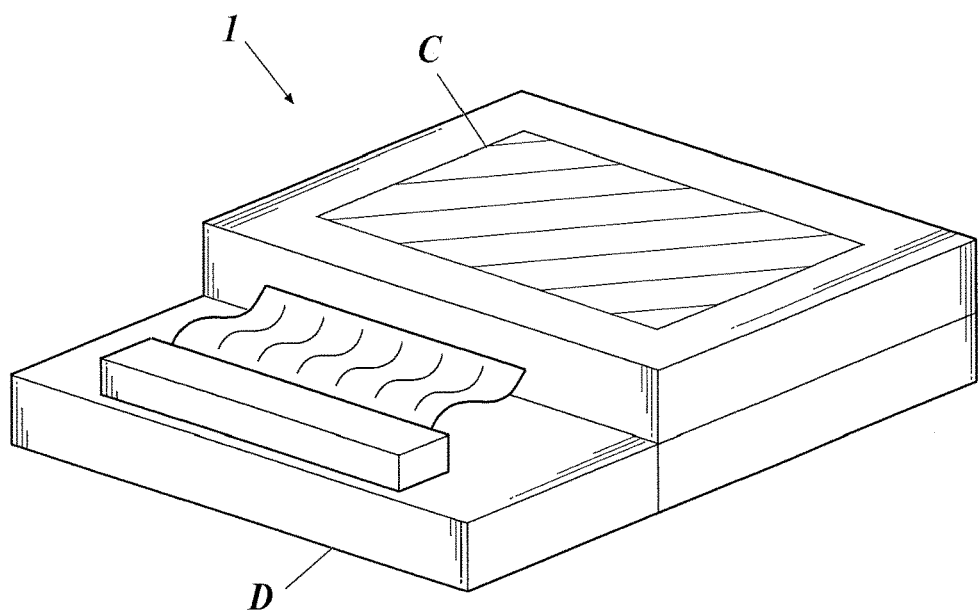
FIG. 2 is a schematic view illustrating an exemplary display including an organic EL element.

FIG. 2 is a schematic view illustrating an exemplary display including an organic EL element. The display in the drawing is mounted on a mobile phone, for example, to display image information according to the light emission from the organic EL element.

A display 1 includes a display unit C having multiple pixels, and a control unit D scanning an image on the display unit C based on image information.

The control unit D is electrically connected to the display unit C. The control unit D transmits scanning signals and image data signals to the pixels based on external image information. In response to the scanning signals, the pixels on the corresponding scanning lines sequentially emit light according to the image data signals for image scanning operations, and the image information is displayed on the display unit C.

Figure 3:
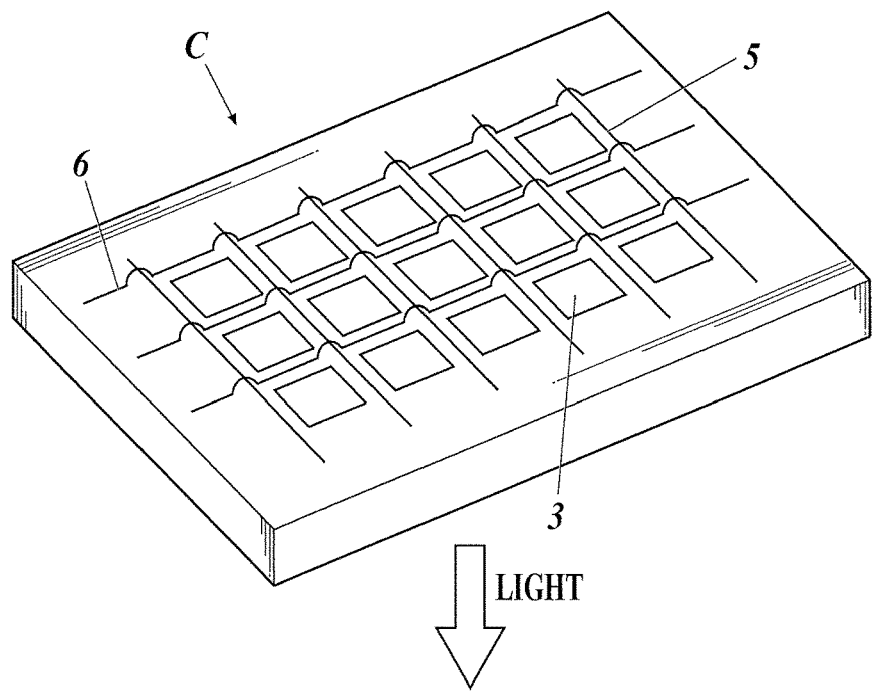
FIG. 3 is a schematic view illustrating a display unit C in FIG. 2.

FIG. 3 is a schematic view illustrating the display unit C.

The display unit C includes a substrate, a line unit including multiple scanning lines 5 and data lines 6, and pixels 3. The main components of the display unit C will now be described.

In FIG. 3, the light emitted from the pixels 3 is extracted in the direction indicated by the blank arrow (downward in the drawing).

The scanning lines 5 and the data lines 6 in the line unit are composed of a conductive material. The scanning lines 5 intersect orthogonal to the data lines 6 in the form of a grating. The intersections are connected to the pixels 3 (details are not illustrated).

Each of the pixels 3 receives a scanning signal from the corresponding scanning line 5, and then receives an image data signal from the corresponding data line 6. The pixels 3 emit light according to the received image data.

The pixels emitting red light, those emitting green light, and those emitting blue light are appropriately disposed on the substrate to achieve full-color display of images.

The process of emitting light from pixels will now be described. FIG. 4 is a diagram illustrating a circuit in a pixel.

The pixel includes an organic EL element 10, a switching transistor 11, a driving transistor 12, and a capacitor 13. Red, green, and blue organic EL elements 10 can be disposed in the pixels on the substrate to achieve full-color display of images.

In FIG. 4, an image data signal is input from the control unit D through the data line 6 to the drain of the switching transistor 11. A scanning signal is input from the control unit D through the scanning line 5 to the gate of the switching transistor 11. The switching transistor 11 is then turned on to transmit the image data signal in the drain to the capacitor 13 and the gate of the driving transistor 12.

In response to the transmission of the image data signal, the capacitor 13 is charged according to the potential of the image data signal and the driving transistor 12 is turned on. The drain of the driving transistor 12 is connected to a power supply line 7, and the source thereof is connected to the electrode of the organic EL element 10. The current is fed from the power supply line 7 to the organic EL element 10 according to the potential of the image data signal input to the gate of the driving transistor 12.

The scanning signal is transmitted to the next scanning line 5 as a result of sequential scanning by the control unit D, and the switching transistor 11 is then turned off. The capacitor 13 keeps the charged potential of the image data signal even after the switching transistor 11 is turned off. The driving transistor 12 is kept on to continuously emit light from the organic EL element 10 until the input of the next scanning signal. The next scanning signal is input by sequential scanning. The driving transistor 12 is then driven according to the potential of the next image data signal in synchronization with the input of the next scanning signal, so that the organic EL element 10 emits light.

In short, the pixels each include the organic EL element 10, and active elements, i.e., the switching transistor 11 and the driving transistor 12, which control the light emission of the organic EL element 10 in each pixel 3. Such a process of light emission is called an active matrix mode.

The light emission of the organic EL element 10 may have gradations derived from a multilevel image data signal having a plurality of gradation potentials, or may have a predetermined amount of light emission switched on/off by a binary image data signal. The capacitor 13 may keep the charged potential until the input of the next scanning signal, or may discharge immediately before the input of the next scanning signal.

The organic EL element according to the present invention can be driven not only in the active matrix mode but also in a passive matrix mode to emit light according to the data signal only while the scanning signal is being input.

Figure 5:
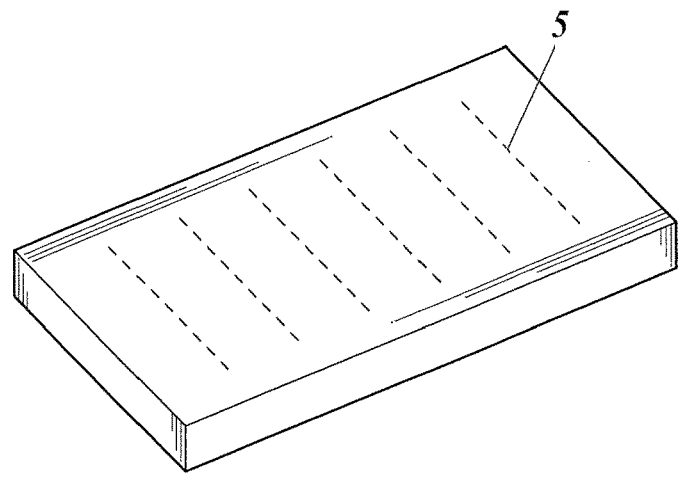
FIG. 5 is a schematic view illustrating a passive matrix full-color display.
Figure 5:
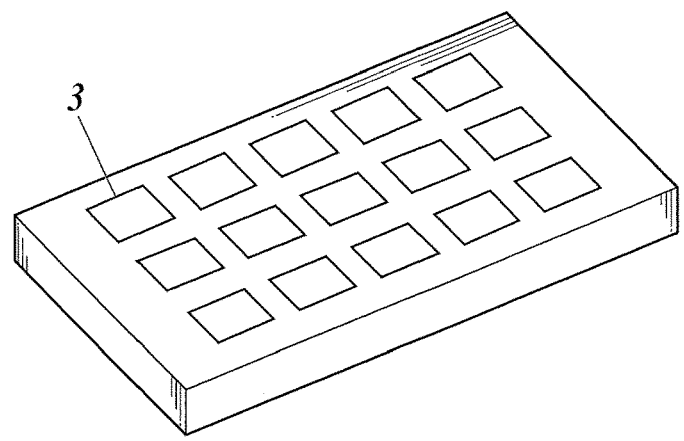
Figure 5:
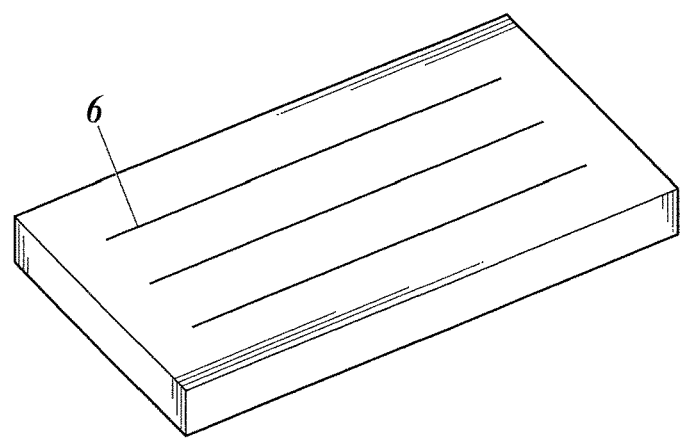

FIG. 5 is a schematic view illustrating a display in a passive matrix mode. In FIG. 5, multiple scanning lines 5, pixels 3, and image data lines 6 are disposed in sequence. The scanning lines 5 and the image data lines 6 are disposed in in a grid pattern.

A scanning signal is input from the scanning line 5 as a result of sequential scanning, and the pixel 3 connected to the scanning line 5 then emits light according to an image data signal.

An organic EL element in the passive matrix mode has no active element in the pixel 3 and thus can be produced at low cost.

<<Illuminator>>

The illuminator according to the present invention will now be described. The illuminator according to the present invention includes the organic EL element. The organic EL element according to the present invention may have a resonator structure. Such an organic EL element having a resonator structure can be used in applications to light sources for optical storage media, electrophotographic copiers, optical communication processors, and optical sensors, but should not be limited to these applications. The organic electroluminescent element according to the present invention causing laser oscillation can also be used in these applications.

The organic EL element according to the present invention can also be used as a lamp for illumination and a light source for exposure, or can also be used in image projectors or displays for directly displaying still pictures or moving pictures.

The organic EL element included in a display for reproducing moving pictures can be driven in the simple matrix (passive matrix) mode or an active matrix mode. Two or more organic EL elements according to the present invention emitting light of different colors can achieve a full-color display.

The organic EL material according to the present invention can be used in an illuminator to emit substantially white light. White light is attained through mixing of different colors of light beams emitted from two or more luminous materials at the same time. The light beams of such a color combination may have three maximum wavelengths corresponding to three primary colors, red, green, and blue, or may have two maximum wavelengths corresponding to complementary colors, such as blue and yellow, or blue green and orange.

The combination of luminous materials emitting light beams of different colors can be selected from combinations of two or more phosphorescent or fluorescent materials and combinations of fluorescent or phosphorescent luminous materials with dyes emitting excitation light of the light emitted from the luminous materials. The white organic EL element according to the present invention can be achieved by a combination of luminous dopants.

Such white organic electroluminescent elements can be prepared by the following simple process: These luminous materials are separately applied through respective masks in the formation of a luminous layer, a hole transporting layer, or an electron transporting layer. Other common layers, such as electrode layers, can be disposed over the entire underlying layers by a process, such as deposition, casting, spin coating, inkjetting, or printing, without patterning through a mask, at high productivity.

An organic EL element itself produced by this process emits white light, unlike white organic EL devices including arrays of different color luminescent elements disposed in parallel.

Any luminous material can be used in the luminous layer. For example, white light in a backlight for a liquid crystal display element can be produced by any combination selected from the metal complex according to the present invention and known luminous materials so as to match wavelength ranges with desired color filter (CF) properties.

<<An Embodiment of Illuminator According to the Present Invention>>

An embodiment of the illuminator according to the present invention including the organic EL element according to the present invention will now be described.

The organic EL element according to the present invention is disposed on a glass sealing substrate having a thickness of 300 μm. An epoxy photo-curable adhesive (Laxtrack LC0629B made by TOAGOSEI CO., LTD.) is applied around the organic EL element. A glass case is disposed over the cathode to cover the non-luminous surface of the element, and is bonded to the transparent sealing substrate. The glass sealing substrate is irradiated with UV light to cure the adhesive. The organic EL element is thereby sealed to prepare an illuminator illustrated in FIGS. 6 and 7.

Figure 6:
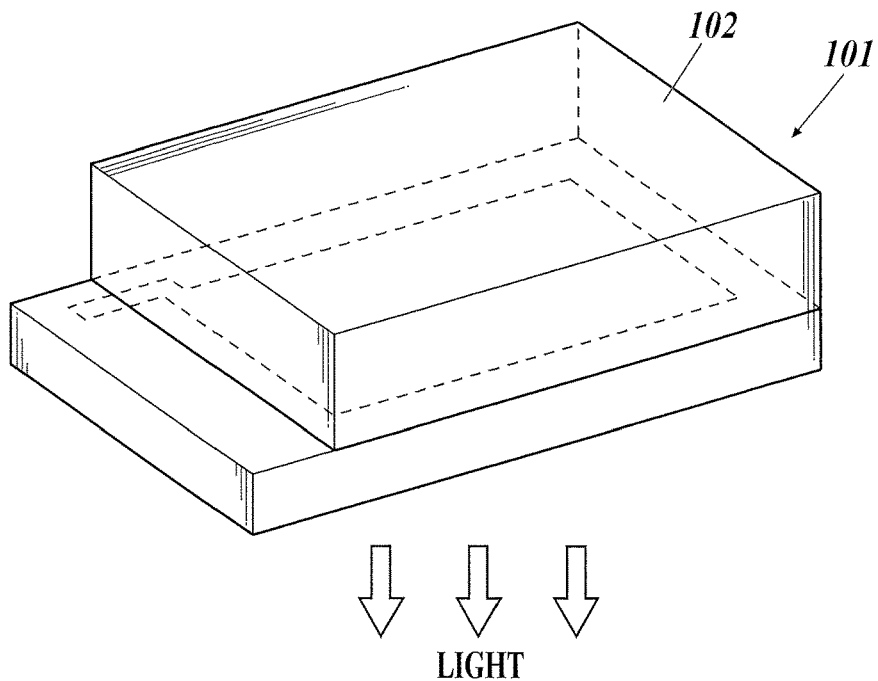
FIG. 6 is a schematic view illustrating an illuminator.

FIG. 6 is a schematic view illustrating an illuminator. The organic EL element according to the present invention 101 is covered with a glass cover 102. Sealing with the glass cover is performed under a nitrogen atmosphere (under an atmosphere of high purity nitrogen gas (purity: 99.999% or more)) in a glovebox so as not to contact the organic EL element 101 with air.

Figure 7:
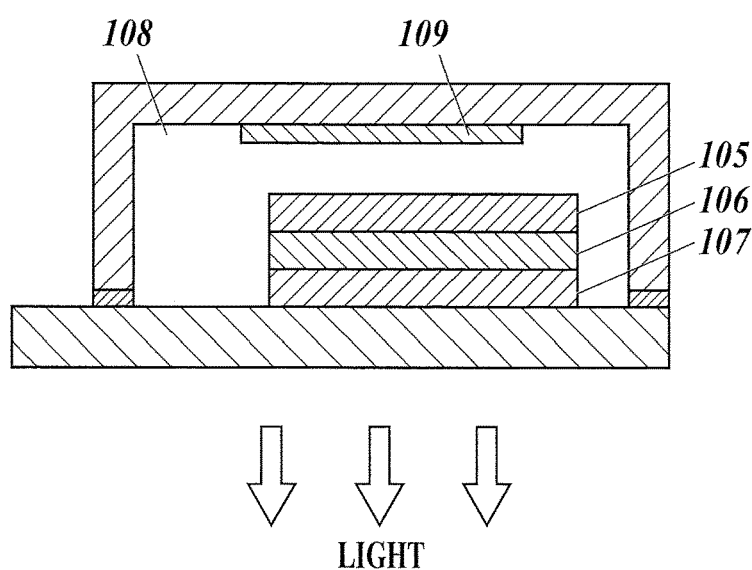
FIG. 7 is a schematic view illustrating an illuminator.

FIG. 7 is a sectional view illustrating an illuminator. FIG. 7 illustrates a cathode 105, an organic EL layer 106, and a glass substrate 107 with a transparent electrode. The interior of the glass cover 102 is filled with nitrogen gas 108, and contains a moisture getter 109.

EXAMPLE

The present invention will now be described in more detail by way of non-limiting Examples. In Examples, "parts" and "%" indicate "parts by mass" and "mass %", respectively, unless otherwise specified.

<<Preparation of Exemplified Compound 71>>
(Preparation of Intermediate Product 2)

Iridium chloride (3.53 g) and Intermediate product 1 (6.56 g) were refluxed under heat in a mixed solvent of 1-propanol (65 ml) and water (13 ml) under a nitrogen atmosphere for three hours. The reaction solution was cooled to room temperature. The precipitated crystal was collected by filtration, was cleaned with methanol, and was dried to prepare Intermediate product 2 (6.44 g, yield: 90%).

(Preparation of Exemplified Compound 71)

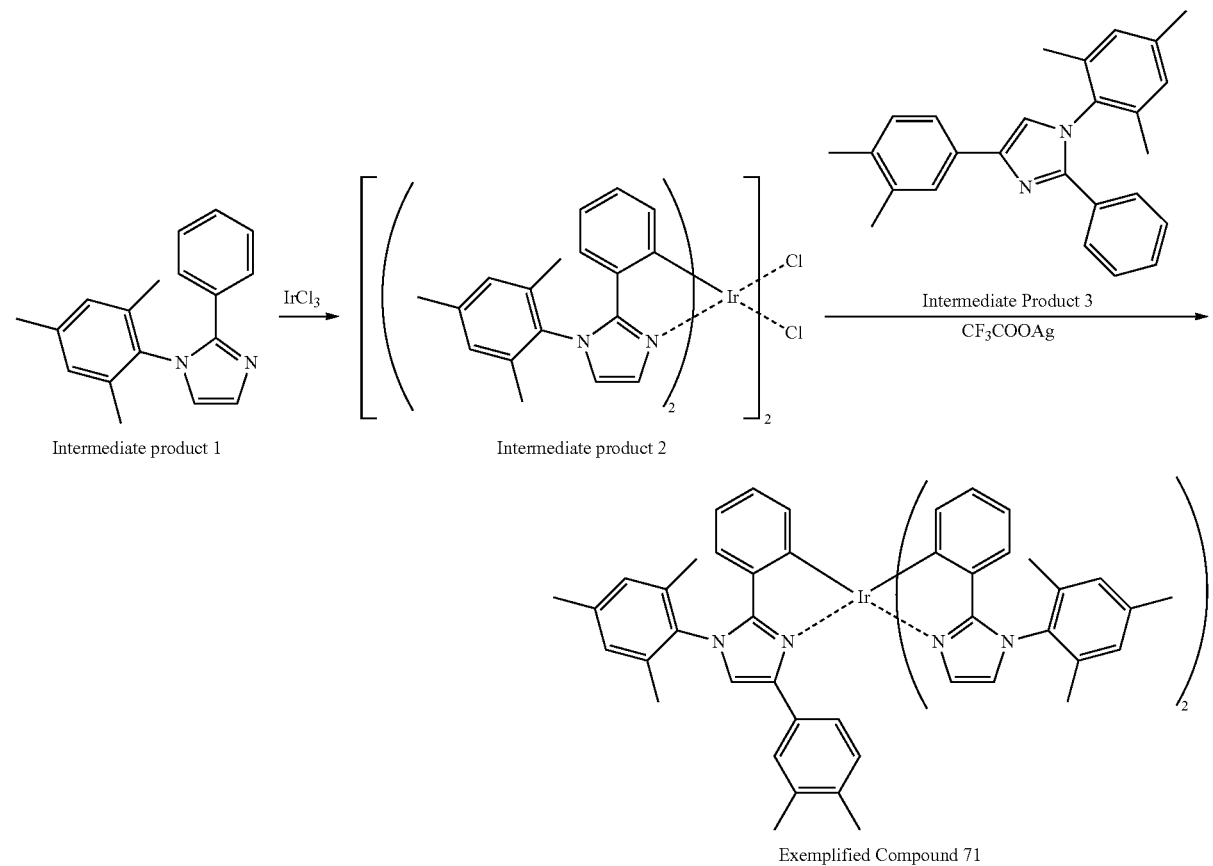

Exemplified Compound 71

Intermediate product 1 (1.43 g), silver trifluoroacetate (0.6 g), and Intermediate product 3 (0.9 g) were stirred under heat in phenyl acetate (14 ml) at 140° C. for five hours. The reaction solution was cooled to room temperature. The insoluble substances were separated, and the filtrate was purified by silica gel column chromatography to prepare Exemplified compound 71 (1.09 g, yield: 50%).

Exemplified compound 71 prepared through this operation was analyzed with a high-performance liquid chromatograph equipped with an ODS column filled with a silica gel having a surface modified with octadecyl groups as a solid phase. Exemplified compound 71 was a mixture of two components.

Figure 8:
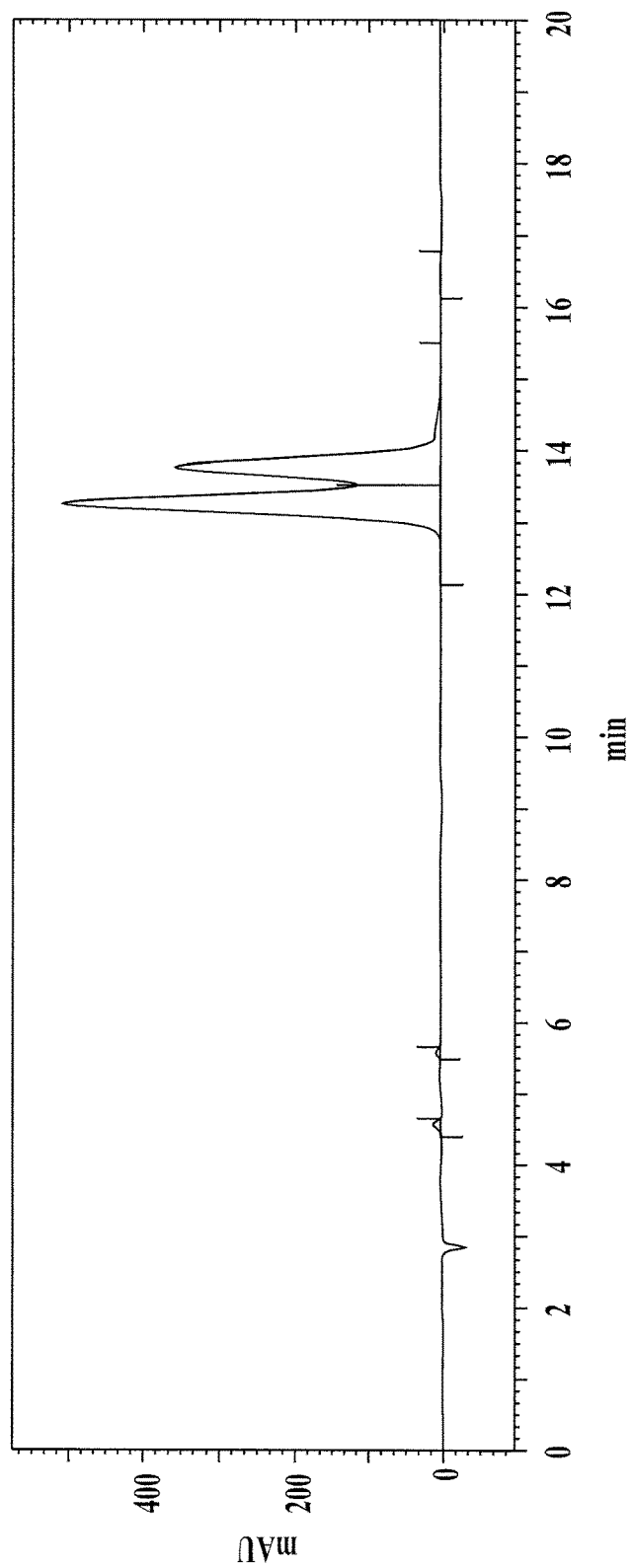
FIG. 8 is a chart illustrating a result of measurement by high-performance liquid chromatography.

FIG. 8 is a chart illustrating the results of high-performance liquid chromatography. FIG. 8 is a chart of high-performance liquid chromatography of Exemplified compound 71. The peaks corresponding to the diastereoisomer components of Exemplified compound 71 are found at the retention times of 13.2 min (area rate: 57.3%) and 13.7 min (area rate: 42.4%), respectively.

The separated components through the ODS column are diastereoisomers rather than enantiomers because the ODS column is achiral. In detail, among four isomeric complexes consisting of enantiomers and diastereoisomers in a hexa-coordinated octahedral Ir complex having two chiral centers of optical isomers, i.e., one chiral center of the Λ and Δ isomers of the Ir complex and the other chiral center for atropisomers or the bond axis between the 3,4-dimethylphenyl group and the imidazole ring after formation of the complex, diastereoisomers, i.e., 0Λ-1R and 0Δ-1R, were respectively separated into a mixture of 0Λ-1R and 0Δ-1S and another mixture of 0Δ-1R and 0Λ-1S. The components were separated with a HPLC for separation to yield Exemplified compounds 71-A (0.35 g) and 71-B (0.29 g), which were mixed enantiomer components prepared through diastereoisomer separation of Exemplified compound 71. Although the conformations of these isomers were not determined, the nuclear magnetic resonance spectra and mass spectra of these isomers demonstrated that these isomers were Exemplified compound 71.

[Example 1] (Deposition System)

<<Preparation of Organic EL Element 1-1>>

Indium tin oxide (ITO) was applied onto a glass substrate with dimensions of 100 mm×100 mm×1.1 mm (NA45 made by AvanStrate Inc.) to form a film having a thickness of 100 nm. This film was patterned into an anode. This transparent support substrate provided with the ITO transparent electrode was ultrasonically cleaned with isopropyl alcohol, was dried with dry nitrogen gas, and was cleaned with UV ozone for five minutes.

A diluted solution of 70% poly(3,4-ethylenedioxythiophene)-polystyrene sulfonate (PEDOT/PSS, made by Bayer AG, Baytron P Al 4083) in pure water was applied onto the transparent support substrate by spin coating at 3000 rpm for 30 seconds to form a thin film. The thin film was dried at 200° C. for one hour to form a hole injecting layer having a thickness of 20 nm.

The transparent support substrate was fixed to a substrate holder in a commercially available vacuum deposition apparatus. After α-4,4'-bis[N-(1-naphthyl)-N-phenylamino]biphenyl (NPD) (200 mg), 4,4'-N,N'-dicarbazolebiphenyl (CBP) (200 mg), Exemplified compound 71 (200 mg), and 2,9-dimethyl-4,7-diphenyl-1,10-phenanthroline (BCP) (200 mg) were separately placed in molybdenum resistive heating boats, these molybdenum resistive heating boats were placed in the vacuum deposition apparatus.

After the vacuum vessel was evacuated to 4×10$^{-4}$ Pa, the heating boat containing α-NPD was electrically heated to deposit a-NPD onto the hole injecting layer at a deposition rate of 0.1 nm/sec. A hole transporting layer having a thickness of 30 nm was formed.

The heating boat containing CBP and the heating boat containing Exemplified compound 71 were electrically heated to co-deposit CBP and Exemplified compound 71 on the hole transporting layer at deposition rates of 0.1 nm/sec and 0.010 nm/sec, respectively, to form a luminous layer having a thickness of 40 nm.

The heating boat containing BCP was further electrically heated at a deposition rate of 0.1 nm/sec to deposit BCP on the luminous layer to form an electron transporting layer having a thickness of 30 nm.

Lithium fluoride was then deposited to form a cathode buffer layer having a thickness of 0.5 nm, and aluminum was deposited to form a cathode having a thickness of 110 nm. Organic EL element 1-1 was thereby prepared.

<<Preparation of Organic EL Elements 1-2 and 1-3>>

Organic EL elements 1-2 and 1-3 were prepared as in Organic EL element 1-1 except that Exemplified compound 71 was replaced with Exemplified compound 71-A or 71-B, which was a diastereoisomer component of Exemplified compound 71 separated in Synthetic Example.

<<Evaluation of Organic EL Elements 1-1 to 1-3>>

In evaluation of the organic EL elements, the non-luminous surface of each organic EL element was covered with a glass cover. An epoxy photo-curable adhesive (Laxtrack LC0629B made by TOAGOSEI CO., LTD.) was applied onto the glass substrate around the organic EL element. The glass cover was disposed over the cathode, and was bonded to the transparent support substrate. The glass substrate excluding the organic EL element was irradiated with UV light to cure the adhesive. The organic EL element was thereby sealed to prepare an illuminator illustrated in FIGS. 6 and 7.

The samples were evaluated on the following items. The results of evaluation are shown in Table 1.

(1) External Quantum Efficiency (Also Simply Referred to as Efficiency)

The organic EL elements were driven at room temperature (about 23 to 25° C.) and a constant current of 2.5 mA/cm$^2$. The luminance (L) [cd/m$^2$] of the light emitted immediately after the lighting was measured, and external quantum efficiency (η) was calculated.

The luminance was measured with a luminance meter CS-1000 (made by Konica Minolta Sensing, Inc.). The external quantum efficiency was expressed as a relative value to the external quantum efficiency of Organic EL element 1-1 (100).

(2) Rate of Change in Resistance Before and after Activation of Organic EL Element In each of the organic EL elements, the resistance at a bias voltage of 1 V of the luminous layer was measured with an impedance analyzer Model 1260 and a dielectric interface Model 1296 (made by Solartron Analytical Co.) in accordance with the procedure described in "Usumakuno Hyoka Handobukku (Handbook of Thin Film Characterization Technology)," published by Technosystem Co., Ltd., pp. 423-425.

The resistances of the luminous layer before and after activation of each organic EL element at room temperature (about 23° C. to 25° C.) and a constant current of 2.5 mA/cm² for 1000 hours were measured. From the results, the rate of change in resistance was calculated by the following expression. Table 1 shows relative values to the rate, 100, of change in resistance of Organic EL element 1-1.

Rate of change in resistance before and after activation of organic EL element=|(resistance after activation)/(resistance before activation)−1|×100

A value closer to 0 indicates a smaller rate of change in resistance before and after activation of the element.

TABLE 1

| Organic EL Element No. | Dopant | Host Compound | External Quantum Efficiency (Relative Value) | Rate of Change in Resistance (Relative Value) | Theoretical Number of Isomers | Note |
|---|---|---|---|---|---|---|
| 1-1 | Exemplified Compound 71 | CBP | 100 | 100 | 4 | Invention |
| 1-2 | Exemplified Compound 71-A | CBP | 101 | 117 | 2 | Comparison |
| 1-3 | Exemplified Compound 71-B | CBP | 102 | 110 | 2 | Comparison |

Table 1 evidently shows that the external quantum efficiency of the complex according to the present invention was substantially the same between Exemplified compounds 71-A and 71-B each containing two isomers separated through diastereoisomer separation and Exemplified compound 71 containing four isomers (mixed diastereoisomer components). In consequence, the diastereoisomers of the complex according to the present invention had equal luminous ability.

Table 1 shows that the rates of change in resistance of the luminous layers composed of a single diastereoisomer component in Organic EL elements 1-2 and 1-3 were larger than that of the luminous layer composed of the mixed diastereoisomer components in Organic EL element 1-1. The results demonstrate that the mixed diastereoisomer components enhanced the stability of the complex in the form of a film.

The same operation was performed on other Exemplified compounds to separate diastereoisomer components, and it was verified that these separated components were the target compounds. Organic EL elements were prepared as in Organic EL elements 1-1 to 1-3 in Example 1 with these separated diastereoisomers and the mixed diastereoisomers, and the performances thereof were evaluated. Similar results of evaluation were obtained in the separated diastereoisomers and the mixed diastereoisomers.

[Example 2] (Deposition System)

<<Preparation of Organic EL Element 2-1>>

Indium tin oxide (ITO) was applied onto a glass substrate with dimensions of 100 mm×100 mm×1.1 mm (NA45 made by AvanStrate Inc.) to form a film having a thickness of 100 nm. This film was patterned into an anode. This transparent support substrate provided with the ITO transparent electrode was ultrasonically cleaned with isopropyl alcohol, was dried with dry nitrogen gas, and was cleaned with UV ozone for five minutes.

A diluted solution of 70% poly(3,4-ethylenedioxythiophene)-polystyrene sulfonate (PEDOT/PSS, made by Bayer AGC Baytron P Al 4083) in pure water was applied onto the transparent support substrate by spin coating at 3000 rpm for 30 seconds to form a thin film. The thin film was dried at 200° C. for one hour to form a hole injecting layer having a thickness of 20 nm.

The transparent support substrate was fixed to a substrate holder in a commercially available vacuum deposition apparatus. After α-NPD (200 mg), OC-30 (200 mg), Dopant D-26 (200 mg), and BCP (200 mg) were separately placed in molybdenum resistive heating boats, these molybdenum resistive heating boats were placed in the vacuum deposition apparatus.

After a vacuum vessel was evacuated to 4×10⁻⁴ Pa, the heating boat containing α-NPD was electrically heated to deposit α-NPD onto the hole injecting layer at a deposition rate of 0.1 nm/sec. A hole transporting layer having a thickness of 30 nm was formed.

The heating boat containing OC-30 and the heating boat containing Dopant D-26 as a comparative compound were electrically heated to co-deposit these compounds on the hole transporting layer at deposition rates of 0.1 nm/sec and 0.010 nm/sec, respectively, to form a luminous layer having a thickness of 40 nm.

The heating boat containing BCP was further electrically heated at a deposition rate of 0.1 nm/sec to deposit BCP on the luminous layer to form an electron transporting layer having a thickness of 30 nm.

Lithium fluoride was then deposited to form a cathode buffer layer having a thickness of 0.5 nm, and aluminum was deposited to form a cathode having a thickness of 110 nm. Organic EL element 2-1 was thereby prepared.

<<Preparation of Organic EL Elements 2-2 to 2-75>>

Organic EL elements 2-2 to 2-75 were prepared as in Organic EL element 1-1 except that D-26 or OC-30 was replaced with the compounds listed in Table 1.

The structure of the comparative compound is shown below:

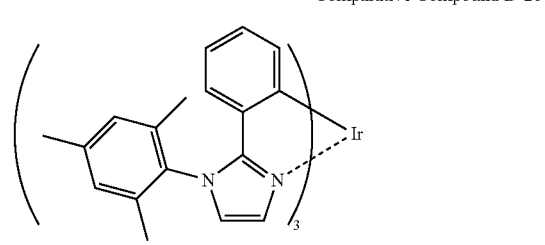

Comparative Compound D-26

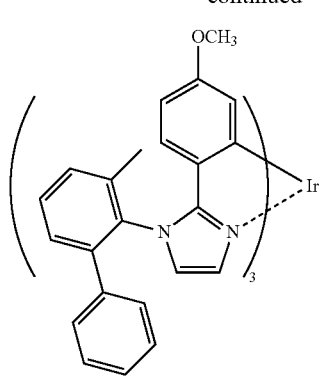

Comparative Compound 1

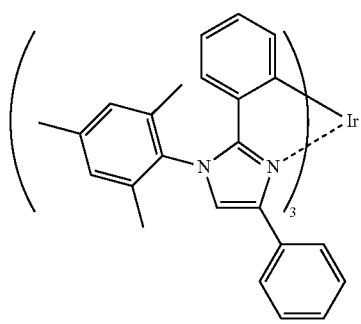

Comparative Compound 2

<<Evaluation of Organic EL Elements 2-1 to 2-75>>

In evaluation of the organic EL elements, the non-luminous surface of each organic EL element was covered with a glass cover. An epoxy photo-curable adhesive (Laxtrack LC0629B made by TOAGOSEI CO., LTD.) was applied onto the glass substrate around the organic EL element. The glass cover was disposed over the cathode, and was bonded to the transparent support substrate. The glass cover was disposed over the cathode, and was bonded to the transparent support substrate. The glass substrate excluding the organic EL element was irradiated with UV light to cure the adhesive. The organic EL element was thereby sealed to prepare an illuminator illustrated in FIGS. 6 and 7. The resistance of the luminous layer was measured with an impedance spectroscope, and the rate of change in half width of the light emission spectrum of the organic EL element was measured.

(1) Rate of Change in Resistance Before and after Activation of Organic EL Element In each of the organic EL elements, the resistance at a bias voltage of 1 V of the luminous layer was measured with an impedance analyzer Model 1260 and a dielectric interface Model 1296 (made by Solartron Analytical Co.) in accordance with the procedure described in "Usumakuno Hyokagijutsu Handobukku (Handbook of Thin Film Characterization Technology)," published by Technosystem Co., Ltd., pp. 423-425.

The resistances of the luminous layer were measured before and after activation of each organic EL element at room temperature (about 23° C. to 25° C.) and a constant current of 2.5 mA/cm² for 1000 hours. The rate of change in resistance was calculated from these results by the following expression. Table 1 shows relative values to the rate, 100, of change in resistance of Organic EL element 2-1.

Rate of change in resistance before and after activation of organic EL element=|(resistance after activation)/(resistance before activation)−1|×100

A value closer to 0 indicates a smaller rate of change in resistance before and after activation of the element.

(2) Rate of Change in Half Width of Light Emission Spectrum Before and after Activation of Organic EL Element The light emission spectra were measured before and after activation of the organic EL element at room temperature (about 23° C. to 25° C.) at a constant current of 2.5 mA/cm² for 1000 hours with a luminance meter CS-1000 (made by KONICA MINOLTA OPTICS, INC.) to calculate the rate of change in half width of the peak wavelength from the following expression. Tables 2 to 4 show relative values to the rate, 100, of change in half width of Organic EL element 2-1.

Rate of change in half width of light emission spectrum before and after activation of organic EL element=|(half width after activation)/(half width before activation)−1|×100

A value closer to 0 indicates a smaller rate of change in half width of light emission spectrum before and after activation of the organic EL element.

TABLE 2

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 2-1 | D-26 | OC-30 | 100 | 100 | 2 | Comparison |
| 2-2 | D-26 | OC-2 | 110 | 117 | 2 | Comparison |
| 2-3 | D-26 | OC-33 | 91 | 102 | 2 | Comparison |
| 2-4 | Comparative Compound 1 | OC-30 | 101 | 104 | 16 | Comparison |
| 2-5 | Comparative Compound 1 | OC-2 | 121 | 109 | 16 | Comparison |
| 2-6 | Comparative Compound 1 | OC-33 | 102 | 99 | 16 | Comparison |
| 2-7 | Comparative Compound 2 | OC-30 | 98 | 91 | 2 | Comparison |
| 2-8 | Comparative Compound 2 | OC-2 | 119 | 116 | 2 | Comparison |
| 2-9 | Comparative Compound 2 | OC-33 | 90 | 102 | 2 | Comparison |
| 2-10 | Exemplified Compound 1 | OC-30 | 50 | 47 | 16 | Invention |
| 2-11 | Exemplified Compound 2 | OC-30 | 42 | 49 | 16 | Invention |
| 2-12 | Exemplified Compound 3 | OC-30 | 51 | 44 | 16 | Invention |
| 2-13 | Exemplified Compound 4 | OC-30 | 49 | 49 | 16 | Invention |
| 2-14 | Exemplified Compound 7 | OC-30 | 47 | 41 | 16 | Invention |
| 2-15 | Exemplified Compound 7 | OC-2 | 56 | 57 | 16 | Invention |

TABLE 2-continued

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 2-16 | Exemplified Compound 7 | OC-33 | 49 | 46 | 16 | Invention |
| 2-17 | Exemplified Compound 9 | OC-30 | 50 | 43 | 16 | Invention |
| 2-18 | Exemplified Compound 11 | OC-30 | 50 | 45 | 16 | Invention |
| 2-19 | Exemplified Compound 12 | OC-30 | 49 | 48 | 16 | Invention |
| 2-20 | Exemplified Compound 12 | OC-2 | 54 | 55 | 16 | Invention |
| 2-21 | Exemplified Compound 13 | OC-30 | 59 | 57 | 8 | Invention |
| 2-22 | Exemplified Compound 16 | OC-30 | 49 | 45 | 16 | Invention |
| 2-23 | Exemplified Compound 18 | OC-30 | 51 | 35 | 16 | Invention |
| 2-24 | Exemplified Compound 20 | OC-30 | 42 | 36 | 16 | Invention |
| 2-25 | Exemplified Compound 22 | OC-30 | 44 | 38 | 16 | Invention |
| 2-26 | Exemplified Compound 24 | OC-30 | 45 | 39 | 16 | Invention |
| 2-27 | Exemplified Compound 26 | OC-30 | 41 | 40 | 16 | Invention |
| 2-28 | Exemplified Compound 27 | OC-30 | 40 | 38 | 16 | Invention |
| 2-29 | Exemplified Compound 30 | OC-30 | 39 | 42 | 16 | Invention |
| 2-30 | Exemplified Compound 31 | OC-30 | 43 | 40 | 16 | Invention |

TABLE 3

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 2-31 | Exemplified Compound 31 | OC-2 | 50 | 46 | 16 | Invention |
| 2-32 | Exemplified Compound 33 | OC-30 | 40 | 40 | 16 | Invention |
| 2-33 | Exemplified Compound 34 | OC-30 | 55 | 57 | 8 | Invention |
| 2-34 | Exemplified Compound 35 | OC-30 | 41 | 38 | 16 | Invention |
| 2-35 | Exemplified Compound 38 | OC-30 | 39 | 39 | 16 | Invention |
| 2-36 | Exemplified Compound 40 | OC-30 | 37 | 41 | 16 | Invention |
| 2-37 | Exemplified Compound 41 | OC-30 | 39 | 36 | 16 | Invention |
| 2-38 | Exemplified Compound 43 | OC-30 | 40 | 38 | 16 | Invention |
| 2-39 | Exemplified Compound 44 | OC-30 | 32 | 31 | 16 | Invention |
| 2-40 | Exemplified Compound 44 | OC-2 | 45 | 40 | 16 | Invention |
| 2-41 | Exemplified Compound 44 | OC-33 | 33 | 32 | 16 | Invention |
| 2-42 | Exemplified Compound 45 | OC-30 | 31 | 28 | 16 | Invention |
| 2-43 | Exemplified Compound 46 | OC-30 | 28 | 29 | 16 | Invention |
| 2-44 | Exemplified Compound 47 | OC-30 | 30 | 31 | 16 | Invention |
| 2-45 | Exemplified Compound 48 | OC-30 | 28 | 30 | 16 | Invention |
| 2-46 | Exemplified Compound 48 | OC-2 | 45 | 42 | 16 | Invention |
| 2-47 | Exemplified Compound 48 | OC-33 | 30 | 34 | 16 | Invention |
| 2-48 | Exemplified Compound 49 | OC-30 | 27 | 31 | 16 | Invention |
| 2-49 | Exemplified Compound 51 | OC-30 | 31 | 27 | 16 | Invention |
| 2-50 | Exemplified Compound 52 | OC-30 | 26 | 29 | 16 | Invention |
| 2-51 | Exemplified Compound 53 | OC-30 | 29 | 30 | 16 | Invention |
| 2-52 | Exemplified Compound 53 | OC-2 | 41 | 44 | 16 | Invention |
| 2-53 | Exemplified Compound 53 | OC-33 | 30 | 33 | 16 | Invention |
| 2-54 | Exemplified Compound 54 | OC-30 | 31 | 33 | 16 | Invention |
| 2-55 | Exemplified Compound 55 | OC-30 | 31 | 31 | 16 | Invention |
| 2-56 | Exemplified Compound 56 | OC-30 | 32 | 34 | 16 | Invention |
| 2-57 | Exemplified Compound 57 | OC-30 | 29 | 31 | 16 | Invention |
| 2-58 | Exemplified Compound 58 | OC-30 | 31 | 30 | 16 | Invention |
| 2-59 | Exemplified Compound 58 | OC-2 | 44 | 42 | 16 | Invention |
| 2-60 | Exemplified Compound 58 | OC-33 | 30 | 31 | 16 | Invention |

TABLE 4

| Organic EL Element No. | Dopant | Host Compound | Rate of Change in Resistance (Relative Value) | Rate of Change in Half Width of Light Emission Spectrum (Relative Value) | Theoretical Number of Isomers | Note |
| --- | --- | --- | --- | --- | --- | --- |
| 2-61 | Exemplified Compound 59 | OC-30 | 29 | 29 | 16 | Invention |
| 2-62 | Exemplified Compound 60 | OC-30 | 27 | 30 | 16 | Invention |
| 2-63 | Exemplified Compound 61 | OC-93 | 26 | 31 | 16 | Invention |
| 2-64 | Exemplified Compound 62 | OC-30 | 31 | 32 | 16 | Invention |
| 2-65 | Exemplified Compound 63 | ET-25 | 30 | 30 | 16 | Invention |
| 2-66 | Exemplified Compound 64 | OC-30 | 29 | 29 | 16 | Invention |
| 2-67 | Exemplified Compound 65 | OC-30 | 30 | 28 | 16 | Invention |
| 2-68 | Exemplified Compound 66 | OC-30 | 29 | 29 | 16 | Invention |
| 2-69 | Exemplified Compound 66 | OC-2 | 43 | 45 | 16 | Invention |
| 2-70 | Exemplified Compound 66 | OC-33 | 23 | 32 | 16 | Invention |
| 2-71 | Exemplified Compound 67 | OC-30 | 30 | 28 | 16 | Invention |
| 2-72 | Exemplified Compound 68 | OC-95 | 28 | 27 | 16 | Invention |
| 2-73 | Exemplified Compound 69 | OC-30 | 31 | 30 | 16 | Invention |
| 2-74 | Exemplified Compound 70 | OC-30 | 27 | 31 | 16 | Invention |
| 2-75 | Exemplified Compound 71 | OC-30 | 63 | 66 | 4 | Invention |

Tables 2 to 4 evidently show that the rate of change in resistance is substantially correlated with the rate of change in half width of the light emission spectrum. Consequently, the rate of change in resistance of the electrically energized luminous layer can be used as an index in evaluation of the durability of the organic EL element. The comparison of data between the organic EL elements in Table 2 to Table 4 shows that Organic EL elements 2-10 to 2-75 according to the present invention had smaller resistances of the luminous layers and smaller rates of change in half width in the and light emission spectra compared to those of Comparative Organic EL elements 2-1 to 2-9. These results evidently show that the thin luminous layers in the organic EL elements according to the present invention have stable physical properties. Tables 2 to 4 evidently show that use of further preferred host compounds in combination with the complex according to the present invention more significantly contributes to the stable physical properties of the luminous layers.

Although actual determination of the number of existing isomers was performed on only some of exemplified compounds according to the present invention, the rate of change in resistance and the rate of change in half width of the light emission spectrum show a pronounced tendency to decrease as the number of theoretically existing isomers listed in Tables 2 to 4 increases. Such results support the validity of the fundamental technical concept of the present invention, that is, the entropy effect in prevention of change in physical properties of the thin luminous layer, and verify the universality of this technique in stabilization of the luminous layer without varying the ligand skeleton of the complex.

[Example 3] (Application System)

<<Preparation of Organic EL Element 3-1>>

Indium tin oxide (ITO) was applied onto a glass substrate with dimensions of 100 mm×100 mm×1.1 mm (NA45 made by AvanStrate Inc.) to form a film having a thickness of 100 nm. This film was patterned into an anode. This transparent support substrate provided with the ITO transparent electrode was ultrasonically cleaned with isopropyl alcohol, was dried with dry nitrogen gas, and was cleaned with UV ozone for five minutes.

A diluted solution of 70% poly(3,4-ethylenedioxythiophene)-polystyrene sulfonate (PEDOT/PSS, made by Bayer AGC Baytron P Al 4083) in pure water was applied onto the transparent support substrate by spin coating at 3000 rpm for 30 seconds to form a thin film. The coating was dried at 200° C. for one hour to form a first hole transporting layer having a thickness of 20 nm.

This substrate was placed under a nitrogen atmosphere. A solution of ADS254BE (50 mg, made by American Dye Source, Inc.) in 10 ml monochlorobenzene was applied onto the first hole transporting layer by spin coating at 2500 rpm for 30 seconds to form a thin film. The thin film was vacuum dried at 130° C. for one hour to form a second hole transporting layer.

A solution of OC-30 (100 mg) and Dopant D-26 (13 mg) in 10 ml butyl acetate was applied onto the second hole transporting layer by spin coating at 1000 rpm for 30 seconds to form a thin film. The thin film was vacuum dried at 60° C. for one hour to form a luminous layer having a thickness of about 45 nm.

A solution of BCP (50 mg) in 10 ml hexafluoroisopropanol (HFIP) was applied onto the luminous layer by spin coating at 1000 rpm for 30 seconds to form a thin film. The thin film was vacuum dried at 60° C. for one hour to form an electron transporting layer having a thickness of about 25 nm.

This substrate was fixed to the substrate holder of a vacuum deposition apparatus. After the vacuum vessel was evacuated to $4\times10^{-4}$ Pa, potassium fluoride was deposited to form a cathode buffer layer having a thickness of 0.4 nm, and aluminum was deposited to form a cathode having a thickness of 110 nm. Organic EL element 3-1 was thereby prepared.

<<Preparation of Organic EL Elements 3-2 to 3-80>>

Organic EL elements 3-2 to 3-80 were prepared as in Organic EL element 3-1 except that D-26 or OC-30 was replaced with the compounds listed in Tables 5 to 7.

<<Evaluation of Organic EL Elements 3-1 to 3-80>>

For evaluation, the organic EL elements were sealed as in Organic EL element 2-1 in Example 2 to prepare illuminators illustrated in FIGS. 6 and 7.

These samples were evaluated as in Example 1 for the rate of change in resistance of the luminous layer and as in Example 2 for the rate of change in half width of the light emission spectrum. The results are shown in Tables 5 to 7.

TABLE 5

| Organic EL Element No. | Dopant | Host Compound | Rate of Change in Resistance (Relative Value) | Rate of Change in Half-Width of Light Emission Spectrum (Relative Value) | Theoretical Number of Isomers | Note |
|---|---|---|---|---|---|---|
| 3-1 | D-26 | OC-30 | 100 | 100 | 2 | Comparison |
| 3-2 | D-26 | OC-2 | 112 | 116 | 2 | Comparison |
| 3-3 | D-26 | OC-33 | 94 | 89 | 2 | Comparioon |
| 3-4 | Comparative Compound 1 | OC-30 | 99 | 107 | 16 | Comparison |
| 3-5 | Comparative Compound 1 | OC-2 | 118 | 103 | 16 | Comparison |
| 3-6 | Comparative Compound 1 | OC-33 | 104 | 100 | 16 | Comparison |
| 3-7 | Comparative Compound 2 | OC-30 | 95 | 92 | 2 | Comparison |
| 3-8 | Comparative Compound 2 | OC-2 | 112 | 106 | 2 | Comparison |
| 3-9 | Comparative Compound 2 | OC-33 | 89 | 109 | 2 | Comparison |
| 3-10 | Exemplified Compound 2 | OC-33 | 50 | 47 | 16 | Invention |
| 3-11 | Exemplified Compound 3 | OC-33 | 43 | 49 | 16 | Invention |
| 3-12 | Exemplified Compound 5 | OC-33 | 67 | 69 | 4 | Invention |
| 3-13 | Exemplified Compound 6 | OC-33 | 48 | 49 | 16 | Invention |
| 3-14 | Exemplified Compound 7 | OC-30 | 46 | 48 | 16 | Invention |
| 3-15 | Exemplified Compound 7 | OC-2 | 59 | 56 | 16 | Invention |
| 3-16 | Exemplified Compound 7 | OC-33 | 49 | 46 | 16 | Invention |
| 3-17 | Exemplified Compound 8 | OC-33 | 52 | 43 | 16 | Invention |
| 3-18 | Exemplified Compound 10 | OC-33 | 49 | 45 | 16 | Invention |
| 3-19 | Exemplified Compound 13 | OC-33 | 63 | 59 | 8 | Invention |
| 3-20 | Exemplified Compound 13 | OC-30 | 61 | 60 | 8 | Invention |
| 3-21 | Exemplified Compound 14 | OC-2 | 61 | 58 | 16 | Invention |
| 3-22 | Exemplified Compound 14 | OC-33 | 47 | 53 | 16 | Invention |
| 3-23 | Exemplified Compound 15 | OC-2 | 52 | 43 | 16 | Invention |
| 3-24 | Exemplified Compound 16 | OC-33 | 51 | 47 | 16 | Invention |
| 3-25 | Exemplified Compound 17 | OC-33 | 35 | 38 | 16 | Invention |
| 3-28 | Exemplified Compound 19 | OC-91 | 45 | 39 | 16 | Invention |
| 3-27 | Exemplified Compound 20 | OC-33 | 41 | 40 | 16 | Invention |
| 3-28 | Exemplified Compound 21 | OC-33 | 40 | 38 | 16 | Invention |
| 3-29 | Exemplified Compound 23 | OC-33 | 39 | 42 | 16 | Invention |
| 3-30 | Exemplified Compound 25 | OC-30 | 36 | 37 | 16 | Invention |

TABLE 6

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 3-31 | Exemplified Compound 25 | OC-2 | 51 | 49 | 16 | Invention |
| 3-32 | Exemplified Compound 25 | OC-33 | 38 | 40 | 16 | Invention |
| 3-33 | Exemplified Compound 26 | OC-33 | 40 | 36 | 16 | Invention |
| 3-34 | Exemplified Compound 27 | OC-33 | 41 | 34 | 16 | Invention |
| 3-35 | Exemplified Compound 28 | OC-33 | 39 | 37 | 16 | Invention |
| 3-36 | Exemplified Compound 29 | OC-33 | 37 | 40 | 16 | Invention |
| 3-37 | Exemplified Compound 30 | OC-33 | 37 | 37 | 16 | Invention |
| 3-38 | Exemplified Compound 32 | OC-33 | 40 | 36 | 16 | Invention |
| 3-39 | Exemplified Compound 33 | OC-33 | 40 | 40 | 16 | Invention |
| 3-40 | Exemplified Compound 34 | OC-33 | 60 | 59 | 8 | Invention |
| 3-41 | Exemplified Compound 35 | OC-33 | 35 | 32 | 16 | Invention |
| 3-42 | Exemplified Compound 36 | OC-33 | 31 | 40 | 16 | Invention |
| 3-43 | Exemplified Compound 37 | OC-33 | 36 | 39 | 16 | Invention |
| 3-44 | Exemplified Compound 39 | OC-30 | 30 | 31 | 16 | Invention |
| 3-45 | Exemplified Compound 39 | OC-2 | 48 | 53 | 16 | Invention |
| 3-46 | Exemplified Compound 39 | OC-33 | 45 | 42 | 16 | Invention |
| 3-47 | Exemplified Compound 40 | OC-33 | 30 | 34 | 16 | Invention |
| 3-48 | Exemplified Compound 42 | OC-33 | 27 | 31 | 16 | Invention |
| 3-49 | Exemplified Compound 44 | OC-33 | 31 | 27 | 16 | Invention |
| 3-50 | Exemplified Compound 45 | OC-30 | 26 | 29 | 16 | Invention |
| 3-51 | Exemplified Compound 45 | OC-2 | 40 | 41 | 16 | Invention |
| 3-52 | Exemplified Compound 45 | OC-33 | 41 | 44 | 16 | Invention |
| 3-53 | Exemplified Compound 46 | OC-33 | 30 | 33 | 16 | Invention |
| 3-54 | Exemplified Compound 47 | OC-33 | 31 | 33 | 16 | Invention |
| 3-55 | Exemplified Compound 48 | OC-33 | 31 | 31 | 16 | Invention |

TABLE 6-continued

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 3-56 | Exemplified Compound 49 | OC-33 | 32 | 34 | 16 | Invention |
| 3-57 | Exemplified Compound 50 | OC-33 | 29 | 31 | 16 | Invention |
| 3-58 | Exemplified Compound 52 | OC-30 | 31 | 30 | 16 | Invention |
| 3-59 | Exemplified Compound 52 | OC-2 | 43 | 45 | 16 | Invention |
| 3-60 | Exemplified Compound 52 | OC-33 | 30 | 31 | 16 | Invention |

TABLE 7

| Organic EL Element No. | Dopant | Host Compound | Rate of Change in Resistance (Relative Value) | Rate of Change in Half Width of Light Emission Spectrum (Relative Value) | Theoretical Number of Isomers | Note |
|---|---|---|---|---|---|---|
| 3-61 | Exemplified Compound 53 | OC-33 | 29 | 29 | 16 | Invention |
| 3-62 | Exemplified Compound 54 | OC-33 | 28 | 30 | 16 | Invention |
| 3-63 | Exemplified Compound 55 | OC-33 | 26 | 31 | 16 | Invention |
| 3-64 | Exemplified Compound 56 | OC-33 | 32 | 32 | 16 | Invention |
| 3-65 | Exemplified Compound 57 | OC-30 | 30 | 30 | 16 | Invention |
| 3-66 | Exemplified Compound 57 | OC-2 | 46 | 41 | 16 | Invention |
| 3-67 | Exemplified Compound 57 | OC-33 | 30 | 29 | 16 | Invention |
| 3-68 | Exemplified Compound 58 | OC-33 | 29 | 32 | 16 | Invention |
| 3-69 | Exemplified Compound 59 | OC-33 | 34 | 37 | 16 | Invention |
| 3-70 | Exemplified Compound 60 | OC-33 | 23 | 32 | 16 | Invention |
| 3-71 | Exemplified Compound 61 | OC-33 | 33 | 30 | 16 | Invention |
| 3-72 | Exemplified Compound 62 | OC-33 | 28 | 32 | 16 | Invention |
| 3-73 | Exemplified Compound 63 | OC-33 | 32 | 31 | 16 | Invention |
| 3-74 | Exemplified Compound 64 | OC-33 | 28 | 30 | 16 | Invention |
| 3-75 | Exemplified Compound 65 | OC-33 | 30 | 31 | 16 | Invention |
| 3-76 | Exemplified Compound 66 | OC-94 | 35 | 27 | 16 | Invention |
| 3-77 | Exemplified Compound 67 | OC-33 | 31 | 32 | 16 | Invention |
| 3-78 | Exemplified Compound 68 | OC-33 | 34 | 29 | 16 | Invention |
| 3-79 | Exemplified Compound 69 | OC-33 | 30 | 33 | 16 | Invention |
| 3-80 | Exemplified Compound 71 | OC-33 | 68 | 64 | 4 | Invention |

Tables 5 to 7 evidently show that Organic EL elements 3-10 to 3-80 according to the present invention had smaller rates of change in resistance of the luminous layer and smaller rates of change in half width of the light emission spectrum than those of Organic EL elements 3-1 to 3-9 in Comparative Examples. These results evidentially show that the thin luminous layers in the organic EL elements according to the present invention have stable physical properties.

Tables 5 to 7 evidently show that use of further preferred host compounds in combination with the complex according to the present invention more significantly contributes to the stable physical properties of the luminous layers. Although actual determination of the number of existing isomers was performed on only some of the exemplified compounds according to the present invention, the rate of change in resistance and the rate of change in half width of the light emission spectrum show a pronounced tendency to decrease as the number of theoretically existing isomers listed in Tables 5 to 7 increases. Such results support the validity of the fundamental technical concept of the present invention, that is, the entropy effect in prevention of change in physical properties of the thin luminous layer, and verify the universality of this technique in stabilization of the luminous layer without varying the ligand skeleton of the complex.

[Example 4] (White Luminescent System)

<<Preparation of Organic EL Element 4-1>>

Indium tin oxide (ITO) was applied onto a glass substrate with dimensions of 100 mm×100 mm×1.1 mm (NA45 made by AvanStrate Inc.) to form a film having a thickness of 100 nm. This film was patterned into an anode. This transparent support substrate provided with the ITO transparent electrode was ultrasonically cleaned with isopropyl alcohol, was dried with dry nitrogen gas, and was cleaned with UV ozone for five minutes.

After the transparent support substrate was fixed to a substrate holder in a commercially available vacuum deposition apparatus, 4,4'-bis[N-(3-methylphenyl)-N-phenylamino]biphenyl (TPD) (200 mg), CBP (200 mg), Dopant D-9 (200 mg), Dopant D-1 (200 mg), Dopant D-6 (200 mg), and BCP (200 mg) were separately placed in molybdenum resistive heating boats, and these molybdenum resistive heating boats were placed in a vacuum deposition apparatus.

The vacuum vessel was evacuated to 4×10$^{-4}$ Pa, and the heating boat containing TPD was electrically heated to deposit TPD on the transparent support substrate at a deposition rate of 0.1 nm/sec to form a hole transporting layer having a thickness of 10 nm.

The heating boats containing CBP, D-9, D-1, and D-6 were electrically heated to co-deposit these compounds on the hole transporting layer at deposition rates of 0.1 nm/sec, 0.025 nm/sec, 0.0007 nm/sec, and 0.0002 nm/sec, respectively, to form a luminous layer having a thickness of 60 nm.

The heating boat containing BCP was electrically heated to deposit BCP on the luminous layer at a deposition rate of 0.1 nm/sec to form an electron transporting layer having a thickness of 20 nm.

Potassium fluoride was then deposited to form a cathode buffer layer having a thickness of 0.5 nm, and aluminum was deposited to form a cathode having a thickness of 110 nm. Organic EL element 4-1 was thereby prepared.

Organic EL element 4-1 was electrically energized to emit substantially white light. Organic EL element 4-1 is suitable for use in an illuminator. It was confirmed that Organic EL elements 4-2 to 4-9 according to the present invention emitted white light having a chromaticity at 1000 cd/m$^2$ in the CIE 1931 color system within the region defined by x=0.33±0.07 and y=0.33±0.1 in the measurement of the front luminance at a view angle of 2 degrees.

<<Preparation of Organic EL Elements 4-2 to 4-9>>

Organic EL elements 4-2 to 4-9 were prepared as in Organic EL element 3-1 except that D-9 was replaced with the compounds listed in Table 8.

<<Evaluation of Organic EL Elements 4-1 to 4-9>>

The rate of change in resistance of the luminous layer was measured as in Example 1. The rates of change in resistance of the luminous layer in the organic EL elements according to the present invention were equal to or less than a half of those in Comparative Examples.

TABLE 8

| Organic EL Element No. | Dopant | Note |
| --- | --- | --- |
| 4-1 | D-9 | Comparison |
| 4-2 | Exemplified Compound 18 | Invention |
| 4-3 | Exemplified Compound 34 | Invention |
| 4-4 | Exemplified Compound 36 | Invention |
| 4-5 | Exemplified Compound 46 | Invention |
| 4-6 | Exemplified Compound 53 | Invention |
| 4-7 | Exemplified Compound 59 | Invention |
| 4-8 | Exemplified Compound 67 | Invention |
| 4-9 | Exemplified Compound 69 | Invention |

[Example 5] (Color)

<<Preparation of Organic EL Element 5-1>>

(Preparation of Blue Luminescent Element)

Organic EL element 2-55 in Example 2 was used as a blue luminescent element.

(Preparation of Green Luminescent Element)

A green luminescent element was prepared as in Organic EL element 2-55 in Example 2 except that Exemplified compound 55 was replaced with D-1. This green luminescent element was evaluated.

(Preparation of Red Luminescent Element)

A red luminescent element was prepared as in Organic EL element 2-55 in Example 2 except that Exemplified compound 55 was replaced with D-6. This red luminescent element was evaluated.

These red, green, and blue organic EL elements were disposed on a substrate to prepare an active matrix full-color display illustrated in FIG. 2. FIG. 3 illustrates only a schematic view of the display unit C in the display.

The display includes a substrate, a line unit including multiple scanning lines 5 and multiple data lines 6, and multiple pixels 3 (pixels emitting red, green, and green light beams). The scanning lines 5 and the data lines 6 in the line unit are composed of a conductive material. The scanning lines 5 intersect orthogonal to the data lines 6 in the form of a grating. The intersections are connected to the pixels 3 (details are not illustrated).

In such an active matrix display, the pixels 3 each include a color organic EL element, and active elements, i.e., a switching transistor and a driving transistor. Each pixel receives a scanning signal from the corresponding scanning line 5, and receives an image data signal from the corresponding data line 6 to emit light according to the received image data. The red, green, and blue pixels were appropriately disposed to prepare a full-color display.

This full-color display had high luminance and high durability and displayed sharp multicolor moving pictures.

INDUSTRIAL APPLICABILITY

The mixed isomeric metal complex composition according to the present invention comprises atropisomers having very close physical properties and energy levels. The present invention provides an organic electroluminescent element including a luminous layer composed of the mixed isomeric metal complex composition as an organic electroluminescent material to enhance long-term stability of organic metal complexes in a film and attain a small change in resistance of the luminous layer and a small change in half width of an emission spectrum. The present invention also provides illuminators and displays including the organic electroluminescent element.

DESCRIPTION OF REFERENCE NUMERALS 1 display
3 pixel
5 scanning line
6 data line
7 power supply line
10 organic EL element
11 switching transistor
12 driving transistor
13 capacitor
101 organic EL element
102 glass cover
105 cathode
106 organic EL layer
107 glass substrate with transparent electrode
108 nitrogen gas
109 moisture getter
A component A
B component B
C display unit
D control unit

The invention claimed is:

1. A mixed isomeric metal complex composition comprising atropisomers,
wherein each of the atropisomers comprises a metal atom and multiple ligands, at least one of the ligands has an aromatic ring as a substituent, and the atropisomers are present due to hindered free rotation of a bond axis between the aromatic ring and the at least one ligand after formation of a complex with the metal atom and the ligands,
wherein the atropisomers are represented by Formula (1)':

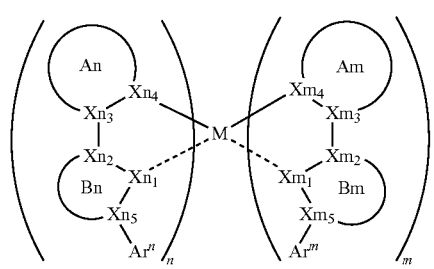

Formula (1)' wherein each of rings Bm and Bn is substituted, and each of rings Am and An optionally has a substituent, rings Am and An independently represent a 6-membered aromatic hydrocarbon ring, and rings Bm and Bn independently represent a 5-membered aromatic heterocycle; $Xm_3$, $Xm_4$, $Xn_3$, and $Xn_4$ in the rings Am and An are carbon, $Xm_1$, $Xm_2$, $Xm_5$, $Xn_1$, $Xn_2$, and $Xn_5$ in the rings Bm and Bn each represent a carbon atom or a nitrogen atom, with at least one of $Xm_1$, $Xm_2$, and $Xm_5$ representing a nitrogen atom, and at least one of $Xn_1$, $Xn_2$, and $Xn_5$ representing a nitrogen atom;
$Xm_1$ and M and $Xn_1$ and M form coordination bonds, $Xm_4$ and M and $Xn_4$ and M form covalent bonds;
$Ar'''$ and $Ar''$ each represent an aromatic hydrocarbon ring or an aromatic heterocyclic group having no symmetrical axis in a bond axis to the ring Bm or Bn, and optionally have a substituent; and
M represents iridium or platinum; m and n each represent an integer of 0 to 3; wherein when M is platinum, m+n represents 2 and when M is iridium m+n represents 3,
in Formula (1)', at least one of a ligand formed by combination of the rings An and Bn or a ligand formed by combination of the rings Am and Bm is represented by Formula (3) or Formula (6),

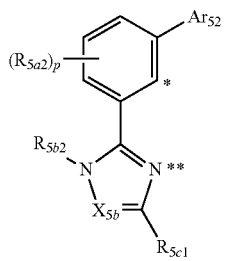

Formula (3)

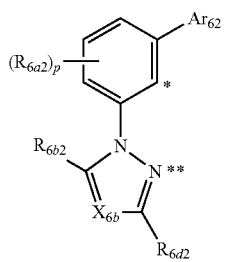

Formula (6)

where $R_{5a2}$ and $R_{6a2}$ each independently represent a halogen atom, a cyano group, an alkyl group, an alkenyl group, an alkynyl group, an alkoxy group, an amino group, a silyl group, an arylalkyl group, an aromatic hydrocarbon ring, an aromatic heterocyclic group, a non-aromatic hydrocarbon ring, or a non-aromatic heterocyclic group, and optionally have a substituent; p represents an integer of 0 to 3;
$R_{5b2}$ represents an alkyl group, an aromatic hydrocarbon ring, an aromatic heterocyclic group, a non-aromatic hydrocarbon ring, or a non-aromatic heterocyclic group, and optionally have a substituent; $X_{5b}$ represents $=C(R_{5e})-$ or $=N-$;
$R_{5e}$ represents an alkyl group, an aromatic hydrocarbon ring, an aromatic heterocyclic group, a non-aromatic hydrocarbon ring, or a non-aromatic heterocyclic group;
$R_{6b2}$ independently represents a hydrogen atom, an alkyl group, an aromatic hydrocarbon ring, an aromatic heterocyclic group, a non-aromatic hydrocarbon ring, or a non-aromatic heterocyclic group, and optionally have a substituent;
$R_{5c1}$ and $R_{6d2}$ independently represent an aromatic hydrocarbon ring or an aromatic heterocyclic group having no symmetrical axis in the bond axis, and optionally has a substituent;
$X_{6b}$ represents $=C(R_{6e})-$ or $=N-$;
$R_{6e}$ represents an alkyl group, an aromatic hydrocarbon ring, an aromatic heterocyclic group, a non-aromatic hydrocarbon ring, or a non-aromatic heterocyclic group;
$Ar_{52}$ and $Ar_{62}$ each independently represent an aromatic hydrocarbon ring represented by Formula (4):

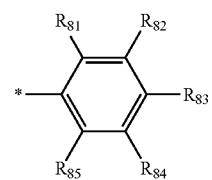

Formula (4)

where $R_{81}$ to $R_{85}$ each independently represent a hydrogen atom, a halogen atom, a cyano group, an alkyl group, an alkenyl group, an alkynyl group, an alkoxy group, an amino group, a silyl group, an arylalkyl group, an aryl group, a heteroaryl group, a non-aromatic hydrocarbon ring, or a non-aromatic heterocyclic group, and optionally have a substituent; two adjacent groups of $R_{81}$ to $R_{85}$ may bond to each other to form a ring;
wherein $R_{81}$ is not the same as $R_{85}$ when $R_{82}=R_{84}$, and $R_{82}$ is not the same as $R_{84}$ when $R_{81}=R_{85}$;
wherein in Formula (3) and Formula (6) * represents a covalent bonding site to M and ** represents a coordination bonding site to M,
and in Formula (4), * represents a bonding site to which $Ar_{52}$ is attached in Formula (3) and a bonding site to which $Ar_{62}$ is attached in Formula (6).

2. An organic electroluminescent metal complex composition comprising the mixed isomeric metal complex composition comprising atropisomers according to claim 1, wherein the mixed isomeric metal complex composition is a phosphorescent material for organic electroluminescent elements.

3. An organic electroluminescent element including a pair of electrodes, and one or more organic layers disposed between the pair of electrodes, wherein one of the organic layers contains the organic electroluminescent metal complex composition according to claim 2.

4. The organic electroluminescent element according to claim 3, wherein the one organic layer contains a mixture of the organic electroluminescent metal complex composition and a host compound having a freely rotating biaryl structure.

5. The organic electroluminescent element according to claim 4, wherein the host compound having a freely rotating biaryl structure has a dibenzofuran structure.

6. The organic electroluminescent element according to claim 4, wherein the host compound having a freely rotating biaryl structure has a carbazole structure.

7. The organic electroluminescent element according to claim 4, wherein the host compound having a freely rotating biaryl structure has an unsubstituted phenyl group.

8. An illuminator including the organic electroluminescent element according to claim 3.

9. A display including the organic electroluminescent element according to claim 3.

10. The mixed isomeric metal complex composition according to claim 1, wherein M is iridium.

* * * * *